(12) United States Patent
Gray et al.

(10) Patent No.: US 6,946,475 B1
(45) Date of Patent: Sep. 20, 2005

(54) ANTICANCER CALCIUM CHANNEL BLOCKERS

(75) Inventors: Lloyd S. Gray, Charlottesville, VA (US); Timothy L. Macdonald, Charlottesville, VA (US); Doris Haverstick, Charlottesville, VA (US); Tiffany N. Heady, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 09/544,968

(22) Filed: Apr. 7, 2000

Related U.S. Application Data

(60) Provisional application No. 60/128,143, filed on Apr. 7, 1999.

(51) Int. Cl.[7] ..................... A61K 31/445; A61K 31/40; C07D 207/46; C07D 211/20
(52) U.S. Cl. ................. 514/317; 514/428; 546/236; 548/570
(58) Field of Search .................. 546/236; 548/570; 514/317, 428

(56) References Cited

U.S. PATENT DOCUMENTS

| | | | |
|---|---|---|---|
| 3,732,247 A | 5/1973 | Helsley et al. | 260/326.8 |
| 4,908,365 A | 3/1990 | Buzas et al. | 514/252 |
| 4,957,927 A | 9/1990 | Ferrand et al. | 514/428 |

FOREIGN PATENT DOCUMENTS

| | | |
|---|---|---|
| EP | 0 805 147 A1 | 11/1997 |
| WO | WO 92/05172 | 4/1992 |
| WO | WO 97/10212 | 3/1997 |

OTHER PUBLICATIONS

Benzaquen, Laura R., et al. "Clotrimazole inhibits cell proliferation in vitro and in vivo", Nature Medicine, vol. 1., No. 6, Jun. 1995, pp. 524–540.

Cohen, R.B., et al. "Pilot study of pharmacologic inhibition of calcium entry blockers in the treatment of advanced breast and prostate cancer", Proc. Annu. Meet. Am. Soc. Clin. Oncol., vol. 16, 1997, p. 538a.

Densmore, John J., et al., "A voltage–gated calcium channel is linked to the antigen receptor in Jurkat T lymphocytes", Febs Letters, vol. 312, No. 2,3, Nov. 1992, p. 161–164.

Densmore, John J., et al. "A voltage–operable current is involved in Ca2+ entry in human lymphocytes whereas ICRAC has no apparent role", Am. J. Physiol, vol. 271 (1996).

Haverstick, Doris M., "Calmodulin regulation of Ca2+ entry in Jurkat T cells", Cell Calcium, 23(6):361–367, (1998).

Wikstrom, Peter, et al. "Additional peptidyl diazomethyl ketones, including biotinyl derivatives, which affinity–label calpain and related cysteinyl proteinases", J. Enzyme Inhibition, 1993 vol. 6, pp. 259–269.

*Primary Examiner*—Rita Desai
*Assistant Examiner*—Raymond Covington
(74) *Attorney, Agent, or Firm*—John P. Breen

(57) ABSTRACT

The present invention is directed to compounds useful as cancer cell inhibitors, compositions containing such compounds and methods for inhibiting proliferation of electrically non-excitable cells.

38 Claims, 42 Drawing Sheets

PC3 - TH-1087

$EC_{50} = 9.9\ \mu M$

[TH-1087] ($\mu M$)

| [TH-1087] | PC3 | | |
|---|---|---|---|
| | Y | SEM | N |
| 100 | 50.4 | 4.84 | 6 |
| 30 | 41.8 | 3.02 | 6 |
| 10 | 72.3 | 0.95 | 6 |
| 3 | 102.0 | 3.73 | 6 |
| 1 | 99.8 | 5.77 | 6 |

LNCaP/TH-1087

| [TH-1087] | LNCaP | | |
|---|---|---|---|
| | Y | SEM | N |
| 1 | 96.8 | 1.29 | 3 |
| 3 | 89.7 | 1.60 | 3 |
| 10 | 8.5 | 0.06 | 3 |
| 30 | 5.4 | 0.19 | 3 |
| 100 | 4.7 | 0.15 | 3 |

Jurkat - TH-1113

| [TH-1113] | Jurkat | | |
|---|---|---|---|
| | Y | SEM | N |
| 0 | 95.4 | 2.49 | 9 |
| 0 | 104.6 | 2.71 | 9 |
| 100 | 1.0 | 0.73 | 9 |
| 30 | 6.1 | 0.58 | 9 |
| 10 | 68.7 | 1.81 | 9 |
| 3 | 97.2 | 3.01 | 9 |
| 1 | 105.2 | 3.82 | 9 |

PC3 - TH-1113

[TH-1113] (μM)

| [TH-1113] | PC3 | | |
|---|---|---|---|
| | Y | SEM | N |
| 0 | 106.7 | 3.34 | 6 |
| 0 | 93.3 | 2.44 | 6 |
| 100 | 33.4 | 1.41 | 6 |
| 30 | 109.0 | 3.56 | 6 |
| 10 | 110.8 | 1.83 | 6 |
| 3 | 109.5 | 1.56 | 6 |
| 1 | 105.6 | 2.34 | 6 |

LNCaP/TH-1113

| [TH-1113] | Data Set-A | | |
|---|---|---|---|
| | Y | SEM | N |
| 100 | 1.3 | 0.96 | 9 |
| 30 | 2.2 | 1.14 | 9 |
| 10 | 35.3 | 16.22 | 9 |
| 3 | 87.8 | 6.77 | 9 |
| 1 | 98.8 | 2.52 | 9 |

MDA-468-TH-1113

| [TH-1113] | MDA-468 | | |
|---|---|---|---|
| | Y | SEM | N |
| 0 | 101.5 | 2.40 | 6 |
| 0 | 98.5 | 1.69 | 6 |
| 100 | -0.1 | 0.14 | 6 |
| 30 | 50.3 | 1.91 | 6 |
| 10 | 79.4 | 6.85 | 6 |
| 3 | 84.1 | 6.19 | 6 |
| 1 | 80.6 | 6.60 | 6 |

MDA-361-TH-1113

| [TH-1113] | MDA-361 | | |
|---|---|---|---|
| | Y | SEM | N |
| 0 | 108.4 | 2.09 | 6 |
| 0 | 91.7 | 0.46 | 6 |
| 100 | 0.1 | 0.29 | 6 |
| 30 | 41.8 | 1.11 | 6 |
| 10 | 85.5 | 3.11 | 6 |
| 3 | 91.3 | 4.03 | 6 |
| 1 | 85.0 | 4.08 | 6 |

MDA-468/TH-1211

| X Title | Data Set-A | | |
|---|---|---|---|
| | Y | SEM | N |
| 100 | 0.6 | 0.47 | 3 |
| 30 | 46.5 | 1.29 | 3 |
| 10 | 74.9 | 2.48 | 3 |
| 3 | 94.7 | 1.37 | 3 |
| 1 | 96.9 | 1.79 | 3 |

LNCaP/TH-1205

| [TH-1205] | Data Set-A | | |
|---|---|---|---|
| | Y | SEM | N |
| 1 | 84.7 | 2.15 | 3 |
| 3 | 86.5 | 0.54 | 3 |
| 10 | 2.3 | 0.21 | 3 |
| 30 | 1.1 | 0.14 | 3 |
| 100 | 1.1 | 0.12 | 3 |

MDA-468/TH-1205

| [TH-1205] | Data Set-A | | |
|---|---|---|---|
| | Y | SEM | N |
| 1 | 98.5 | 4.07 | 3 |
| 3 | 100.4 | 2.71 | 3 |
| 10 | 85.6 | 1.59 | 3 |
| 30 | 13.6 | 1.16 | 3 |
| 100 | 3.5 | 0.15 | 3 |

MDA-361/TH-1205

| [TH-1205] | Data Set-A | | |
|---|---|---|---|
| | Y | SEM | N |
| 1 | 100.0 | 0.60 | 3 |
| 3 | 97.3 | 2.45 | 3 |
| 10 | 87.5 | 1.33 | 3 |
| 30 | 0.2 | 0.16 | 3 |
| 100 | 1.1 | 0.13 | 3 |

ANTICANCER CALCIUM CHANNEL BLOCKERS

RELATED APPLICATION

This application claims benefit from U.S. Provisional Application No. 60/128,143, filed Apr. 7, 1999.

FIELD OF THE INVENTION

The present invention relates to novel compounds useful as cancer cell inhibitors, compositions containing such compounds, methods for inhibiting calcium entry into electrically non-excitable cells as well as methods for preventing proliferation of electrically non-excitable cells.

BACKGROUND OF THE INVENTION

Anti-metabolic, cytotoxic therapies for cancer have achieved success in extending the lives of people afflicted with this disease. The goal of this approach to cancer treatment, at its limit, is the complete eradication of cancer cells. Elimination of all residual cancer cells results in cure, although emergence of drug resistance or of more aggressive disease often hampers this outcome. The goal of cytostatic cancer therapies is to retard cellular proliferation rather than eliminate all cancer cells. Controlling the growth of cancer would, at one extreme, effectively render the disease impotent. Failure to completely control the growth of cancer would nonetheless be clinically valuable if, for example, cytostatic therapy significantly extended the duration of remissions induced by cytotoxic agents.

Malignant transformation is often associated with the acquisition of a phenotype that is consistent with an abnormally high sensitivity to ambient concentrations of growth factors. In prostate cancer, for example, the source of such growth factors can be autocrine, from the cancer cells themselves, or from the surrounding stroma in a paracrine fashion (Russel et al. (1998) *Clin. Chem.* 44(4): 705–723, Steiner, M. S. (1993) *Urology* 42: 99–110). The molecular role of growth factors and their corresponding receptors in malignant transformation and cancer progression is complex and not yet well understood.

Growth factor receptors are often linked to the pathway that regulates calcium homeostasis. The mitogenic interaction of a growth factor with its receptor can activate a pathway that includes enhancement of the entry of extracellular $Ca^{2+}$. Engagement of a growth factor receptor by an appropriate ligand results in the activation of phospholipase C by tyrosine phosphorylation (Exton, J. H. *Ann. Rev. Pharmacol. Toxicol,* 36: 481–509). Activated phospholipase C metabolizes phosphatidyl inositol bisphosphate to produce diacylglycerol and inositol 1,4,5-triphosphate (Berridge et al. (1984) *Nature* 312: 315–321). Inositol triphosphate releases $Ca^{2+}$ from an internal storage depot, and this release of intracellular $Ca^{2+}$ triggers the influx of extracellular $Ca^{2+}$ (Berridge, supra).

The role of enhanced $Ca^{2+}$ entry in the proliferation of cancer cells is not well understood. It has been shown, however, that proliferation of at least some cancer cell lines can be slowed or stopped at specific points in the cell cycle by removal of extracellular $Ca^{2+}$. (Meldolesi, J. (1995) *Nat. Med.* 1: 512–513; Alessandro et al. (1996) *In Vivo* 10:153–160). Consistent with this observation is that a drug that blocks $Ca^{2+}$ entry can retard the metastasis of human melanoma cells in immune deficient mice (Benzaquen et al. (1995) *Nat. Med.* 1: 534–540).

While the role of $Ca^{2+}$ entry in cancer cell proliferation has been known for some time, the use of directed $Ca^{2+}$ entry antagonists for the suppression of $Ca^{2+}$ influx and treatment of cancer had not been developed until now. For the first time and in accordance with the present invention, compounds have been developed that block growth factor receptor-linked $Ca^{2+}$ entry and growth factor-driven cellular proliferation both in vitro and in vivo. The compounds of the present invention are useful for inhibiting $Ca^{2+}$ entry into and proliferation of cancer cells, such as breast and prostate cancer cells, without apparent toxicity.

SUMMARY OF THE INVENTION

Accordingly, the present invention is directed to novel compounds useful for retarding the proliferation of cancerous cells and having the formula:

$$\text{(I)}$$

and pharmaceutically acceptable salts thereof
wherein
X is N or CH;

is a 5–10 membered cyclic ring which is saturated and which may contain 1 or 2 additional ring heteroatoms selected from the group consisting of O, S and N, with the remaining ring atoms being carbon atoms;

$R_1$ is $(CH_2)n$—Z—$(R_5)$, Q, hydrogen or lower alkyl;

$R_2$ is hydrogen or Q', provided that $R_1$ is Q or $R_2$ is Q';

Q and Q' may be the same or different and are independently $$(CH_2)n_1\text{—}Y\text{—}(CH_2)n_2\text{—}CH\begin{array}{c}R_3\\ \diagdown\\ R_4\end{array};$$

Z is a chemical bond, $CH_2$, O, S or NH;

Y is $CH_2$, O, S or NH;

$R_3$, $R_4$ and $R_5$ are independently cyclic rings containing 6–14 ring carbon atoms, and containing no hetero ring atoms, which cyclic rings may be completely saturated, partially unsaturated or aromatic, and which are unsubstituted or substituted with an electron donating group or electron withdrawing group; or $R_3$ and $R_4$ may be fused to form a cyclic ring structure containing 12–28 carbon atoms;

$R_{10}$, $R_6$ and $R_{11}$ are independently hydrogen or lower alkyl, which is unsubstituted or substituted with an electron withdrawing group or electron donating group;

$n_2$ is 0 to 8; and $n_2$ and $n_1$ are independently 1–8.

These compounds are calcium antagonists and are effective calcium channel blockers.

The present invention is also directed to pharmaceutical compositions containing a pharmaceutically effective amount of these compounds and a pharmaceutical carrier therefor. The present invention is also directed to treating cancer in a mammal afflicted therewith comprising administering to said mammal a cytostatic effective amount of said compound. The present invention is also directed to a method for inhibiting cancer cell proliferation in a mammal in need of such treatment comprising administering to said mammal a cytostatic effective amount of said compound. The present invention is also directed to a method for retarding the entry of calcium into electrically non-excitable cells of a mammal comprising administering to said mammal an amount of said compound effective to retard calcium absorption into electrically non-excitable cells of said mammal.

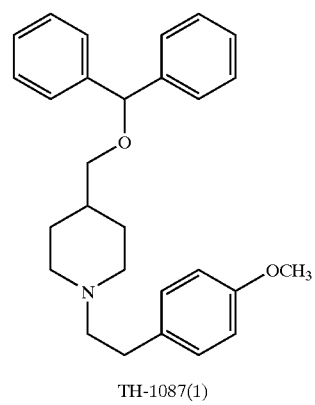

TH-1087(1)

-continued
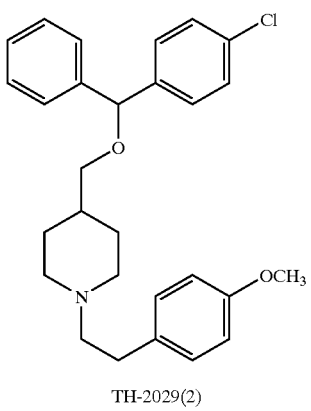
TH-2029(2)
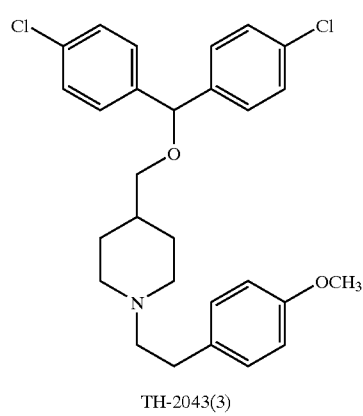
TH-2043(3)
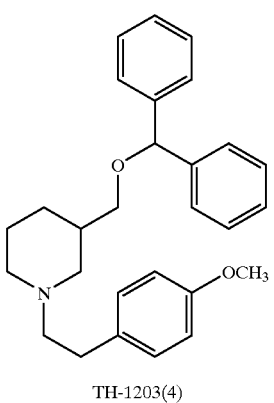
TH-1203(4)
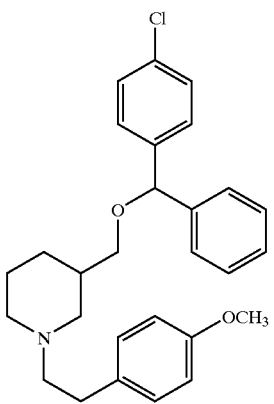
TH-1205(5)
-continued
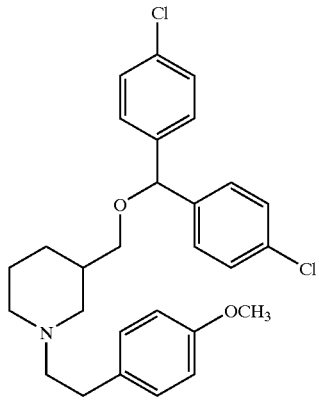
TH-2179(6)
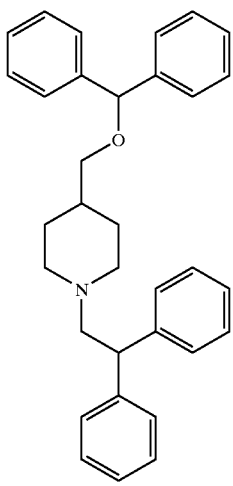
MMR-70(7)
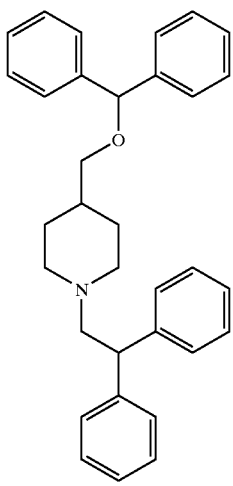
MMR-92(8)

-continued
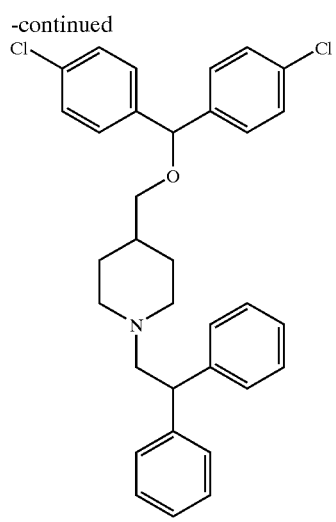
MMR-100(9)
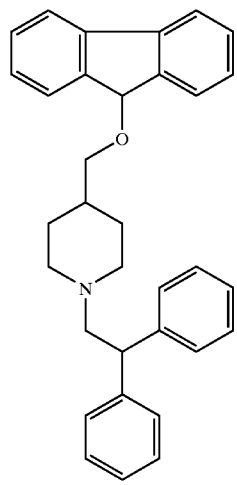
MMR-1104(10)
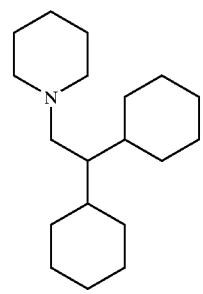
MMR-79(11)
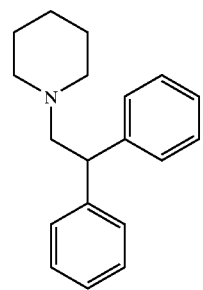
MMR-64(12)
-continued
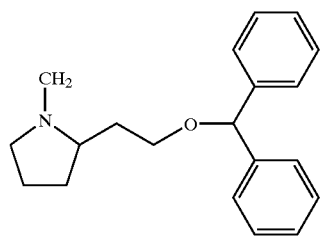
TH-2149(13)
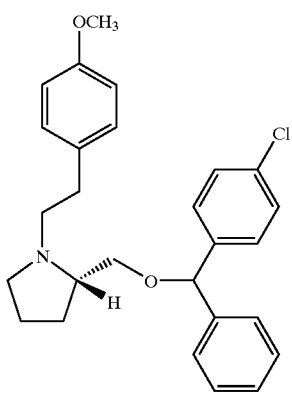
TH-1113(14)
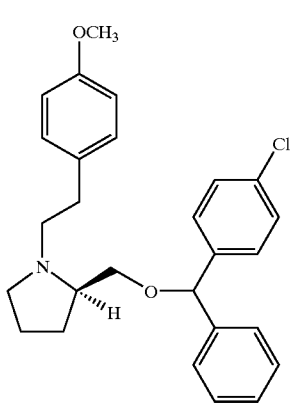
TH-1177(15)
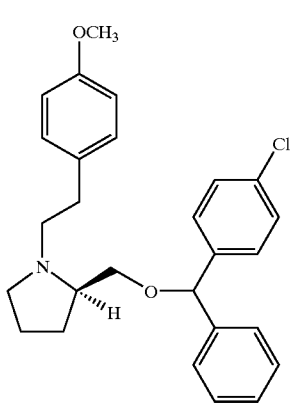
TH-1211(16)

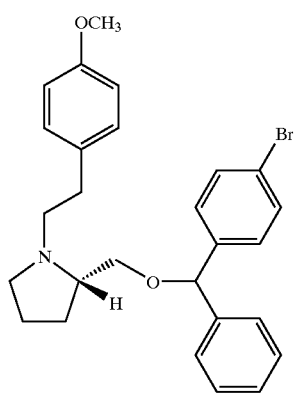
TH-2210(17)
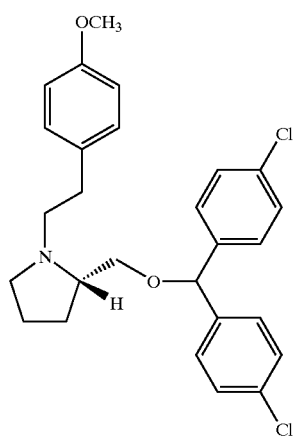
TH-2019(18)
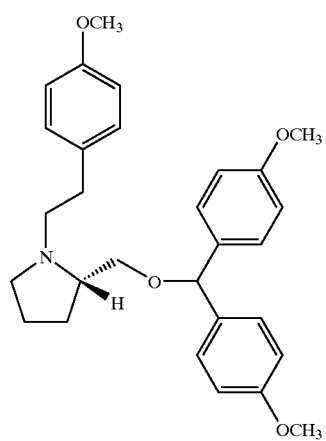
TH-2129(19)
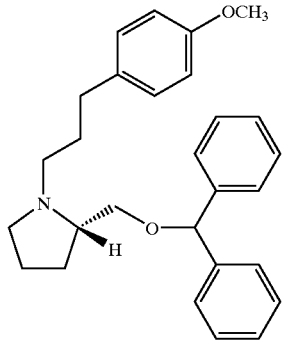
TH-2083(20)
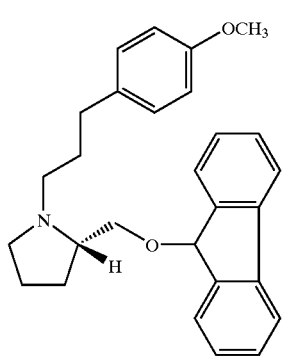
TH-2086(21)
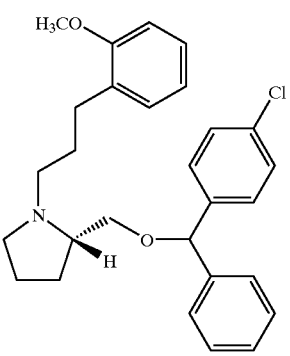
TH-2151(22)
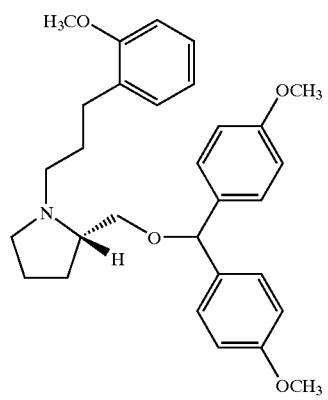
TH-2153(23)

-continued

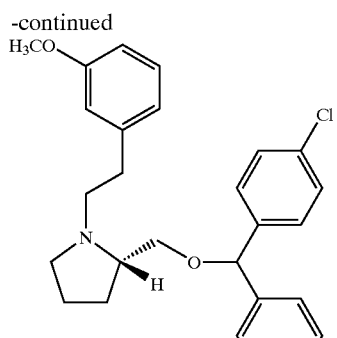
TH-3105(26)

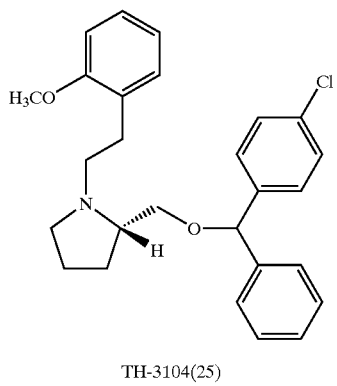
TH-3104(25)

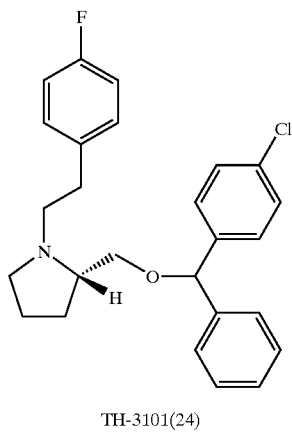
TH-3101(24)

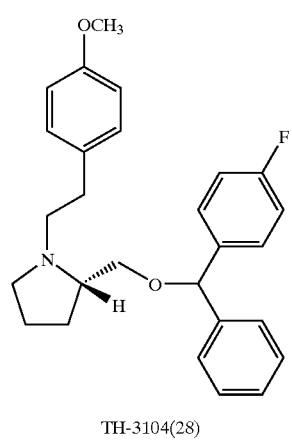
TH-3104(28)

-continued

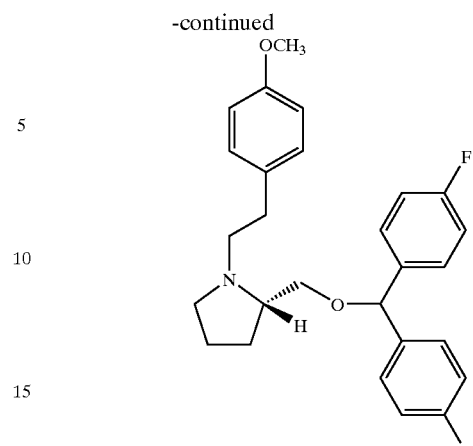
YH-1096(29)

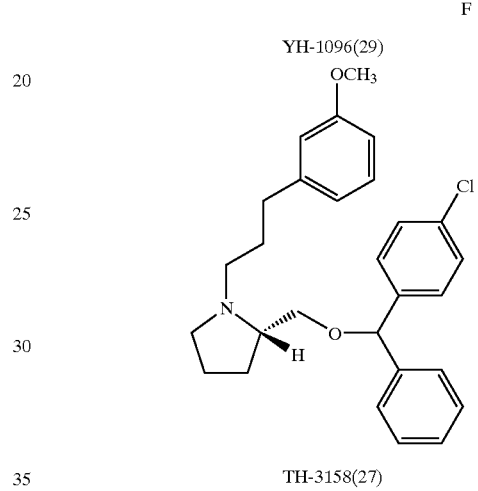
TH-3158(27)

Figure 41:
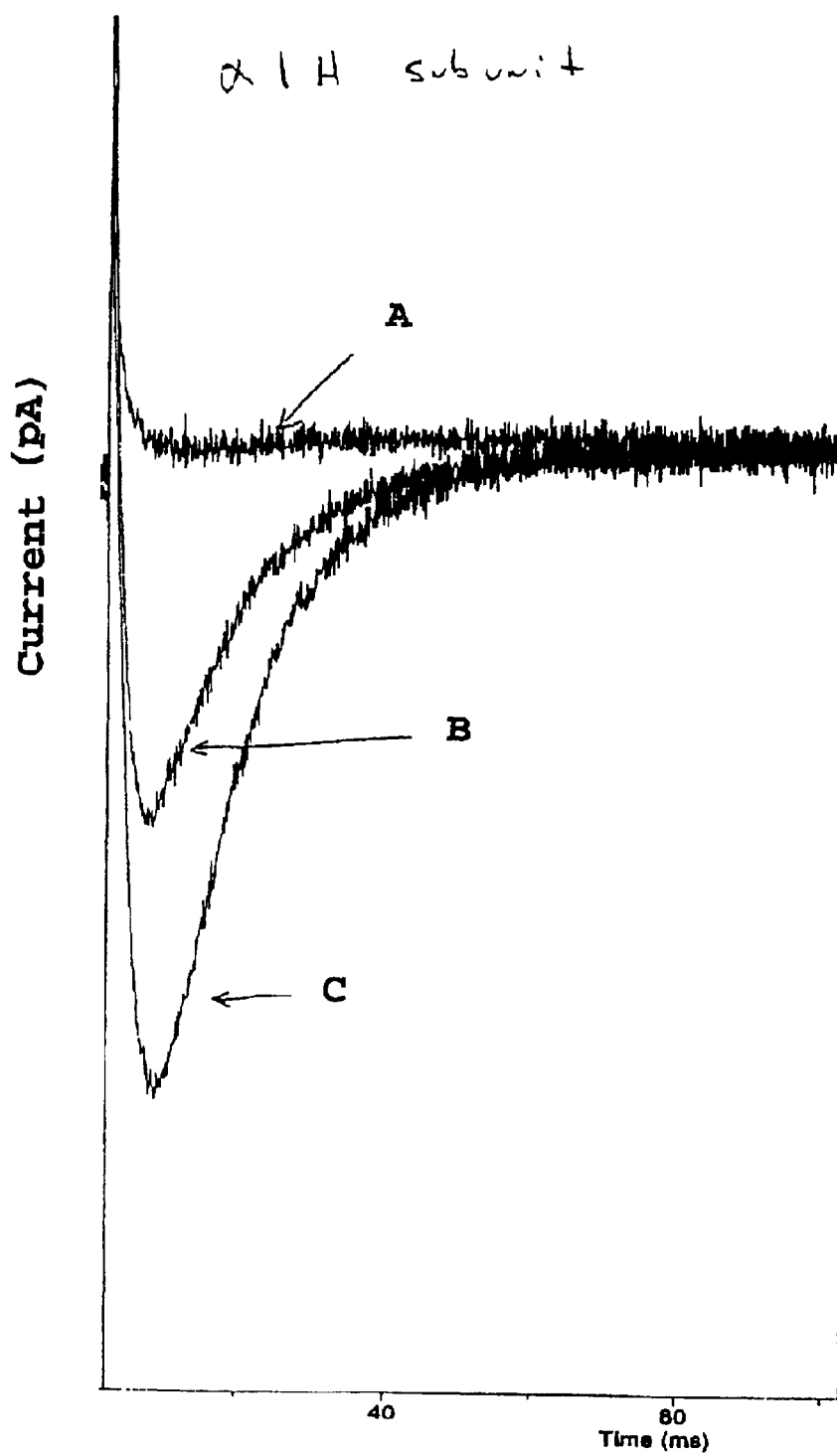

FIG. 41 graphically shows the ability of TH-1177 to inhibit calcium crossing the cell membrane of xenopus oocytes transfected with the alpha 1H subunit of a calcium channel. Legend A is a graph when 10 μM TH-1177 was added to the medium, B is a graph of the effect on the washout of TH-1177 and C is the control.

Figure 42:
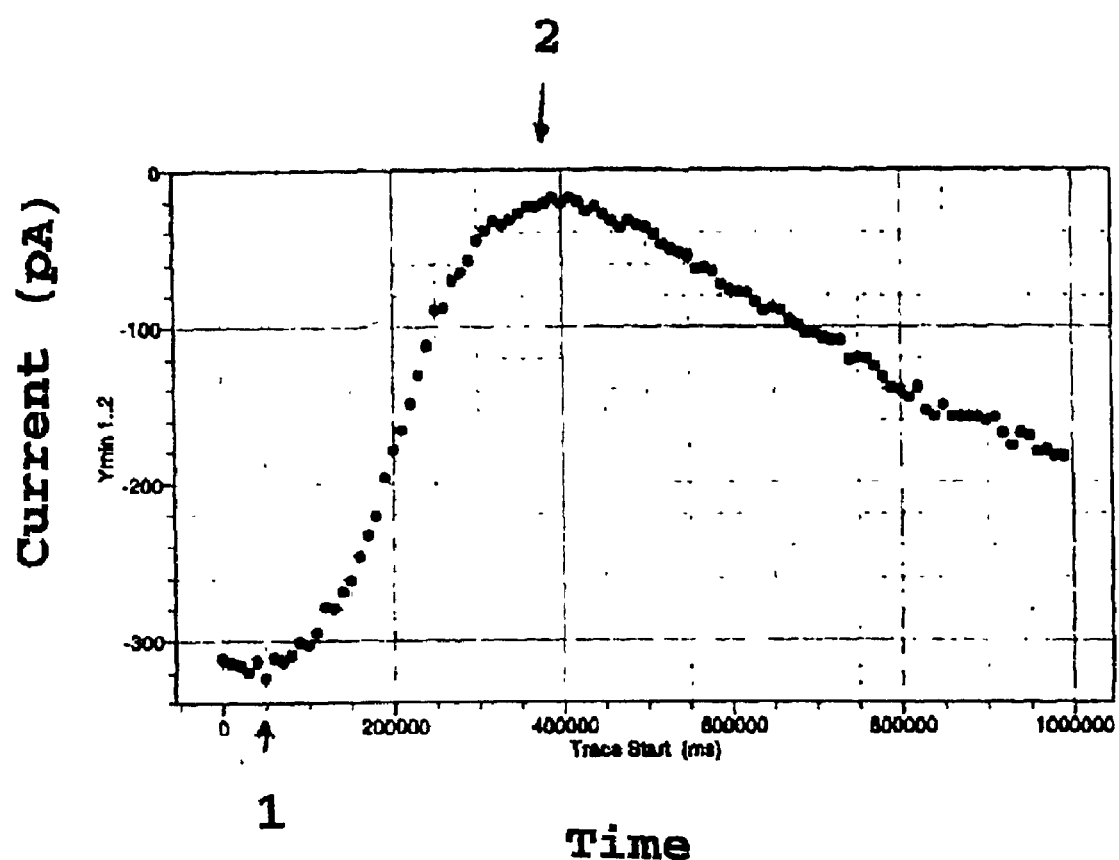

FIG. 42 graphically shows the ability of TH-1177 to inhibit calcium crossing the cell membrane of xenopus oocytes transfected with the alpha 1G subunit of a calcium channel. Point 1 signifies the time when 10 μM TH-1177 was added to the medium and Point 2 is a time when washout of TH-1177 occurs.

DETAILED DESCRIPTION OF THE PRESENT INVENTION

In the formula hereinabove, the term

refers to a cyclic ring containing 5–10 ring atoms and up to a total of 9 carbon atoms. The cyclic ring may be monocyclic or bicyclic, although it is preferred that it is monocyclic. The cyclic ring may contain up to 3 heteroatoms with the remaining ring atoms being carbon atoms. As used herein, the term heteroatom is O, S or N. Thus, the heterocyclic ring may contain 1–3 nitrogen atoms or one nitrogen atom and 1 or 2 sulfur or oxygen atoms. However, it is preferred that the heterocyclic ring contains 1 or 2 heteroatoms. Besides the nitrogen heteroatom, if a second or third ring heteroatom is present, it is preferred that it is either an oxygen ring atom or a nitrogen ring atom. It is especially preferred that the cyclic ring contains 1 heteroatom, i.e., X is N. It is preferred that the cyclic ring contains a total of 5 or 6 ring atoms and that it is monocyclic.

The cyclic ring is preferably saturated, although it may be partially unsaturated, i.e., it may contain one or two carbon double bonds. However, in a preferred embodiment, it does not contain any double bonds between the X atom and the adjacent ring atom. Preferred heterocyclic moieties include imidazolidinyl, imidazolinyl, pyrazolidinyl, pyrazolinyl, piperidyl, piperazinyl, morpholinyl and the like. Preferred heterocyclic rings are imidazolidinyl, piperidyl, piperazinyl and morpholinyl.

In the formula hereinabove, various substituents identified as $R_1$, $R_{11}$, $R_2$, $R_{10}$, and $R_6$ may be attached to the ring atom. As defined herein, the $R_1$ substituent is attached to the X ring atom; the other substituents are attached to the carbon atoms in the ring.

As used herein, the term "lower alkyl", refers to alkyl groups containing 1–6 carbon atoms, which may be straight-chained or branched. These groups include methyl, ethyl, propyl, isopropyl, butyl, isobutyl, tertiary butyl, sec-butyl, aryl pentyl, isopentyl, hexyl, and the like. It is preferred that alkyl contains 1–4 carbon atoms. The most preferred alkyl group is methyl.

The terms "electron withdrawing groups" and "electron donating groups" refer to the ability of a substituent to withdraw or donate electrons, respectively, relative to that of hydrogen if the hydrogen atom occupied the same position in the molecule. These terms are well understood by one skilled in the art and are discussed in *Advanced Organic Chemistry*, by J. March, 4th ed. John Wiley & Sons, New York, N.Y. pp. 16–18 (1992), and the discussion therein is incorporated by reference. Examples of electron withdrawing groups include halo, especially fluoro, bromo, chloro, iodo and the like, nitro, nitrile and the like. Examples of electron donating groups include such groups as hydroxy; lower alkoxy, including methoxy, ethoxy and the like; lower alkyl; amino; lower alkylamino; diloweralkylamino; and the like. One skilled in the art will appreciate that the aforesaid substituents may have electron donating properties under one set of circumstances and electron withdrawing properties under different chemical conditions or circumstances; these are also contemplated to be within the scope of these terms. Moreover, the present invention contemplates any combination of substituents selected from the above-identified terms.

As defined herein, the cyclic structure must contain either a Q or Q' substituent, as defined herein, or it may contain both Q and Q'.

Q and Q' may be the same or different and are defined as

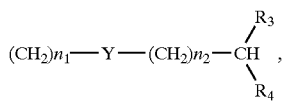

wherein $n_1$, Y, $n_2$, $R_3$ and $R_4$ are as defined herein. It is preferred that $n_2$ is O. Preferred values of $n_1$ are 1–4, but especially 1. It is also preferred that Y is $CH_2$ or O, especially O. The preferred values of $R_3$ and $R_4$ are independently aryl groups, which may be unsubstituted or substituted. The preferred aryl group is phenyl. It is preferred that the phenyl group be unsubstituted or substituted with halo, especially F, Cl or Br; lower alkoxy, e.g., methoxy; amino; nitro; nitrilo or lower alkyl.

$R_1$ as defined hereinabove has the formula:

$(CH_2)n$—Z—$R_5$, wherein n, Z and $R_5$ are as defined hereinabove.

The preferred value of Z is $CH_2$ or O.

It is preferred that n is 1–4, but especially, 1, 2 or 3.

The preferred $R_5$ is an aromatic ring, especially phenyl, which is either unsubstituted or substituted. If substituted, it is preferred that it is substituted with halo, alkoxy, alkyl, nitrilo, nitro or amino.

In one preferred embodiment of the present invention, the compound of the present invention has the formula:

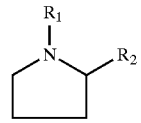

IA

It is even more preferred that the compound of Formula IA has the formula:

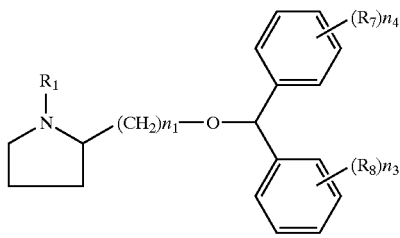

wherein $R_1$ and $n_1$ are as defined hereinabove and $R_7$ and $R_8$ are independently hydrogen, or an electron donating group or electron withdrawing group and $n_4$ and $n_3$ are independently 1–5.

Another preferred embodiment of the present invention is directed to compounds of the formula:

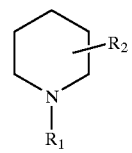

IB wherein $R_1$ and $R_2$ are as defined hereinabove.

Even more preferred embodiments of the compounds of Formula IB have the formulae:

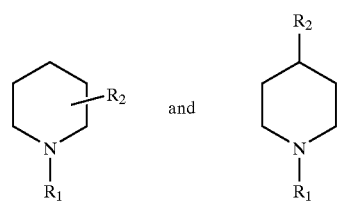

wherein $R_1$ and $R_2$ are as defined hereinabove.

Especially preferred embodiments of the compounds of Formula IB have the formula:

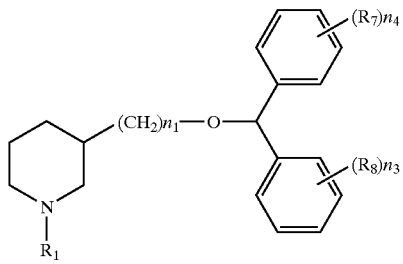

and

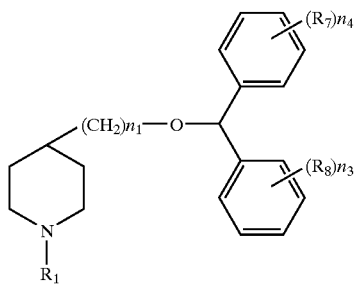

wherein $R_7$, $R_8$, $R_1$, $n_1$, $n_4$ and $n_3$ are as defined herein.

In the above formula, it is preferred that $R_1$ has the formula:

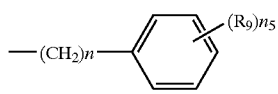

wherein $R_9$ is hydrogen, electron withdrawing group or electron donating group and $n_5$ is 1–5.

Another preferred embodiment has the formula:

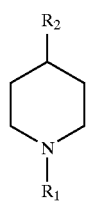

wherein $R_1$ is Q and $R_2$ is hydrogen or Q', as defined herein.

It is preferred that the compounds of the present invention be substantially pure, i.e., substantially free from impurities. It is most preferred that the compounds of the present invention be at least 75% pure (w/w) and more preferably greater than 90% pure (w/w) and most preferably greater than about 95% pure (w/w).

It is also preferred that the compounds of the present invention are enantiomerically pure, i.e., present in substantially one isomeric form, e.g., substantially the R (or D) stereoisomer or the corresponding S (or L) stereoisomer around the asymmetric carbon to which is attached the $R_2$ substituent. It is preferred that the stereochemistry at this carbon site is in the S (or L) configuration.

It is to be understood that all combinations and permutations of the various Markush groups for the different variables are contemplated to be within the scope of the present invention. In addition, the various stereoisomers generated therefrom are also contemplated to be within the scope of the present invention.

Preferred compounds of the present invention are listed on Page 14 herein.

The compounds of the present invention are prepared by art recognized techniques from commercially available starting materials. Exemplary procedures for making the compounds of the present invention are outlined hereinbelow.

For example, a compound of the formula II:

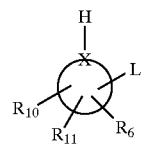

wherein

X is nitrogen reacts with $R_{20}$ COOH or an acylating derivative (e.g., lower alkyl ester) thereof under amide forming conditions to form the corresponding amide:

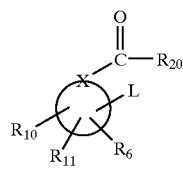

wherein $R_1$, $R_{10}$, $R_{11}$ and $R_6$ are as defined hereinabove

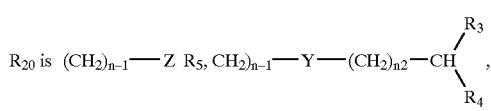

H, or lower alkyl, containing one less $CH_2$ group than the alkyl group of $R_1$, and L is a good leaving group, such as tosylate, mesylate, halide (e.g., chloride, bromide or iodide), and the like.

The product thereof is reacted with a carbonyl reducing agent, such as lithium aluminum hydride, in the presence of a Lewis acid, e.g., $AlCl_3$ to form the corresponding alkane. The product thereof is reacted with $R_2L_1$, under substitution reaction conditions, wherein $R_2$ is as defined hereinabove and $L_1$, is a good leaving group, e.g. halide, tosylate or mesylate to form the product of the present invention.

When Y in $R_2$ is O, and X is NH then the product is formed by a variation of the procedure described hereinabove. For example,

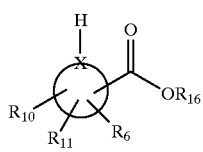

is reacted with $R_{20}$ COOH or acylating derivative under amide forming conditions to form a product of the formula:

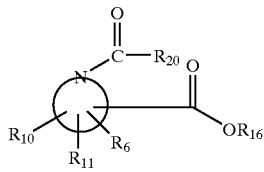

wherein $R_{16}$ is lower alkyl and $R_{20}$ is as defined hereinabove. When the above product is reacted with a reducing agent, such as lithium aluminum hydride, in the presence of a Lewis acid, such as $AlCl_3$, not only does this reagent reduce the corresponding amide but it also reduces the ester functionality to form the following compound:

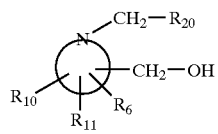

The corresponding alcohol is reacted with a molecule of the formula:

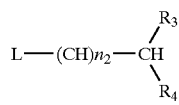

wherein L is a good leaving group, such as halide, tosylate, mesylate or the like in the presence of a strong base, such as hydroxide or when L is OH, in the presence of a catalytic acid e.g., paratoluenesulfonic base under Williamson reaction conditions to form the compounds of the present invention.

It is to be noted that in both syntheses $R_1$ is defined to include $CH_2$—$R_{20}$.

However, if $R_1$ is H, then the compound of Formula II is heated with $R_2L_1$ under nucleophilic reaction conditions, as described hereinabove, to form the product of Formula I.

If X is carbon, then the compound of Formula I may be formed by reacting a carbonyl compound of Formula III,

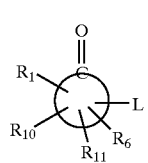

III with a Grignard reagent $R_1MgX_1$ under Grignard reaction conditions to form the corresponding alcohol of Formula IV,

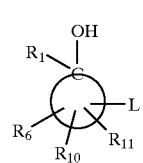

IV wherein $R_1$, $R_{10}$, $R_{11}$, $R_6$ and L are as defined hereinabove and $X_1$ is halide. It is to be noted that the carbonyl compound of Formula III is prepared from the corresponding alcohol by oxidizing the alcohol with an oxidizing agent known in the prior art such as $KMnO_4$, $CrO_3$, $K_2Cr_2O_7$ and the like under oxidizing conditions.

The OH functionality in Formula IV is converted to CH by techniques known in the art, such as, for example, by converting the alcohol to a tosylate or other sulfonates (e.g., mesylate) and then reacting the product thereof with a reducing agent such as $LiAlH_4$ or $NaBH_4$ and the like in a dipolar aprotic solvent, e.g., $Et_2O$, to form the corresponding alkane.

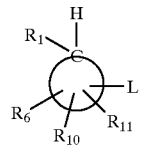

Then the product is reacted with $R_2L$, under substitution reaction conditions as described hereinabove to form the compound of the present invention.

If groups are present on the substituents $R_1$, $R_2$, $R_6$, $R_{10}$, or $R_{11}$, that are reactive with the reagents used, then prior to the reaction, they may be protected by reacting them with protecting groups known in the art. Examples of protecting groups are described in the book entitled "Protective Groups in Organic Synthesis", by Theodora W. Greene, John Wiley & Sons, New York, N.Y. 1981, the contents of which are incorporated by reference.

In the reactions described hereinabove, it is preferred that the reactions be conducted in solvents which are not reactive with the reactants or the products. In the amide forming reactions, it is preferred that the reaction be conducted in such solvents as methylene chloride, chloroform, and the like, while in the Grignard reactions and the reduction reactions, it is preferred that the reaction be conducted in ethers, such as diethyl ether, tetrahydrofuran and the like. The substitution and Williamson reactions are preferably conducted in inert solvents, such as hexane, pentanes, hexane, toluene, petroleum ether and the like. The reactions are conducted at temperatures effective to form the desired products in each step. Preferably these temperatures range from about 0° C. to refluxing temperatures of the solvent, depending on the particular reaction. A skilled artisan can easily determine the reaction conditions. However, for the Grignard reaction it is preferred that the reaction be conducted at near freezing temperatures (e.g., 0° C. or less), while in the substitution and the Williamson reactions, it is preferred that the reaction be conducted at refluxing temperatures.

The examples described hereinbelow provide exemplary procedures for preparing compounds of the present invention using the schematics described hereinabove.

The compounds of the present invention exhibit excellent cytostatic activity when administered in amounts ranging from about 0.5 mg to about 100 mg per kilogram of body weight per day. A preferred dosage regimen ranges from about 1 mg per kilogram per day to about 50 mg per kilogram per day. This dosage regime may be adjusted by the physician to provide the optimum therapeutic response. For example, several divided doses may be administered daily or the dose may be proportionally reduced as indicated by the exigencies of the therapeutic situation. A decided practical advantage is that the active compound may be administered in an convenient manner such as by the oral, intravenous (where water-soluble), intramuscular or subcutaneous routes.

The active compound may be orally administered, for example, with an inert diluent or with an assimilable edible carrier, or it may be enclosed in hard or soft shell gelatine capsules, or it may be compressed into tablets, or it may be incorporated directly into the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 3 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin.

The active compound may also be administered parenterally or intraperitioneally. Dispersions can also be prepared in glycerol, liquid polyethylene glycols, and mixture thereof and in oils. Under ordinary conditions of storage and use, these preparations contain a preservative to prevent the growth of microorganisms.

The pharmaceutical forms suitable for injectable use include sterile aqueous solutions (where water-soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parental compositions in dosage unit form for ease of administration and uniformity of dosage. Dosage unit form as used herein refers to physically discrete units suited as unitary dosages for the mammalian subjects to be treated, each unit containing a predetermined quantity of active material calculated to produce the desired therapeutic effect in association with the required pharmaceutical carrier. The specifics for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased conditions in which bodily health is impaired as herein disclosed in detail.

The principal active ingredient is compounded for convenient and effective administration in effective amounts with a suitable pharmaceutically acceptable carrier in dosage unit form as hereinbefore described. A unit dosage form can, for example, contain the principal active compound in amounts ranging from about 3 to about 1000 mg. Expressed in proportions, the active compound is generally present in from about 1 to about 750 mg/ml of carrier. In the case of compositions containing supplementary active ingredients, the dosages are determined by reference to the usual dose and manner of administration of the said ingredients.

Unless indicated to the contrary, percentages are by weight.

For a better understanding of the present invention reference is made to the following non-limiting description and examples.

General Methods

A. Synthesis of TH-1177. TH-1177 was synthesized in three simple steps (FIG. 1), Step 1 forms the amide, Step 2 is the reduction of the amide and Step 3 is the ether formation under Williamson ether formations.

Step 1: L-proline methyl ester was coupled with 4-methoxyphenylacetic acid using Benzotriazol-1-yloxytripyrrolidinephosphonium (PyBOP) and 2 equivalents of N-methylmorpholine to generate methyl 1-[2-(4-methoxyphenyl)acetyl]pyrrolidine-2-carboxylate, a yellowish oil.

Step 2: The resulting amide was subsequently reduced to the amino alcohol with LiAlH, and AlCl$_3$ in THF.

Step 3: The colorless oil was converted to its amine alcohol salt by dissolving the product of Step 2 in a small amount of ethyl acetate and adding 15% HClethyl acetate solution and evaporating the solvent using a rotary vacuum. The salt was coupled with 4-chlorobenzhydrol under Williamson conditions with catalytic para-toluene sulfonic acid in refluxing toluene. The final brownish oil was isolated by column chromatography on silica gel using a 50:50 mixture of ethyl acetate and hexane and confirmed by NMR and mass spectrometry. TH-1177 was dissolved in DMSO for use in vitro in ethanol for use in vivo.

With the exception of the last coupling, all steps provide yields of greater than 75%. PYBOP provides a safe and highly dependable method of forming amides by coupling a variety of amines and acids. It has proven superior to formation of acid halides or to the use of other coupling agents such as dicyclohexylcarbodiimide. Efficient reduction of both the amide and the ester is achieved in one step using LiAlH, and AlCl$_3$ in a 1:3 ratio. For the purity of the final product, it is important to have sufficient amount of hydride present to avoid formation of the aldehyde. Three different syntheses of TH-1177 were used for the completion of these studies, with no differences in NNR or mass spectroscopy characteristics among the batches. Each batch was assessed for its ability to inhibit PC3 and LNCaP prostate cancer cell proliferation in vitro (see Example 4) and the IC50 values for each batch were within the variance of the assay.

Figure 1:
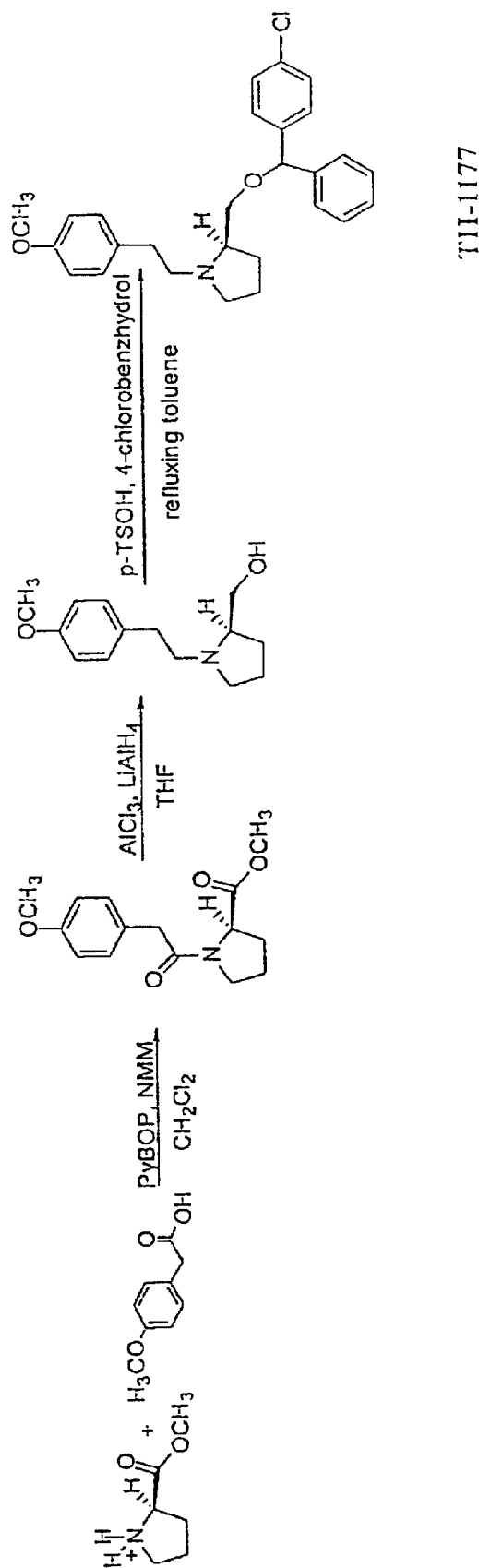
FIG. 1 depicts the chemical synthesis of TH-1177.

The three-step synthesis of TH-1177 FIG. 1) provides the sample outline of the synthesis that allows for large number of targets to be made easily and efficiently.

The other compounds listed hereinbelow are prepared by a variation of the above procedure. In all cases, Step 2 and Step 3 are very similar.

B. Synthesis of TH-1087

Step 1: Ethyl isonipecotate (1 equivalent) and 4-methoxyphenylacetic acid (1.2 equivalents) was reacted with 1 equivalent of benzotriazol-1-yl-oxytripyrrolidine phosphonium (PyBOP), and 1.2 equivalents of N-methyl morpholine (NMM) in methylene chloride and stirred at room temperature under an inert gas, such as nitrogen, for 30 minutes to an hour. The solvent was evaporated off.

Step 2: The product of Step 1 (1 equivalent) was reacted with 1 equivalent of LiAlH$_4$ and ⅓ equivalent of AlCl$_3$ (relative to LiAlH,). More specifically, to a round bottom flask equipped with stir bar and dry THF, AlCl$_3$ and LiAlH$_4$ were carefully added. The resulting solution was then allowed to stir for about 1 hour. The amide product of Step 1 was dissolved in a minimal amount of solvent (THF) and added to the stirring solution via a syringe very slowly to form the alcohol. After completion of the reaction, the THF was evaporated.

Step 3: The product of Step 2 was converted to the amino alcohol salt from the amino alcohol by dissolving the product of Step 2 in a small amount of ethyl acetate. 15% of HCl/ethyl acetate solution was added thereto. The salt was isolated by evaporating the solvent by rotary vacuum. To a round bottom flask equipped with stir bar and solvent the salt (1 equivalent) was added. To this was added 0.5 equivalents of p-TsOH and 1.1 equivalent of benzhydrol and the mixture was refluxed until completion. The product was isolated by column chromatography on silica gel using a 50:50 mixture of ethyl acetate and hexane.

C. TH-2029. The procedure in Example B was followed except that in Step 3,4-chlorobenzhydrol was utilized.

D. TH-2043. The procedure in Example B was followed, except that in Step 3, 4,4'-dichlorobenzhydrol was utilized.

E. TH-1203. The procedure in Example B was followed except in Step 1, ethyl nipecotate was utilized.

F. TH-1205. The procedure in Example C was followed, except in Step 3, 4-chlorobenzyhydrol was utilized.

G. TH-1019. The procedure in Example B was followed, except in Step 1, 3-(2-methoxyphenyl) propionic acid was utilized.

H. MMR-64. To a round bottom flask equipped with stir bar containing toluene; 5 equivalents of diphenylacetic acid was added followed by 5 equivalents of DMF. The solution was allowed to stir at 0° C. until the temperature had equilibrated. Upon reaching 0° C., the oxalyl chloride was added slowly, and the solution was allowed to warm to room temperature. It was stirred at room temperature for about 1 hour, upon which it was placed back onto ice (0° C.) and piperidine (1 equivalent) was slowly added. The reaction was allowed to warm to room temperature and was stirred until completion. The toluene was removed by rotary evaporation and the amide was isolated.

To a round bottom flask equipped with stir bar and dry THF, 1 equivalent of LiAPH$_4$ and ⅓ equivalents of AlCl$_3$ (relative to LiAlH$_4$) were added slowly. The resulting solution was allowed to stir for about 1 hour. The amide formed hereinabove (1 equivalent) was dissolved in a minimal amount of THF and added to the stirring solution via syringe very slowly.

I. MMR-70

Step 1: To a round bottom flask equipped with stir bar and toluene, 5 equivalents of diphenylacetic acid was added, followed by 5 equivalents of DMF. This solution was allowed to stir at 0° C. until the temperature had equilibrated. Upon reaching 0° C., the oxalyl chloride was added slowly and the solution was allowed to warm to room temperature. It was stirred at room temperature for about 1 hour, at which time it was placed back onto ice and ethyl isonipecotate (1 equivalent) was added slowly. After the addition of amine, the solution was then allowed to warm to room temperature as the reaction was stirred until completion.

Step 2: The procedure of Step 2 of B was followed.

Step 3: The procedure of Step 3 of B was followed.

J. MMR-92. The procedure of Example I was followed except in Step 3, 4-chlorobenzhydrol was utilized.

K. MR-100. The procedure of Example I was followed, except in Step 3, 4,4'-dichlorobenzhydrol was utilized.

L. MMR-104. The procedure of Example I was followed, except 9-fluorenol was utilized in Step 3.

M. M-TH-1113. The procedure of TH-1177 was followed, except that benzhydrol was utilized in Step 3.

N. TH-1211. The procedure of TH-1177 was followed, except that the D isomer of Proline Methyl ester hydrochloride was utilized in Step 1.

O. TH-2019. The procedure of TH-1177 was followed except that in Step 3, 4,4'-dichlorobenzhydrol was utilized.

P. TH-2129. The procedure of TH-1177 was followed, except that in Step 3, 4,4'dimethoxybenzhydrol was utilized.

Q. TH-2081. The procedure of TH-1177 was followed, except that 3-(4-methoxyphenyl) propionic acid was utilized in Step 1 and benzhydrol was utilized in Step 3.

R. TR-2085. The procedure of TH-2083 was followed except that in Step 3, 9-fluorenol was utilized.

S. TH-2151. The procedure for the synthesis of TH-2083 was followed except in Step 1, 3-(2-methoxyphenyl) propionic acid was utilized and in Step 3, 4-chlorobenzhydrol was utilized.

T. TH-2153. The procedure for the synthesis of TH-2151 was followed except in Step 3, 4,4'-dimethoxybenzhydrol was utilized.

U. TH-2209. The procedure for the synthesis of TH-1177 was followed except in Step 3, 4-bromobenzhydrol was utilized.

V. TH-2149. 2-(1-methylpyrrolidin-2-yl)-ethan-1-ol was dissolved in a small amount of ethyl acetate. To this was added a 15% HCl/ethyl acetate solution. The ethyl acetate was removed by rotary vacuum, thereby forming the amine salt. To this salt (1 equivalent) was added toluene, 0.5 equivalents paratoluenesulfonic acid and 1.1 equivalents of benzhydrol. The reaction was refluxed until completion.

W. TH 3101. The procedure for the synthesis of TH-1177 was followed except in Step 1, 4-methoxyphenylacetic acid was replaced with 4-fluorophenylacetic acid.

X. TH 3104. The procedure for the synthesis of TH-1177 was followed except 2-methoxyphenylacetic acid was used instead of 4-methoxyphenylacetic acid.

Y. TH 3105. The procedure for the synthesis of TH-1177 was followed except 3-methoxyphenylacetic acid was used instead of 4-methoxyphenylacetic acid.

The various products identified in A–Y are listed hereinbelow in Table 1:

TABLE 1

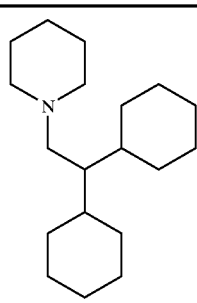

MMR-76

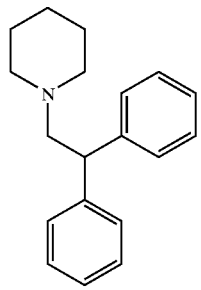

MMR-64

TABLE 1-continued

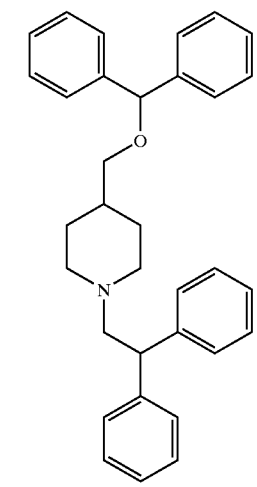

MMR-70

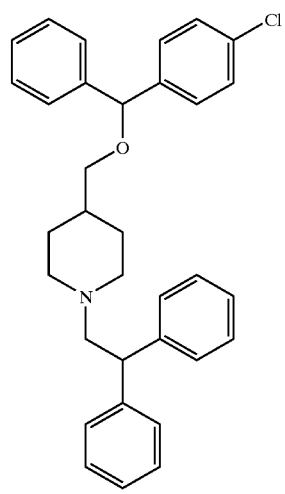

MMR-92

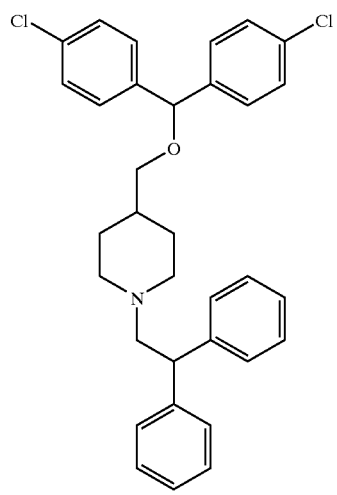

MMR-100

TABLE 1-continued
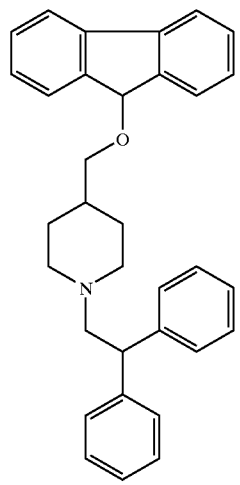
MMR-104
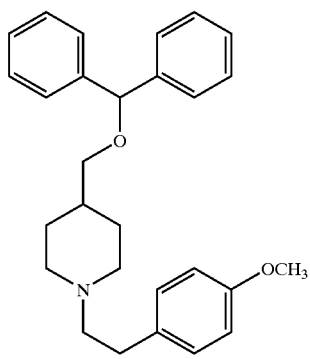
TM-1087
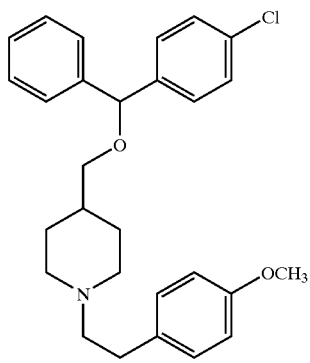
TM-2029
TABLE 1-continued
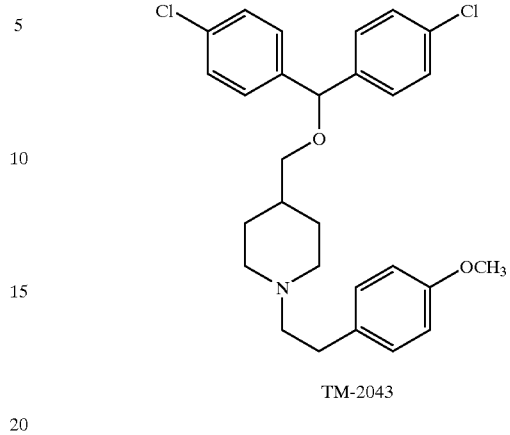
TM-2043
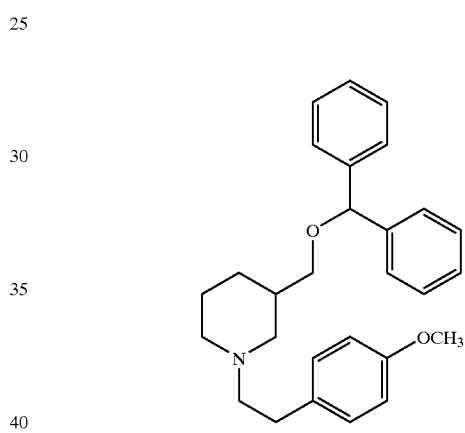
TM-1203
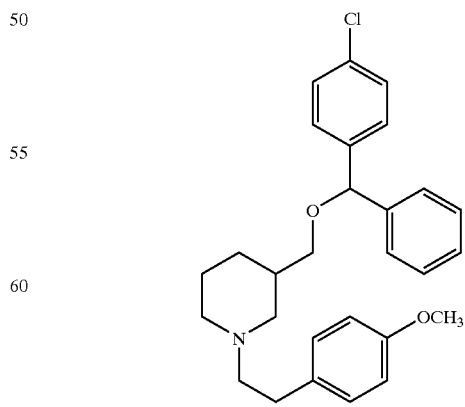
TM-1205

TABLE 1-continued
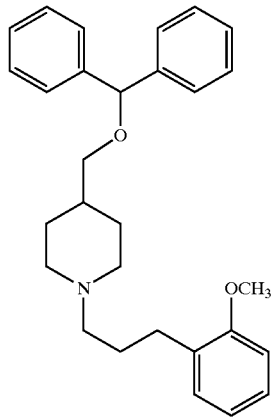
TM-1019
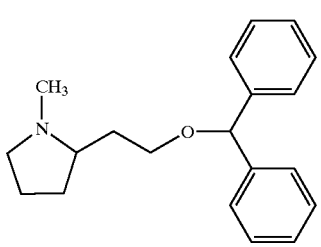
TM-2149
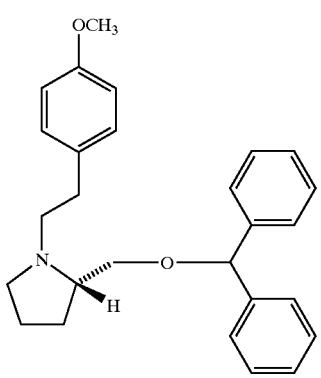
TM-1113
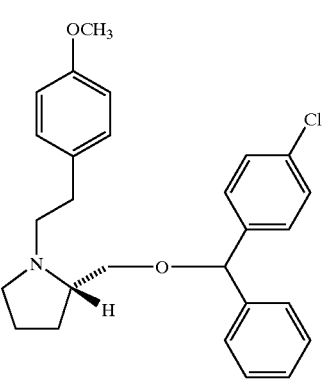
TM-1177
TABLE 1-continued
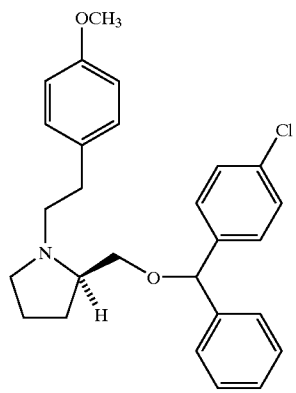
TM-1211
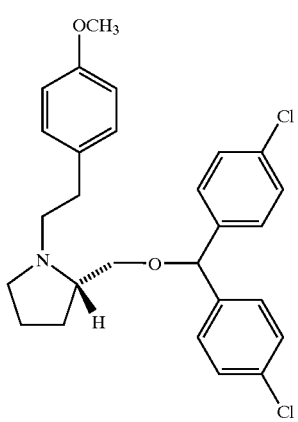
TM-2019
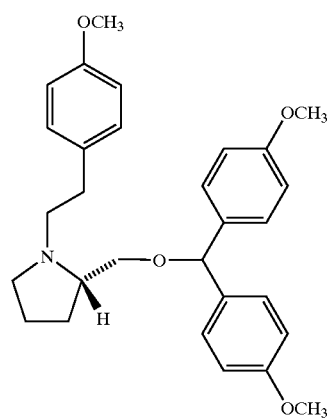
TM-2129

TABLE 1-continued
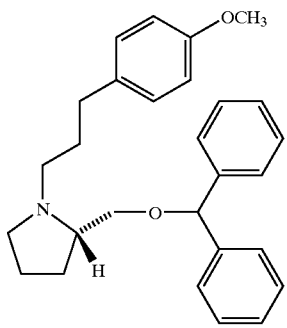
TM-2083
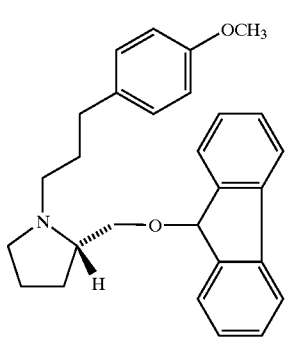
TM-2085
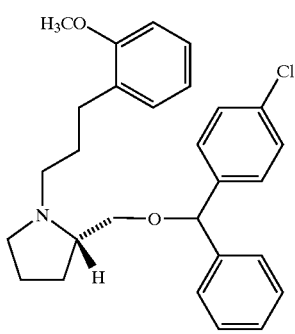
TM-2151
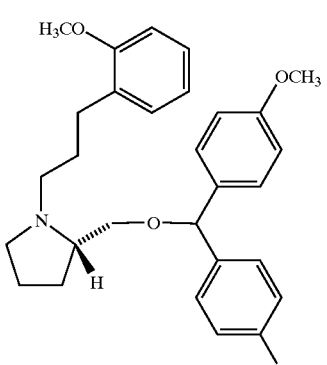
TM-2153
TABLE 1-continued
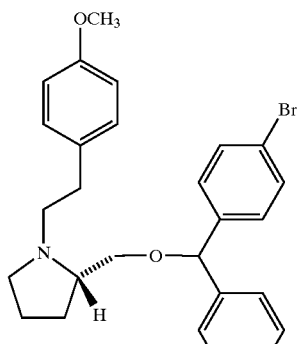
TM-2209
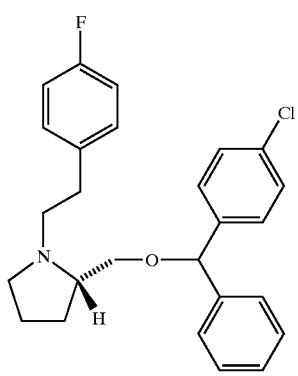
TM-3101
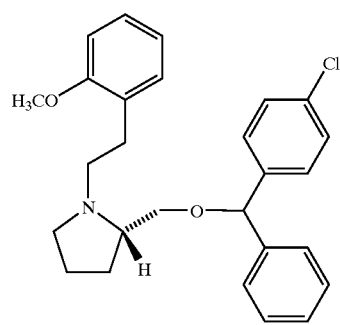
TM-3104
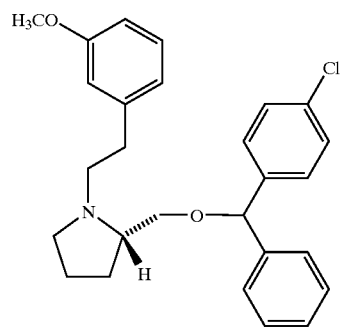
TM-3105
The compounds of the present invention are useful as anti-tumor agents. For example, compounds of the present invention are effective in treating malignant tumors, such as leukemia, especially lymphatic leukemia and solid tumors, for example, breast cancer, prostate cancer, ovarian cancer, pancreatic cancer, carcinomas, (e.g., adenocarcinomas,) melanomas, lymphomas, sarcomas (such as osteosarcomas), malignacies or tumors arising from tissue in lung, colon, liver, reproductive organs, (e.g., testes, uterus), skin, bone and connective tissue, central nervous system (CNS), e.g., brain, and peripheral nerve, including glia and Schwann cells, and the like.

Without wishing to be bound, it is believed that the compounds of the present invention are calcium channel blockers.

It is believed that an increase in intracellular concentration of calcium is provided in response to stimulation, such as by mitogens. As used herein, the term mitogen is an agent that causes cells to divide and multiply, i.e., a stimulant of mitosis. Examples of mitogens include growth stimulating factors, such as basic fibroblast growth factor (bFGF), epidermal growth factor (EGF), bradykinin, platelet derived growth factor (PDGF), and the like. Without wishing to be bound, it is believed that the growth stimulating factor engages with its receptor on the cell, which results through a cascade of reactions, in the production of inositol triphosphate (IP-3). Moreover, without wishing to be bound, it is believed that IP-3, binding to a specific intracellular receptor, induces the release of calcium from an intracellular storage pool, such as the endoplasmic reticulum, which in turn triggers influx of extracellular calcium into the cell.

It is believed that calcium entry is a critical signal for numerous cell processes, especially cellular activation and proliferation. The entry is controlled by membrane spanning pores known collectively as calcium channels. Opening of calcium channels allows calcium to follow its electrochemical gradient into the cytosol. These channels are classified by biophysical properties, such as conductance and mean open time and by relative sensitivity to various pharmacological agents.

There are various types of calcium channels that are known, such as L, N, P, Q, R, S and T. However, without wishing to be bound, it is believed that cancer cells possess calcium channels that have the properties similar to calcium channels in the T-family. Moreover, without wishing to be bound, it is also believed that cell proliferation associated with cancer is activated by calcium entry into the cytosol or cell interior through the calcium T-like channel.

As used herein the term T-like channel refers to a calcium channel that has the characteristics of a T-channel. However, unlike a true T-channel, the T-like channels are stimulated by a second messenger, such as calmodulin.

It is furthermore believed that the compounds of the present invention are primarily T-like calcium channel antagonists, that is, they retard and/or prevent the passage of calcium through the calcium T-like channels and entry thereof into the cell and as a result, are effective in retarding cellular proliferation. More specifically, it is believed that T-like calcium channels are found in electrically non-excitable cells, where calcium entry is believed to be conducted by non-voltage gated (NVG) channels. It is believed, without wishing to be bound, that cancer is associated with the entry of calcium through these type of channels to the cytosol and that the compounds of the present invention inhibit the passage of calcium through these types of T-channels, which conduct calcium entry by non-voltage gated channels, and thereby the compounds of the present invention inhibit unregulated proliferation of cancer cells.

Electrically non-excitable cells as used herein are any cells which are not electrically excitable, that is, cells which do not exhibit action potentials, such as occurs in neurons and muscle cells. In these cells, the calcium influx is not initiated by electrical action potential response at the plasma membrane. Electrically non-excitable cells contain the calcium T-like receptor operated calcium channels.

The compounds of the present invention are unlike most chemotherapeutic drugs. Most conventional cancer chemotherapeutic drugs are cytotoxic and exert their therapeutic benefit by killing cancer cells. On the other hand, the compounds of the present invention act by inhibition of calcium entry and arrest or retard cell proliferation controlling the growth of cancer cells and in this way renders the disease effectively impotent.

The present inventors have found that compounds which inhibit calcium entry and/or inhibit cellular proliferation in non-excitable cells are useful in treating cancer. Treating, as used herein means ameliorating a disease such that the condition of the patient improves or such that the progress of the disease is slowed.

Thus another embodiment of the present invention is directed to a method of treating cancer in an animal afflicted with such disease which comprises administering to said animal a calcium blocker that prevents and/or retards the entry of calcium ions across the cell membrane in the cancer cells in response to a mitogenic stimulus. The preferred calcium blocker is an organic compound that contains at least one carbon—carbon bond. It is therefore, preferably not an inorganic compound. The calcium blocker is present in amounts effective to retard the passage of extracellular calcium ions into the cells. The preferred effective amounts of the calcium blocker present are described hereinabove. The preferred calcium blocker contains a heterocyclic ring containing at least one nitrogen ring heteroatom. It is even more preferred that the cyclic ring contains 5–10 ring atoms and 1–3 heteroatoms, as long as at least one of the ring heteroatoms is nitrogen. It is especially preferred that the heterocyclic ring is saturated.

In a preferred embodiment, the calcium blocker inhibits or retards the entry of calcium ions to the cancer cell by blocking a calcium channel, such as the T-like calcium channel. Without wishing to be bound, it is believed that the calcium channel blocker inhibits or retards calcium entry into the cell by interacting with $\alpha 1$ subunits such as $\alpha 1G$ or $\alpha 1H$ subunits of the T-like calcium channel. The preferred calcium blockers are compounds of Formula I described hereinabove.

The effectiveness of various test compounds can be monitored by such tests, as described hereinbelow, which measure the calcium antagonist activity utilizing non-excitable cells or by monitoring the decrease in proliferation of cancer cells.

Suitable electrically non-excitable cells useful in accordance with these assays include any cell which requires the entry of calcium, for activation or proliferation, but which do not initiate entry of calcium by an electrical action potential such as occurs in neurons. Non-excitable cells include lymphocytes, and other formed elements of the blood epithelial cells, connective tissue cells and secretory cells including glandular cells. Particularly preferred electrically non-excitable cells for use in vivo assays include Jurkat cells (T-lymphocyte), MDA-468 (a breast cancer cell line), PC-3 (a prostate cell line) A-549 (a lung cancer cell line), HCT-116 (a colon cancer cell line), SK-OV3 (an ovarian cancel cell line), MIA PaCa-2, (a pancreatic cell line), and any other cell type or cell line which is electrically non-excitable. The cell lines mentioned above are available from the American Type Culture Collection, Manassas, Va.

The cell lines used in the assays described hereinbelow were maintained and remained viable using standard techniques known in the art. For example, for hormone-resistant LNCaP-FRG and hormone sensitive PC3 prostate cancer, cells which were obtained from the ATCC (Manassas, Va.), were maintained in RPMI 1640, supplemented with glutamine and 5% fetal bovine serum containing Serxtend (Irvine Scientific). The fetal bovine serum used for culture was heat inactivated by maintaining the serum at 56° C. for 1 hr.

Although various assays are known in the art, the present inventors have utilized the following assays.

Measurement of Intracellular $Ca^{2+}$ Concentration:
Cells were incubated in growth media containing 1 $\mu$M of the acetoxy-methyl ester of the $Ca^{2+}$-sensitive fluorescent dye indo-1 (indo-1/AM, Molecular Probes, Eugene, Oreg.) for 1 hour at 37° C. Cells were washed three times in buffer A (10 mM HEPES, pH 7.4, 1 mM $MgCl_2$, 3 mM KCl, 1 mM $CaCl_2$, 140 mM NaCl, 0.1% glucose, 1% fetal bovine serum) and suspended to a final concentration of $10^6$/ml. Prior to stimulation, cells were warmed to 37° C. Prior to stimulation, cells were also incubated with drug, calcium channel antagonists and the $IC_{50}$ values were determined. Changes in $[Ca^{2+}]$ were monitored in an SLM 8100C spectrofluorometer (SLM/Aminco, Urbana, Ill.) using previously published methods, Haverstick, et al. (1998) *Cell Calcium*, 23: 361–368; Densmore, et al. (1996) *Am. J. Physiol.*, 271:C1494–1503, incorporated herein by reference.

Calcium influx into the cell is suitably stimulated using either (1) a physiological ligand or (2) an endoplasmic reticulum (ER) ATPase inhibitor. Preferably, a physiological ligand is used to stimulate calcium influx into the cell.

A physiological ligand as used herein is a ligand which binds to a receptor on a non-electrically excitable cell and stimulates $Ca^{2+}$ influx into the cell. Depending on the non-electrically excitable cell used, these ligands will vary. For example, suitable ligands for use with Jurkat cells include antibodies to the T-like cell receptor for antigen, e.g., OKT3. Suitable ligands for use with MDA 468 cells include epidermal growth factor or transforming growth factor. Suitable ligands for use with PC-3 cells include epidermal growth factor or purinergic agonists such as adenosine. These are reviewed in Carpenter and Cohen, 1990, *J. Biol. Chem.* 265: 7709–7712; Crabtree and Clipstone, 1994. *Annu. Rev. Biochem.* 63: 1045–1083; and Gardner, P. 1989. Cell, 59:15–20 incorporated herein by reference. These reagents are available from several suppliers such as Sigma, CALBIOCHEM and Research Diagnostics (Flanders, N.Y.).

Endoplasmic Reticulum (ER) ATPase inhibitor, as used herein, is any compound which stimulates the release of calcium from the endoplasmic reticulum into the cytoplasm, which, in turn, activates calmodulin, which, in turn, activates calcium entry into the cell (for review of ER ATPase inhibitors, see Thastrup, O, Agents and Actions (1990), 29:8–15; Inesi and Sagara, Archives of Biochem. and Biophys., 298:313–7 and Darby, et al., Biological Signals (1993), 2:293–304). Preferred ER ATPase inhibitors include cyclopiazonic acid (available from Sigma, St. Louis, Mo.) and thapsigargin (available from Sigma).

Measurement of cellular proliferation: LNCaP cells at $2.5 \times 10^4$/well or PC3 cells at $5 \times 10^4$/well, both in a final volume of 100 $\mu$l, were plated in triplicate in standard flat bottom 96 well tissue culture plates in the presence of drug or vehicle (DMSO). Unless otherwise indicated, cells were grown for 48 hours at 37° C. in a $CO_2$ incubator. Relative cell growth was determined with the CellTiter 96 aqueous cell proliferation assay (Promega, Madison, Wis.) as described by the manufacturer using an automated plate reader. Results were calculated in a blinded fashion and are means of triplicate determinations.

For the 48 hour proliferation, cells were cultured with calcium channel antagonists or without calcium channel antagonists. The $IC_{50}$ values of the calcium channel antagonists were determined. The present inventors have found that compounds which have an $IC_{50}$ value less than about 10 $\mu$m and more preferably less than 5 $\mu$M and most preferably less than 2 $\mu$M with respect to the breast cancer cell lines, prostate cancer cell lines and lymphocytic leukemia cell lines in either or both of the above-identified assays are effective in treating cancer in patients, including mammals and especially humans. In addition, preferred compounds do not possess an imidazole moiety. The present inventory: have found that compounds of the present invention have efficacy of this magnitude in these cell lines.

For the other cell lines of solid tumors, such as pancreatic tumor cell lines, ovarian tumor cell lines, lung tumor cell lines, the present inventors have found that compounds which exhibit $IC_{50}$ of less than about 30 $\mu$M and more preferably less than about 20 $\mu$M and most preferably less than about 10 $\mu$M in either or both of the aforementioned assays are effective in treating cancer in patients, including mammals, and especially humans. Again, the inventors have found that compounds of the present invention exhibit efficacy of this magnitude in these cell lines.

In many of the experiments described below, in vivo assays were also performed.

Animal Studies: All protocols were approved by the Animal Care Committee of the University of Virginia. SCID mice were housed in a barrier isolation facility of the University of Virginia Department of Comparative Medicine and all personnel observed sterile techniques when entering the facility and handling animals. TH-1177 was dissolved in ethanol and diluted 10-fold in sterile phosphate buffered saline (PBS) immediately prior to each day's injection. Injection volumes of 0.5 ml per animal were used. Vehicle consisted of PBS diluted ethanol. PC3 cells for injection were prepared by washing in sterile PBS three times prior to suspension to $2 \times 10^6$ per ml. Each animal received 0.5 ml of cells by IP injection on day zero of the experiment shown in FIG. 9. Each animal received a daily IP injection of vehicle or drug beginning on day 1.

Statistical methods: In vivo survival data were analyzed with Prism 2.01 (GraphPad Software, San Diego, Calif.). The results of the Kaplan-Meier analysis are presented as one-tailed probabilities because there was no reasonable expectation that drug treatment would cause the mice to succumb more rapidly to the implanted cancer than would control animals.

EXAMPLE 1

TH-1177 blocked capacitative $Ca^{2+}$ entry in human prostate cancer cells. In electrically non-excitable cells, $Ca^{2+}$ influx is triggered by release of $Ca^{2+}$ from its internal storage depot by a phenomenon that has been called "capacitative" $Ca^{2+}$ entry (Putney, J. W., Jr. (1986) *Cell Calcium*, 7:1–12; Haverstick, et al. (1993) *Mol. Biol. Cell*, 4: 173–184; Kohn, et al. *Proc. Natl. Acad. Sci. USA*, 92: 1307–1311, incorporated herein by reference). Capacitative entry can be initiated by treatment of cells with thapsigargin. Thapsigargin inhibits the $Ca^{2+}$-ATPase of the endoplasmic reticulum allowing uncompensated leak of $Ca^{2+}$ from this compartment into the cytosol thereby causing $Ca^{2+}$ entry in the absence of engagement of a specific receptor. (Thastrup, et al. (1990) *Proc. Natl. Acad. Sci. USA,* 87: 2466–2470; Takemura, et al. (1989) *J. Biol. Chem.* 264: 12266–12271, incorporated herein by reference).

Figure 2:
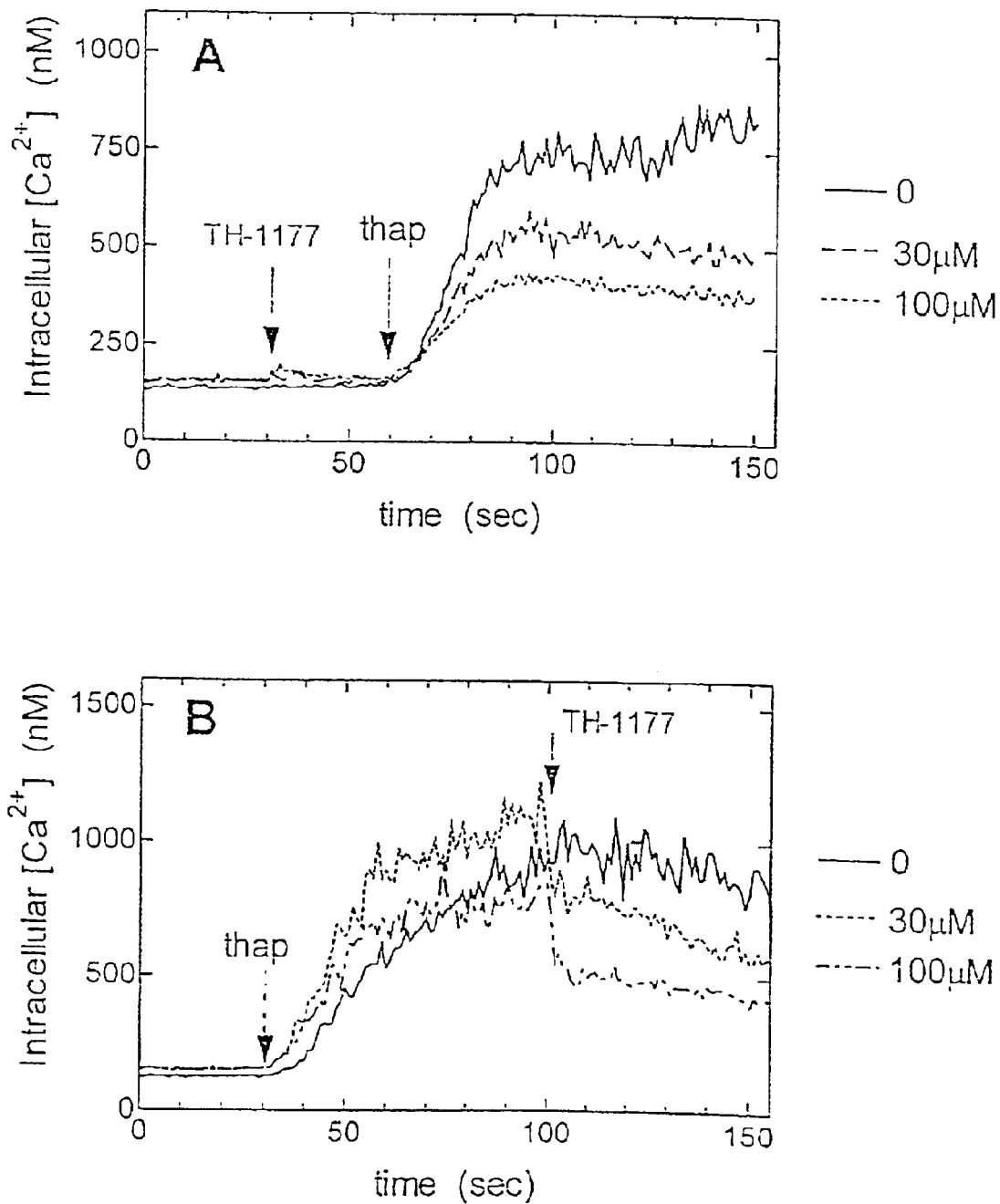
FIG. 2 graphically illustrates the effect of 2+TH-1177 on $Ca^{2+}$ entry stimulated by thapsigargin in LNCaP cells. LNCaP cells were stimulated with 300 nM thapsigargin to initiate $Ca^{2+}$ entry in a receptor independent manner. The indicated concentrations of TH-1177 were added prior to stimulation with thapsigargin (panel A) or after the influx pathway had been opened (panel B).

Ns shown in FIG. 2A, addition of TH-1177 to a suspension of LNCaP human prostate cancer cells before thapsigargin resulted in a dose dependent inhibition of the increase in $[Ca^{2+}]_i$. TH-1177 also reduced the increase in $[Ca^{2+}]_i$ initiated by thapsigargin when added after the stimulus (FIG. 2B). The elevated $[Ca^{2+}]_i$ seen at 100 s in FIG. 2B was attributable to $Ca^{2+}$ entry alone. Therefore, the effect of TH-1177 was mediated by inhibition of $Ca^{2+}$ entry.

EXAMPLE 2

TH-1177 Inhibited Receptor-Linked $Ca^{2+}$ Entry.

The P2 purinergic receptor is linked to activation of the $Ca^{2+}$ entry pathway in many types of cells including prostate cancer cells (Fang, et al. (1992) *J. Clin. Invest.* 89: 191–196). The ability of TH-1177 to block capacitative $Ca^{2+}$ entry induced by thapsigargin indicated that this compound block $Ca^{2+}$ entry triggered by the engagement of a specific receptor. The P2 receptor binds extracellular ATP inducing multiple biochemical events including $Ca^{2+}$ entry (Fang, et al. supra). Addition of ATP to LNCaP prostate cancer cells resulted in a rapid rise in $[Ca^{2+}]_i$, that was inhibited by the prior addition of TH-1177 (FIG. 3A). As shown in FIG. 3B, TH-1177 added after ATP also caused a reduction in the $[Ca^{2+}]_i$ that had been augmented by P2 receptor engagement.

Figure 3:
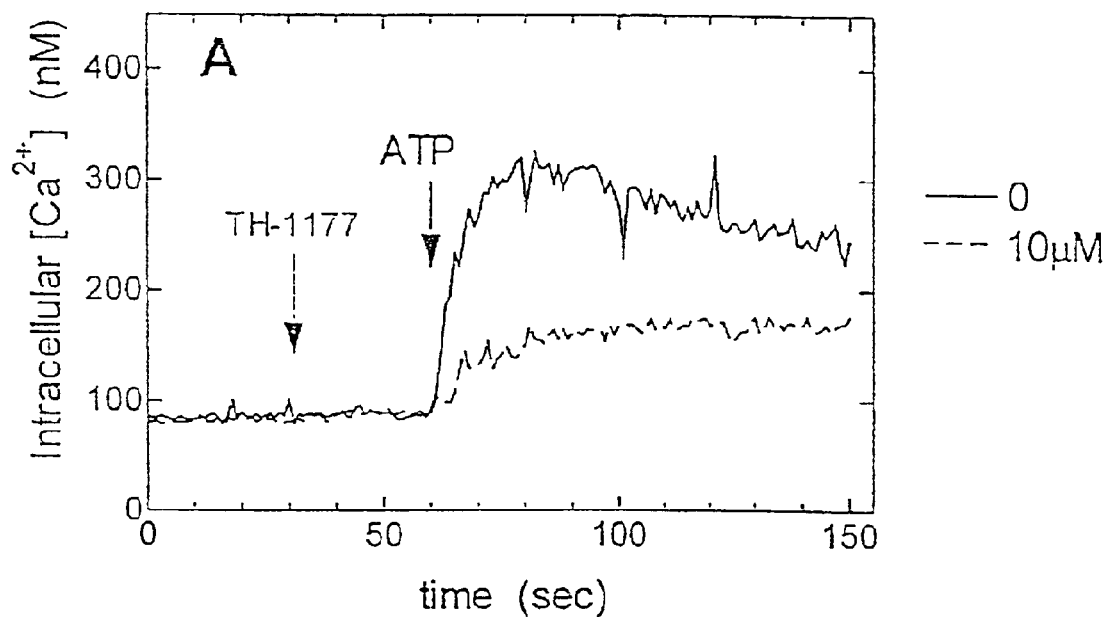
FIG. 3 graphically illustrates the effect of TH-1177 on $Ca^{2+}$ entry stimulated by ATP in LNCaP cells. The effect of 10 $\mu$M TH-1177 on $Ca^{2+}$ entry stimulated in a receptor dependent manner by 1 mM ATP was examined with TH-1177 added prior to stimulation with ATP (panel A) or after the influx pathway had been opened (panel B).
Figure 3:
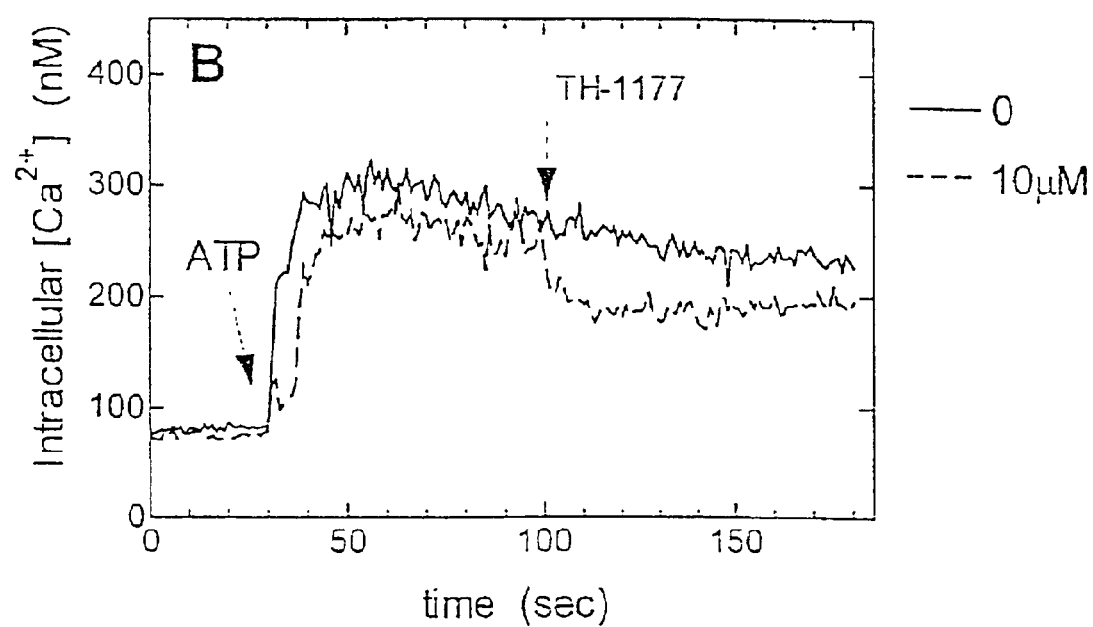

PC3 prostate cancer cells also demonstrated an increase in $[Ca^{2+}]_i$ when stimulated by ATP (FIG. 3). Ir. the experiment depicted in FIG. 4A, TH-1177 was added before the cells were stimulated with ATP. TH-1177 caused a concentration dependent inhibition of the increase in $[Ca^{2+}]_i$ that was otherwise induced by engagement of the purinergic receptor. By 70 s after ATP addition, release of $Ca^{2+}$ from the internal storage pool was largely over (for example, see FIG. 5 below) and the maintenance of elevations of $[Ca^{2+}]_i$ over baseline was dependent on Ca entry from the extracellular compartment. As shown in FIG. 4B, addition of TH-1177 to cells previously treated with ATP caused a reduction in $[Ca^{2+}]_i$. Therefore, TH-1177 interacts with the $Ca^{2+}$ influx pathway.

The efficiency of TH-1177 at blocking $Ca^{2+}$ entry was assessed by comparison to the effect of chelation of extracellular $Ca^{2+}$ with EGTA, which was considered 100% inhibition of $Ca^{2+}$ entry. For LNCaP cells, the $IC_{50}$ for TH-1177 was 3 µM and for PC3 cells, the $IC_{50}$ was 16 µM under these conditions.

Figure 4:
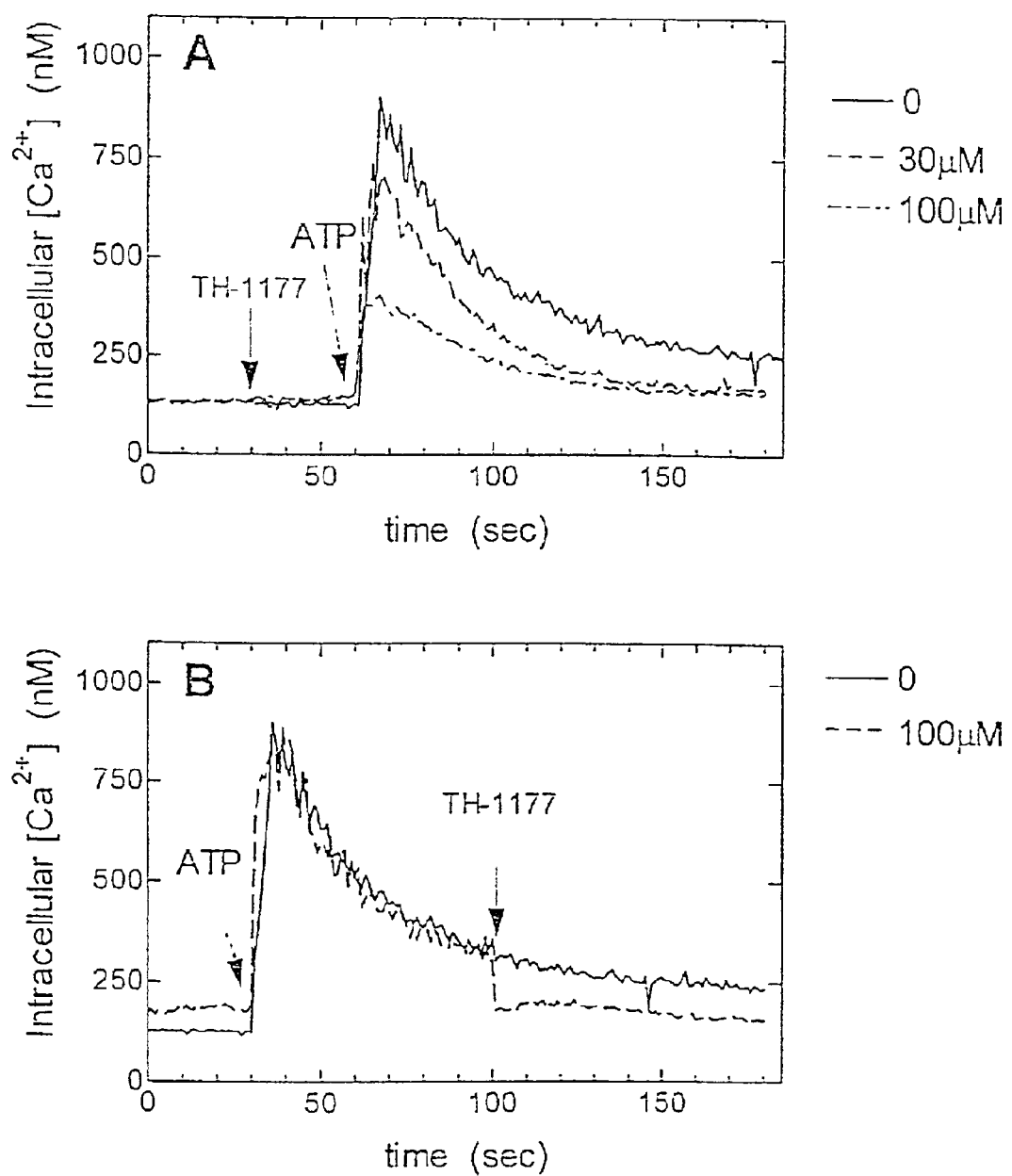
FIG. 4 graphically illustrates the effect of TH-1177 on $Ca^{2+}$ entry stimulated by ATP in PC3 cells. The effect of the indicated concentrations of TH-1177 on $Ca^{2+}$, entry stimulated in a receptor dependent manner by 1 mM ATP was examined with TH-1177 added prior to stimulation with ATP (panel A) or after the influx pathway had been opened (panel B).
Figure 5:
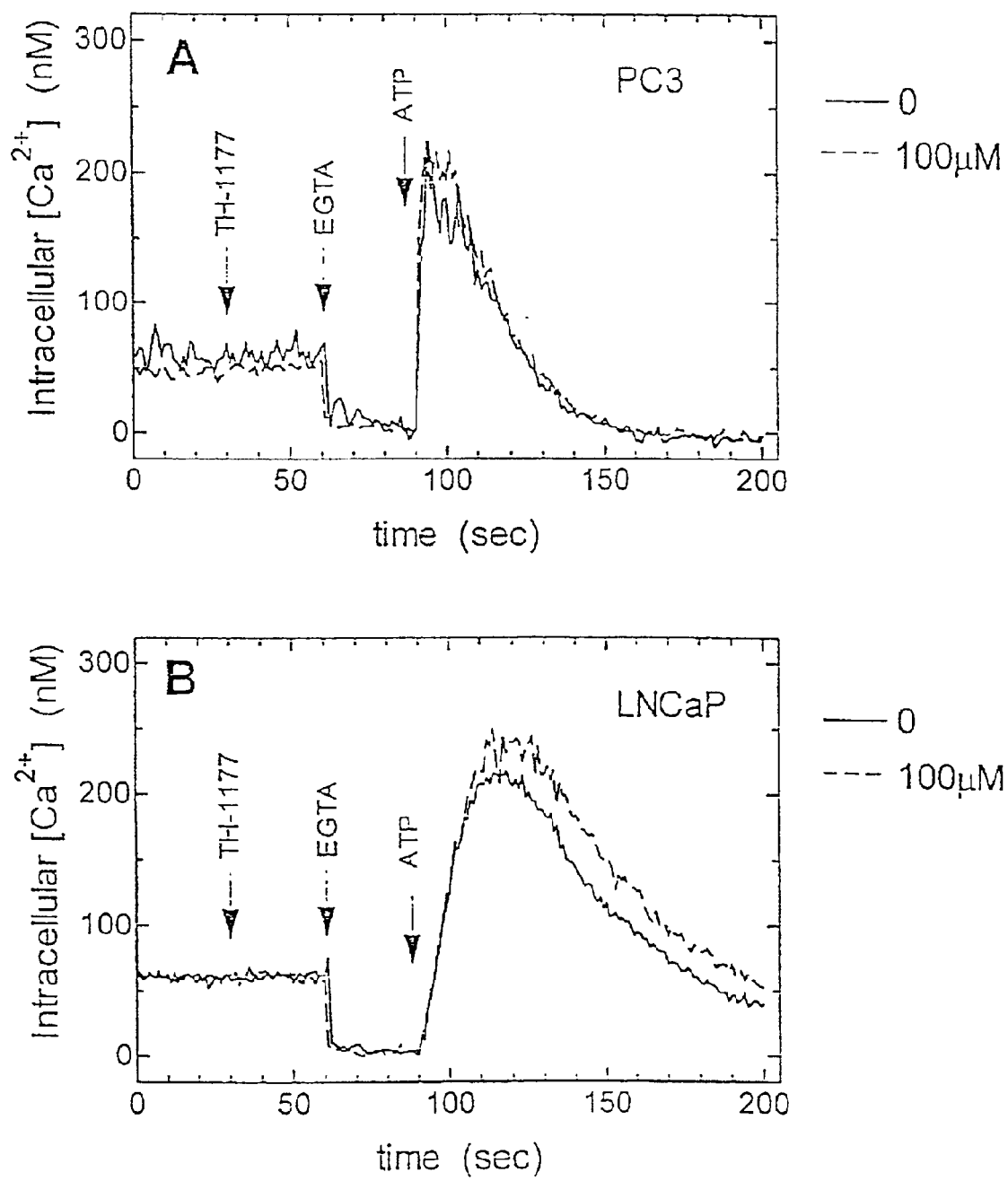
FIG. 5 graphically illustrates the effect of TH-1177 on release of $Ca^{2+}$ from the internal storage depot. The effect of TH-1177 on IP3 mediated release of $Ca^{2+}$ from the internal storage pool was monitored by chelating extracellular $Ca^{2+}$ with the addition of EGTA to uncover the release component. The indicated concentrations of TH-1177 were added at 30s, followed by 2.5 mM EGTA at 60s and receptor stimulation with 1 mM ATP at 90s. Panel A: PC3 cells. Panel B: LNCaP cells.

The data presented above provide that TH-1177 inhibited the stimulated increase in $[Ca^{2+}]_i$ by blockage of $Ca^{2+}$ entry. In FIG. 5, extracellular $Ca^{2+}$ was markedly reduced by addition of EGTA to the extracellular medium. Under these conditions, addition of ATP to either PC3 (FIG. 5A) or LNCaP (FIG. 5B) cells resulted in a rise in $[Ca^{2+}]_i$ that was more transient and of smaller magnitude than in the presence of extracellular $Ca^2$. This increase represented release of $Ca^{2+}$ from the internal storage pool. Addition of TH-1177 had no effect on the size of this change in $[Ca^{2+}]_i$. This indicated that TH-1177 did not interfere with $Ca^{2+}$ release and suggested that TH-1177 had no influence on the biochemical events upstream from release of $Ca^{2+}$ from the internal pool. The inhibition of increases in $[Ca^{2+}]_i$ caused by TH-1177 in the presence of extracellular $Ca^{2+}$ was due to blockage of the $Ca^2$ entry pathway that can be opened by engagement of the P2 purinergic receptor (FIGS. 3 and 4).

EXAMPLE 3

TH-1177 Inhibited Prostate Cancer Cell Proliferation in vitro by a Cytostatic Mechanism.

Inhibition of $Ca^{2+}$ entry has been shown to limit proliferation of cancer cells in vitro. The ability of TH-1177 to block $Ca^{2+}$ entry induced by release of $Ca^{2'}$ from internal stores such as that stimulated by engagement of the P2 purinergic receptor suggested the possibility that this agent could inhibit proliferation of prostate cancer cells in vitro.

Figure 6:
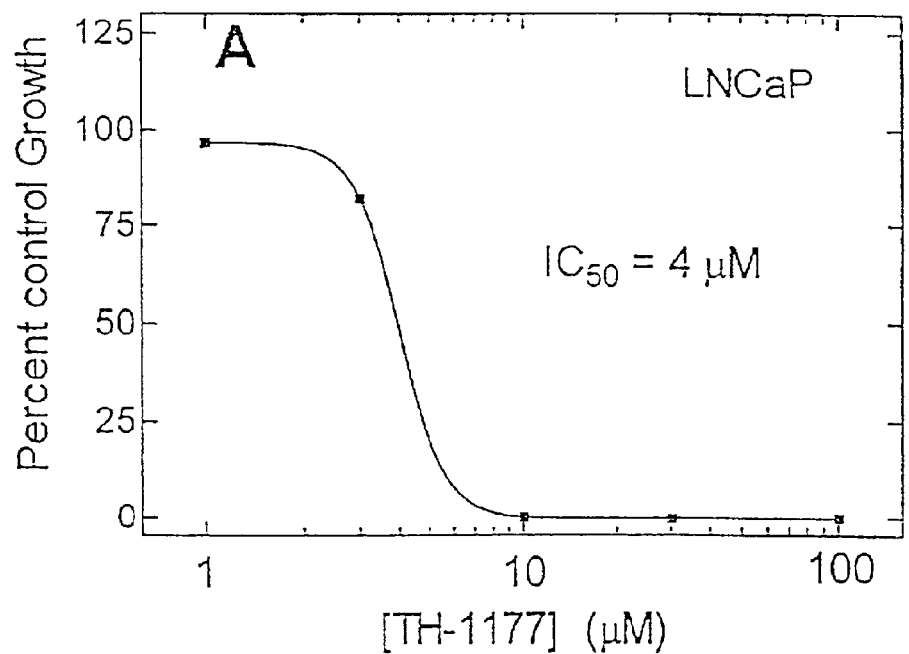
FIG. 6 graphically illustrates the effect of TH-1177 on cellular proliferation. LNCaP cells (panel A) at $2.5\times10^4$ cells in a dilution of 100:1 or PC3 cells (panel B) at $5\times10^4$ cells in a dilution of 100:1 were grown for 48 hours in the absence (100% cell growth) or presence of the indicated concentrations of TH-1177. Results are the mean of 4 determinations.
Figure 6:
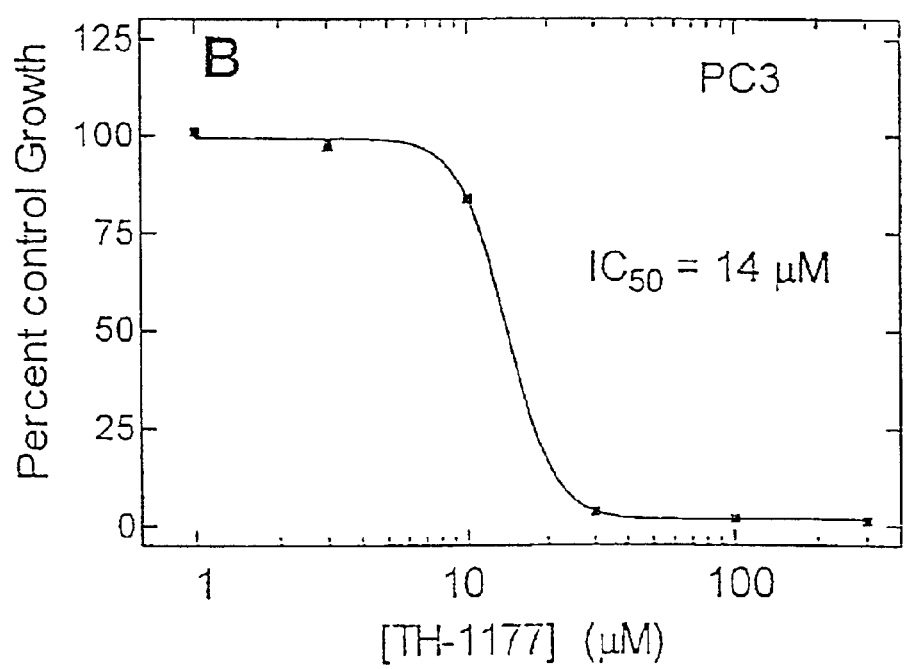

As shown in FIG. 6, TH-1177 caused a concentration dependent inhibition of the proliferation of both LNCaP and PC3 cells. The $IC_{50}$ for inhibition of LNCaP proliferation was 4 µM (FIG. 6A) while the value for PC3 prostate cancer cells was 14 µM (FIG. 6B). When compared to the $IC_{50}$ values for inhibition of $Ca^{2+}$ entry of 3 µM and 16 µM for LNCaP and PC3 cells, respectively, it was clear that TH-1177 inhibited proliferation at a concentration that was similar to that which was needed to block $Ca^{2+}$ entry in these two cell types.

Figure 7:
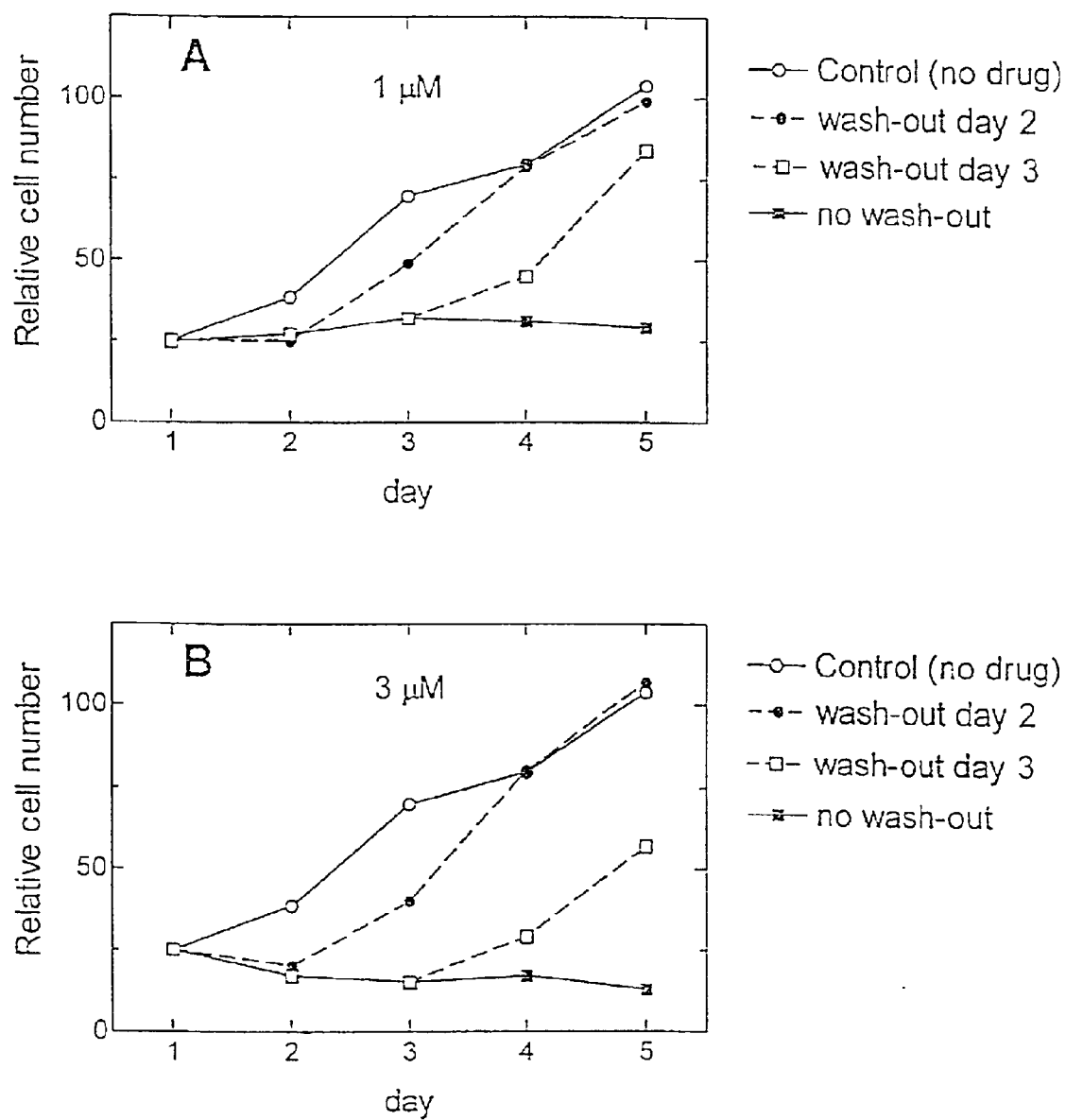
In FIG. 7, LNCaP cells were plated at $2.5\times10^5$ cells per ml in the absence of drug or with 1 $\mu$M (panel A) or 3 $\mu$M (panel B) TH-1177 on day 1 in triplicate flasks and the number of viable cells determined in each flask on days 2 through 5. On days, 2, 3, and 4, all flasks were centrifuged and fresh media added with or without TH-1177 as indicated. The effect on cell growth in each circumstance is graphically depicted.

Most conventional cancer chemotherapeutic drugs are cytotoxic and exert their therapeutic benefit by killing cancer cells. On the other hand, agents that act by inhibition of $Ca^{2+}$ entry (i.e. cytostatic agents) would likely arrest cell proliferation rather than induce cell death Meldolesi, J. (1995) *Nat. Med.,* 1:512–513. To address this possibility, LNCaP (FIG. 7) prostate cancer cells were allowed to grow unimpeded or exposed to TH-1177 for 2 or 3 days before the agent was washed away. Both cell lines grew in the absence of TH-1177 while growth was stopped when the compound was present. Removal of TH-1177 after exposure for 2 or 3 days was associated with resumption of a rate of growth that was similar to that seen with cells never exposed to TH-1177 (FIG. 7). Similar results were seen with PC3 prostate cancer cells. Therefore, prostate cancer cells were quiescent in the presence of TH-1177 relative to cells that were cultured in the absence of this agent.

Figure 8:
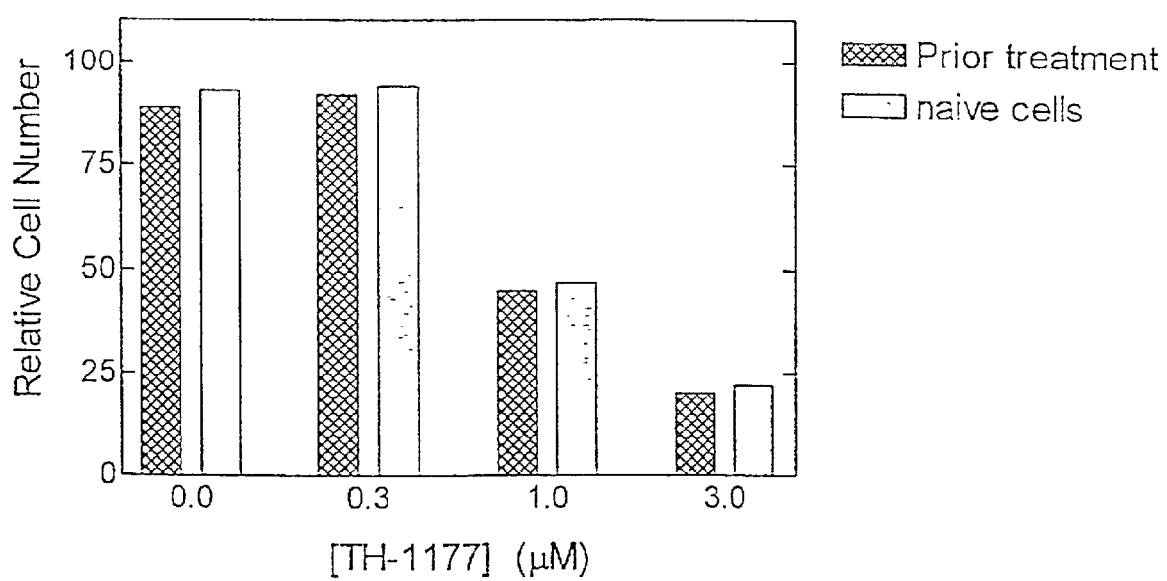
In FIG. 8, LNCaP cells were grown in the absence (naive cells) or presence (prior treatment) of the indicated concentrations of TH-1177 for 48 hours. The media was removed and drug-free media was added for 48 hours. The drug-free media was then removed and media containing drug was added to all cells for 72 hours. The data, shown graphically, indicate the relative number of cells at the end of this process.

The experiment depicted in FIG. 7 demonstrated that TH-1177 did not induce any long-lasting alteration in the proliferative phenotype of prostate cancer cells. The experiment depicted in FIG. 8 was performed to further evaluate this possibility.

LNCaP cells were grown in the continuous presence of TH-1177 at one of three concentrations or in the compound's absence for 4 hr. The cell culture medium was then replaced with medium free of TH-1177 and maintained for an additional 48 hr. TH-1177 was then added to all cell cultures at the concentrations indicated in FIG. 8 such that previously treated cell cultures received an identical second treatment. Prior treatment with TH-1177 had no effect on the response to the second exposure of this compound (FIG. 7). This observation demonstrated that TH-1177 was present in order to inhibit proliferation and that TH-1177 did not alter the drug-sensitive phenotype of these human prostate cancer cell lines.

EXAMPLE 4

Inhibition of Lymphocyte Prostate and Breast Cancer Cell Proliferation in vitro.

As shown in FIGS. 10–29, TH-1087, TH-1113, TH-1211, and TH-1205 caused concentration dependent inhibition of the proliferation of Jurkat, PC3, LNCaP, MDA-468 and MDA-361 cells.

As shown in FIGS. 30–39, MMR-64, MMR-70 caused inhibition of the proliferation of Jrurkat, PC3, L-NCaP, MDA-468 and MDA-361 cells.

EXAMPLE 5

Figure 9:
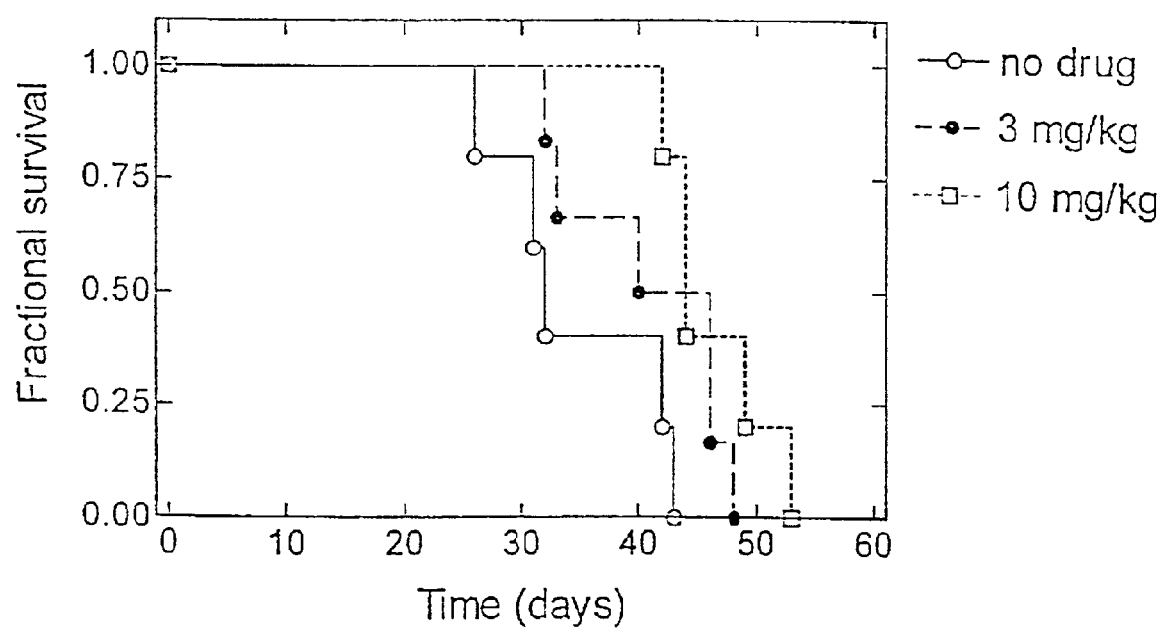
FIG. 9 tabulates and graphically illustrates results of animal trials with TH-1177. SCID mice were inoculated with $1\times10^6$ PC3 cells on day 1. Mice received daily injections of vehicle (no drug, open circles) or TH-1177 at 3 mg/kg (closed circles) or 10 mg/kg (open squares). The survival curve for this group of animals is shown.
Figure 10:
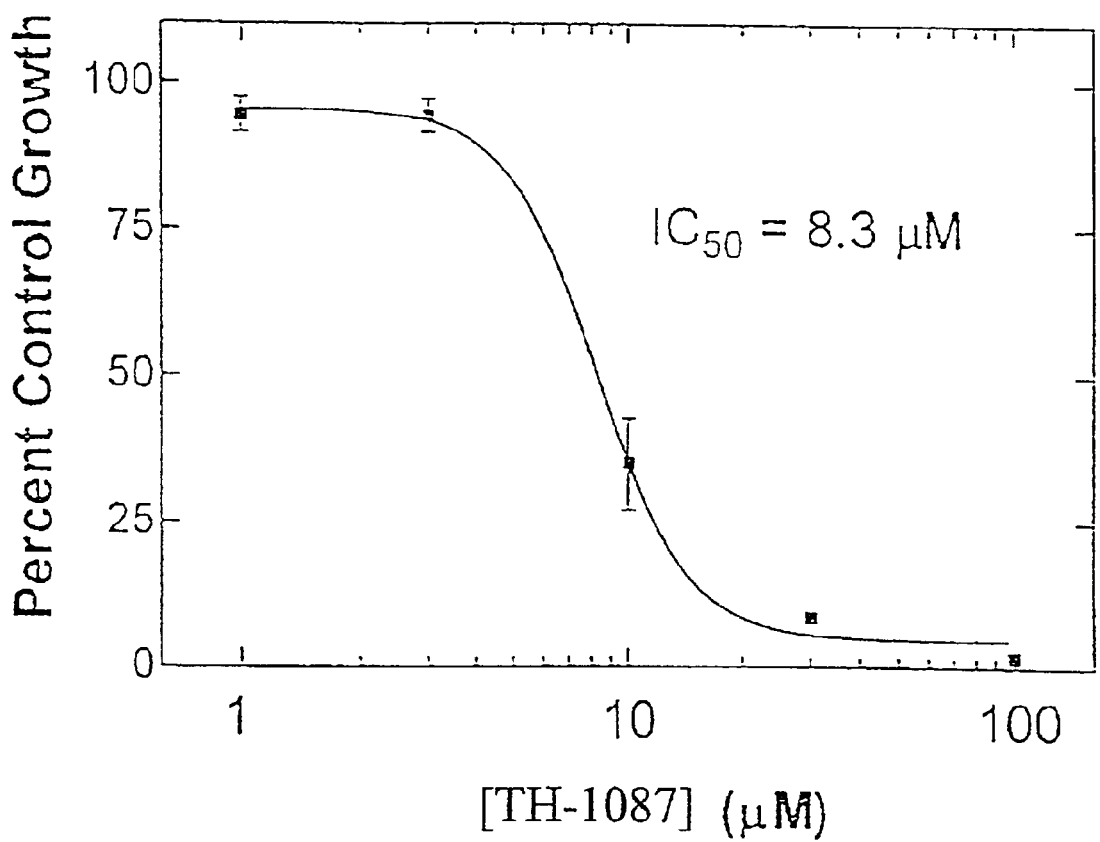
FIG. 10 tabulates and graphically illustrates the effect of TH-1087 on cellular proliferation of Jurkat cells. Jurkat cells at $5\times10^4$/ml in 100 $\mu$l were grown for 48 hours in the absence (100% cell growth) or presence of the indicated concentrations of TH-1087. Results are the mean of 6 determinations.
Figure 11:
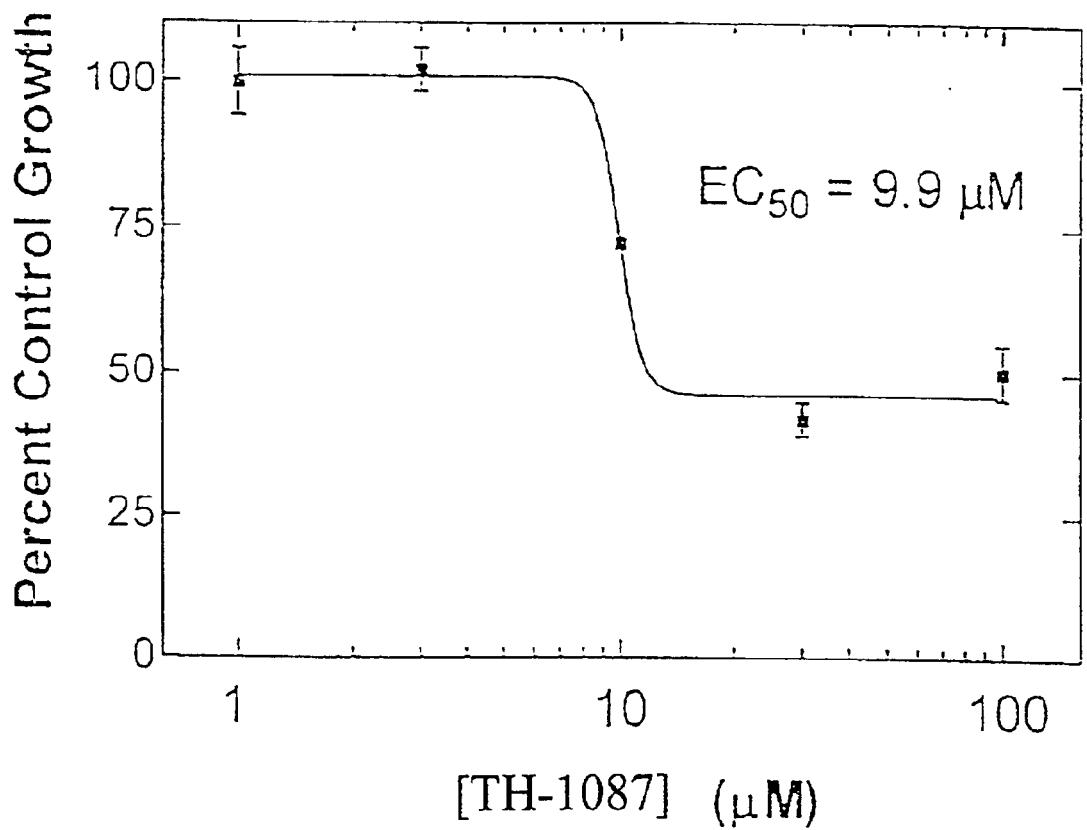
FIG. 11 tabulates and graphically illustrates the effect of TH-1087 on cellular proliferation of PC3 cells. PC3 cells at $5\times10^4$/ml in 100 $\mu$l were grown for 48 hours in the absence (100% cell growth) or presence of the indicated concentrations of TH-1087. Results are the mean of 6 determinations.
Figure 12:
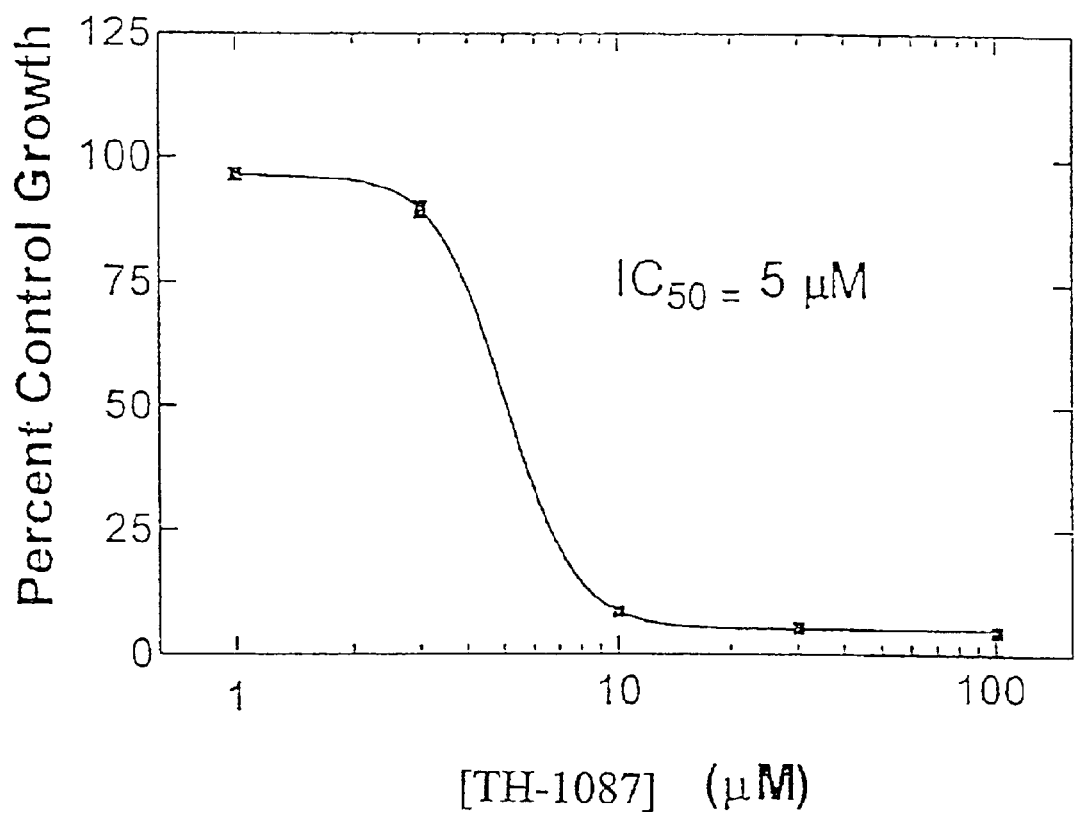
FIG. 12 tabulates and graphically illustrates the effect of TH-1087 on cellular proliferation of LNCaP cells. LNCaP cells at $2.5\times10^4$/ml in 100 $\mu$l were grown for 48 hours in the absence (100% cell growth) or presence of the indicated concentrations of TH-1087. Results are the mean of 6 determinations.
Figure 13:
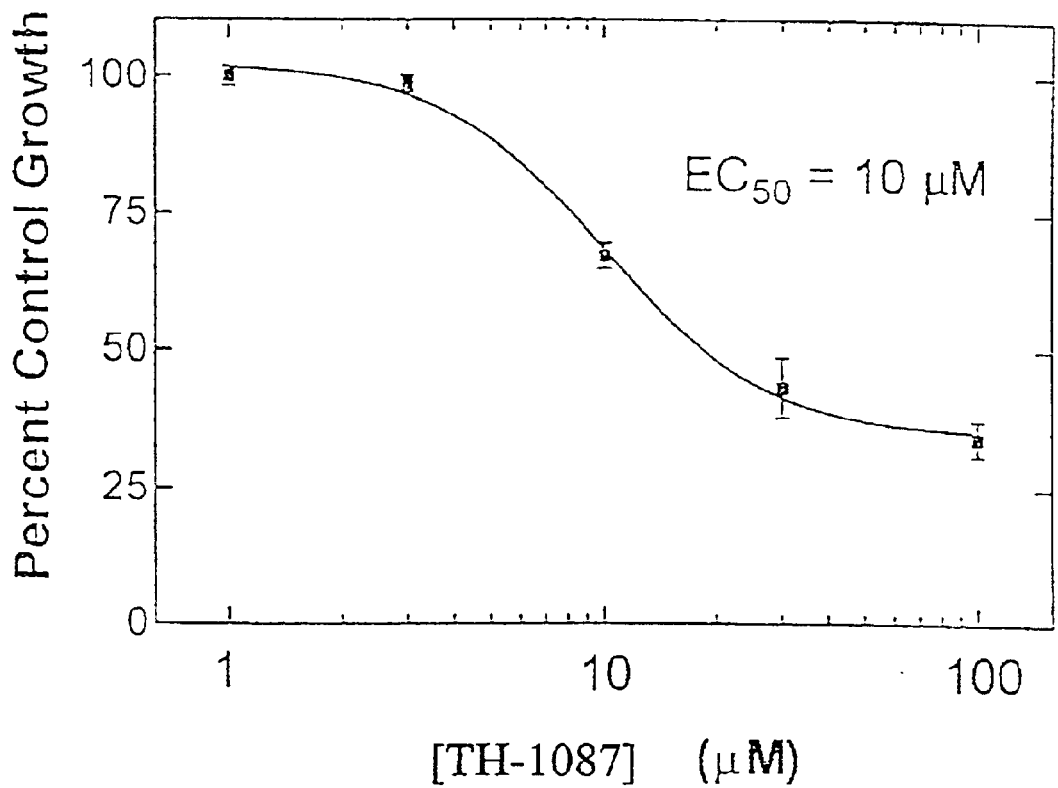
FIG. 13 tabulates and graphically illustrates the effect of TH-1087 on cellular proliferation of MDA-468 cells. MDA-468 cells at $5\times10^4$/ml in 100 $\mu$l were grown for 48 hours in the absence (100% cell growth) or presence of the indicated concentrations of TH-1087. Results are the mean of 6 determinations.
Figure 14:
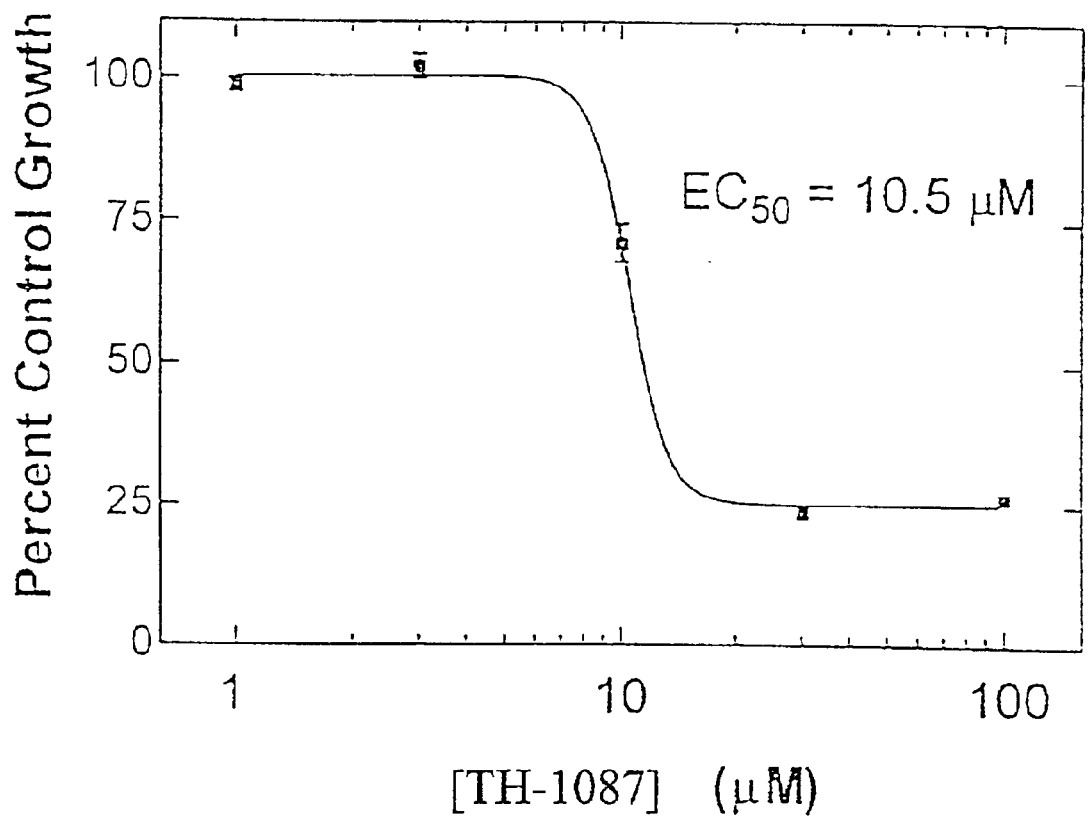
FIG. 14 tabulates and graphically illustrates the effect of TH-1087 on cellular proliferation of MDA-361 cells. MDA-361 cells at $5\times10^4$/ml in 1001 were grown for 48 hours in the absence (100% cell growth) or presence of the indicated concentrations of TH-1087. Results are the mean of 6 determinations.
Figure 15:
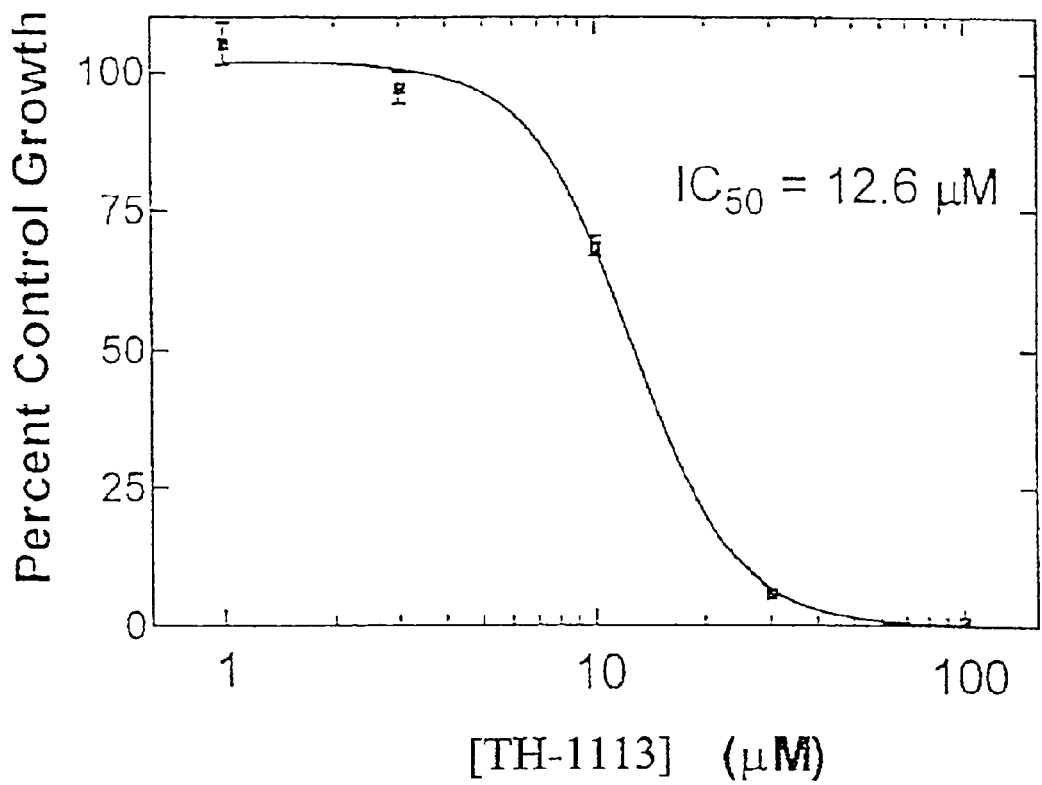
FIG. 15 tabulates and graphically illustrates the effect of TH-1113 on cellular proliferation of Jurkat cells. Jurkat cells at $5\times10^4$/ml in 100 $\mu$l were grown for 48 hours in the absence (100% cell growth) or presence of the indicated concentrations of TH-1113. Results are the mean of 6 determinations.
Figure 16:
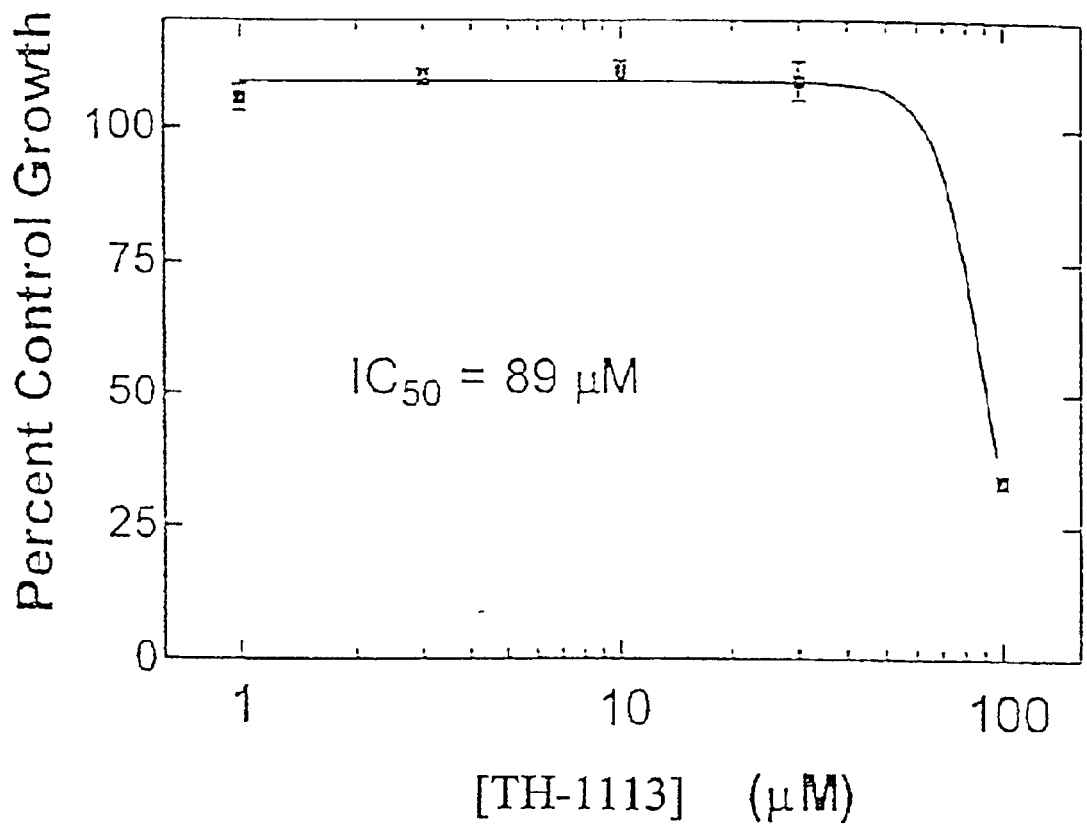
FIG. 16 tabulates and graphically illustrates the effect of TH-1113 on cellular proliferation of PC3 cells. PC3 cells at $5\times10^4$/ml in 100 $\mu$l were grown for 48 hours in the absence (100% cell growth) or presence of the indicated concentrations of TH-1113. Results are the mean of 6 determinations.
Figure 17:
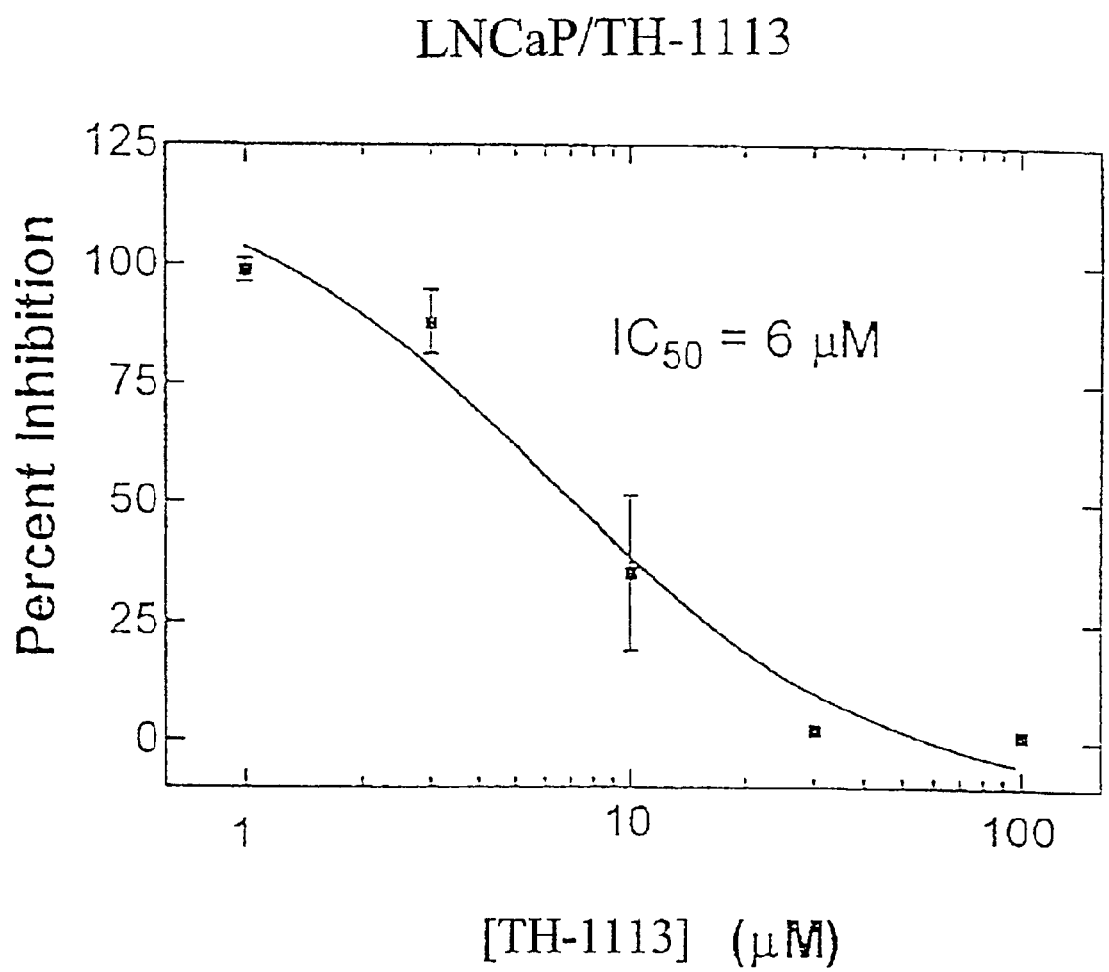
FIG. 17 tabulates and graphically illustrates the effect of TH-1113 on cellular proliferation of LNCaP cells. LNCaP cells at $2.5\times10^4$/ml in 100 $\mu$l were grown for 48 hours in the absence (100% cell growth) or presence of the indicated concentrations of TH-1113. Results are the mean of 6 determinations.
Figure 18:
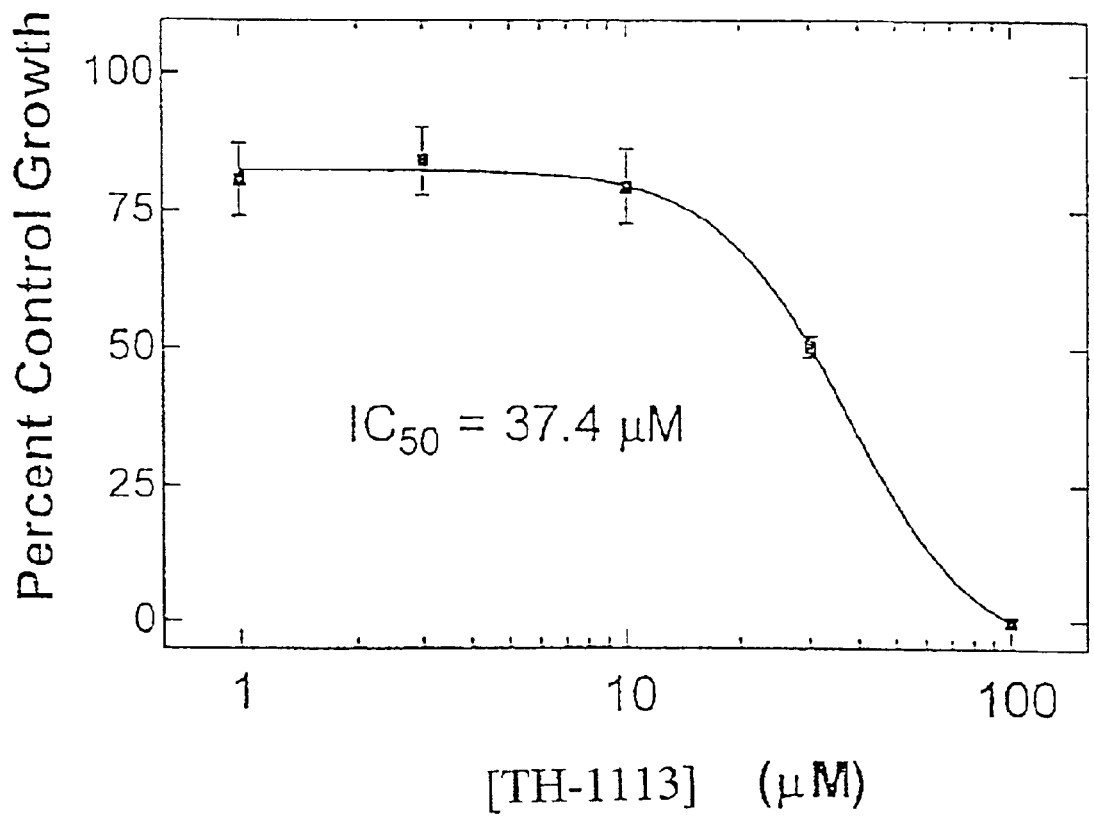
FIG. 18 tabulates and graphically illustrates the effect of TH-1113 on cellular proliferation of MDA-468 cells. MDA-468 cells at $5\times10^4$/ml in 100 $\mu$l were grown for 48 hours in the absence (100% cell growth) or presence of the indicated concentrations of TH-1113. Results are the mean of 6 determinations.
Figure 19:
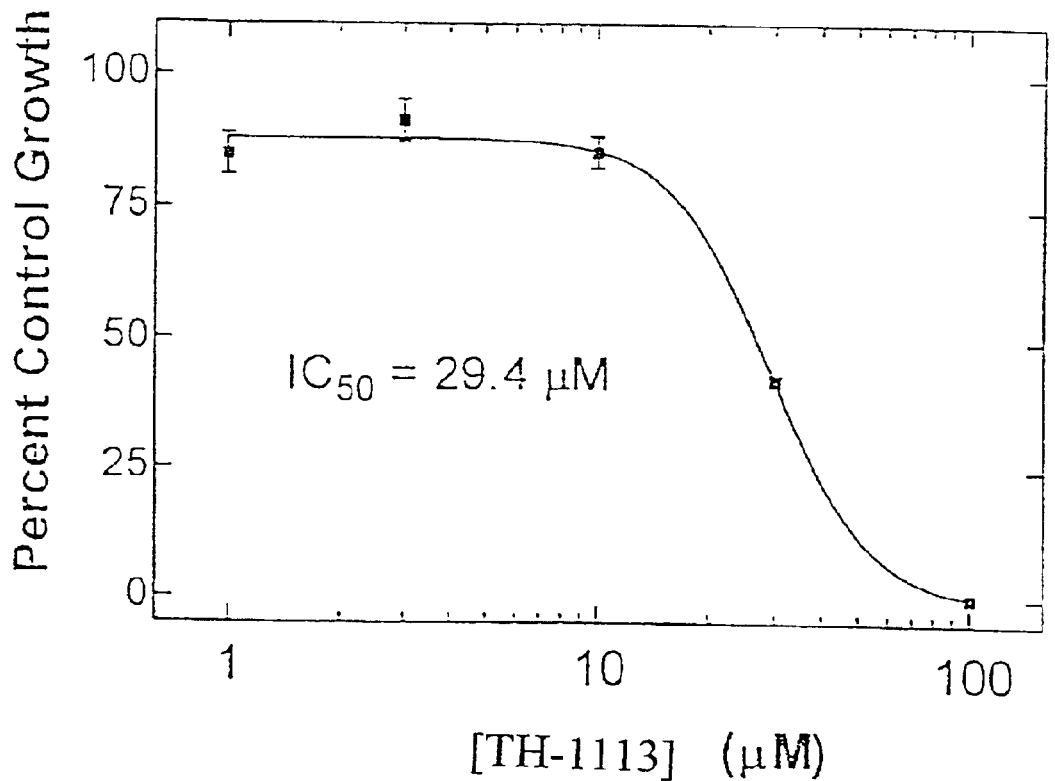
FIG. 19 tabulates and graphically illustrates the effect of TH-1113 on cellular proliferation of MDA-361 cells. MDA-361 cells at $5\times10^4$/ml cells in 100 $\mu$l were grown for 48 hours in the absence (100% cell growth) or presence of the indicated concentrations of TH-1113. Results are the mean of 6 determinations.
Figure 20:
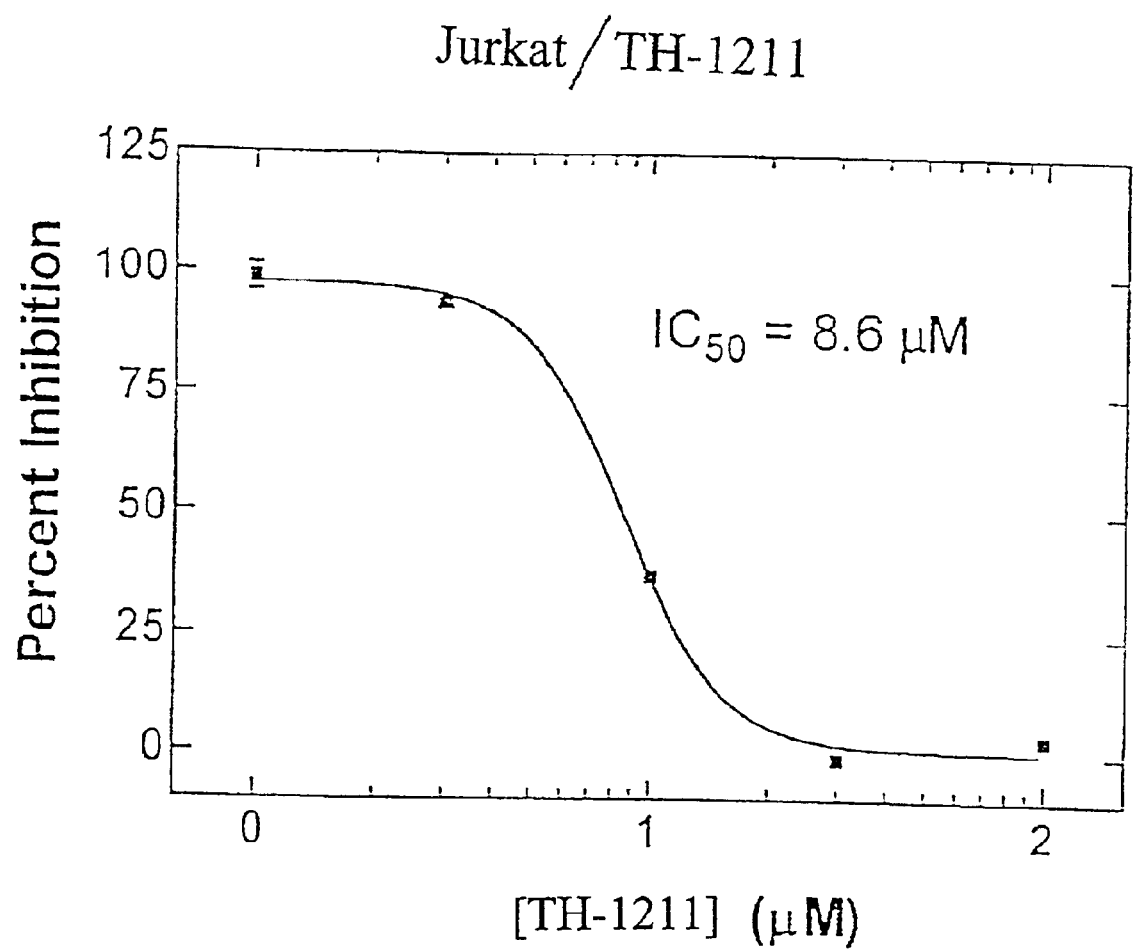
FIG. 20 tabulates and graphically illustrates the effect of TH-1211 on cellular proliferation of Jurkat cells. Jurkat cells at $5\times10^4$/ml in 100 $\mu$l were grown for 48 hours in the absence (100% cell growth) or presence of the indicated concentrations of TH-$^{1211}$. Results are the mean of 6 determinations.
Figure 21:
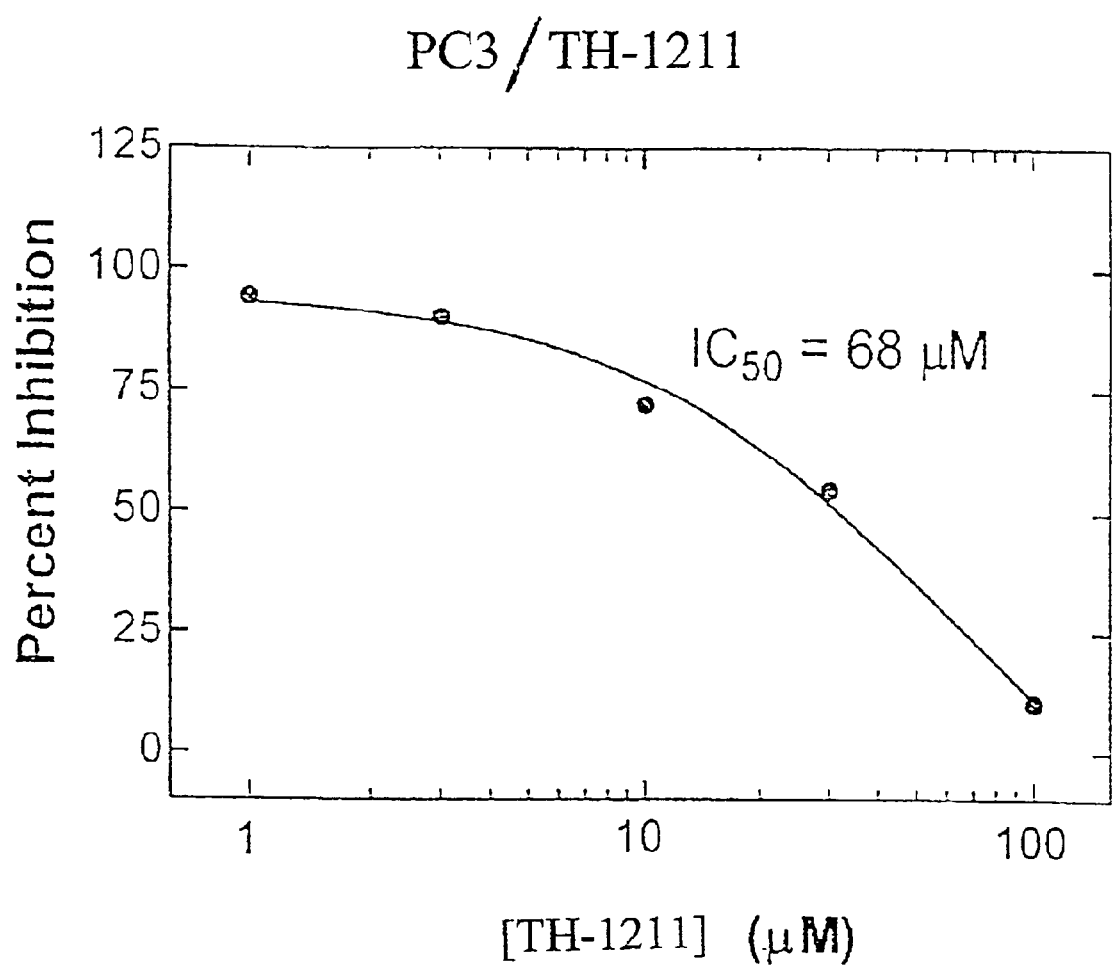
FIG. 21 tabulates and graphically illustrates the effect of TH-$^{1211}$ on cellular proliferation of PC3 cells. PC3 cells at $5\times10^4$/ml in 100 µl were grown for 48 hours in the absence (100% cell growth) or presence of the indicated concentrations of TH-121. Results are the mean of 6 determinations.
Figure 22:
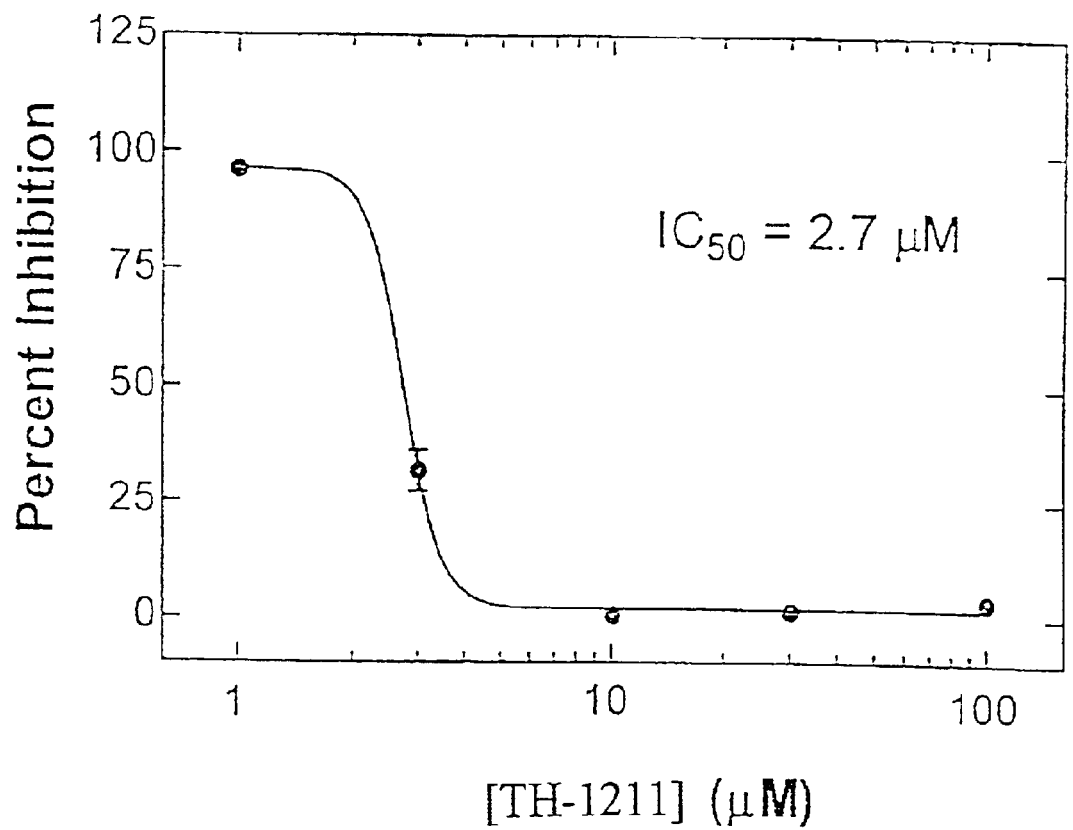
FIG. 22 tabulates and graphically illustrates the effect of TH-1211 on cellular proliferation of LNCaP cells. LNCaP cells at $2.5\times10^4$/ml in 10011 were grown for 48 hours in the absence (100% cell growth) or presence of the indicated concentrations of TH-1211. Results are the mean of 6 determinations.
Figure 23:
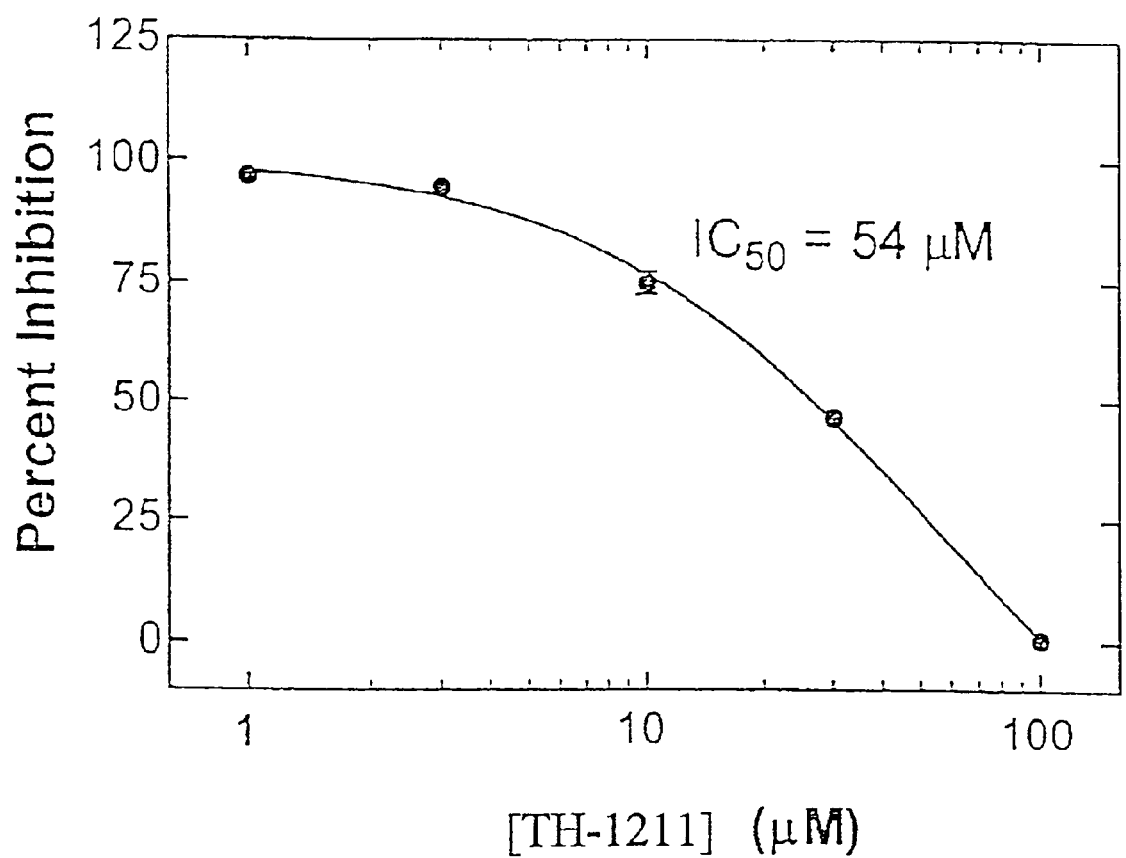
FIG. 23 tabulates and graphically illustrates the effect of TH-1211 on cellular proliferation of MDA-468 cells. MDA-468 cells at $5\times10^4$/ml in 100 µl were grown for 48 hours in the absence (100% cell growth) or presence of the indicated concentrations of TH-1211. Results are the mean of 6 determinations.
Figure 24:
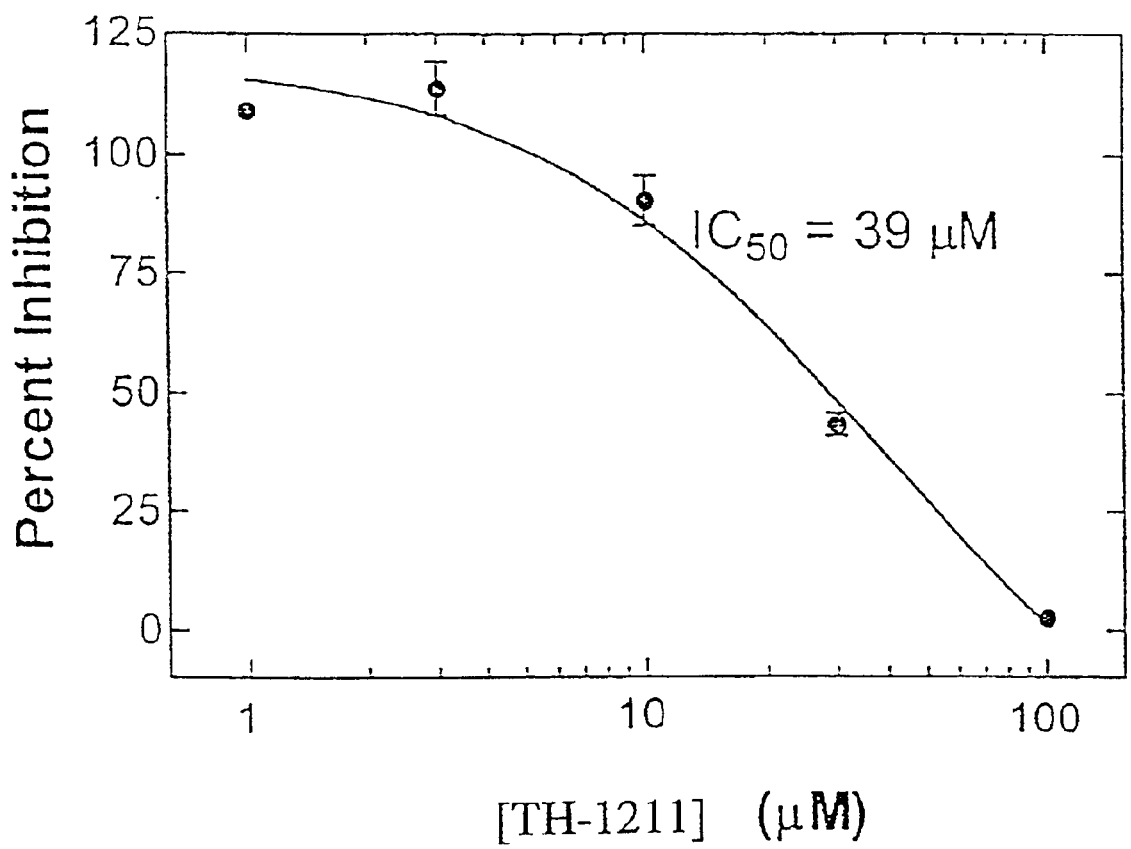
FIG. 24 tabulates and graphically illustrates the effect of TH-1211 on cellular proliferation of MDA-361 cells. MDA-361 cells at $5\times10^4$/ml in 100 µl were grown for 48 hours in the absence (100% cell growth) or presence of the indicated concentrations of TH-1211. Results are the mean of 6 determinations.
Figure 25:
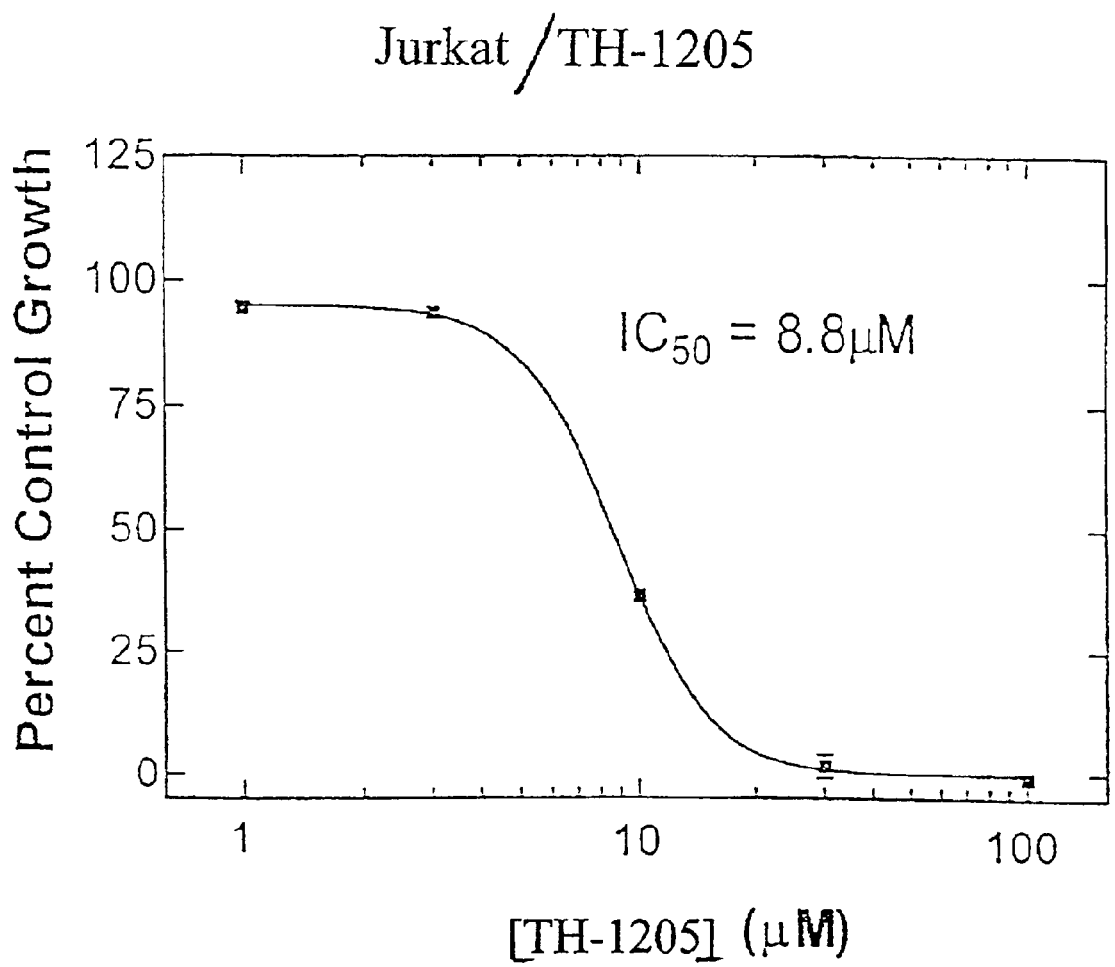
FIG. 25 tabulates and graphically illustrates the effect of TH-1205 on cellular proliferation of Jurkat cells. Jurkat cells at $5\times10^4$/ml in 100 µl were grown for 48 hours in the absence (100% cell growth) or presence of the indicated concentrations of TH-1205. Results are the mean of 6 determinations.
Figure 26:
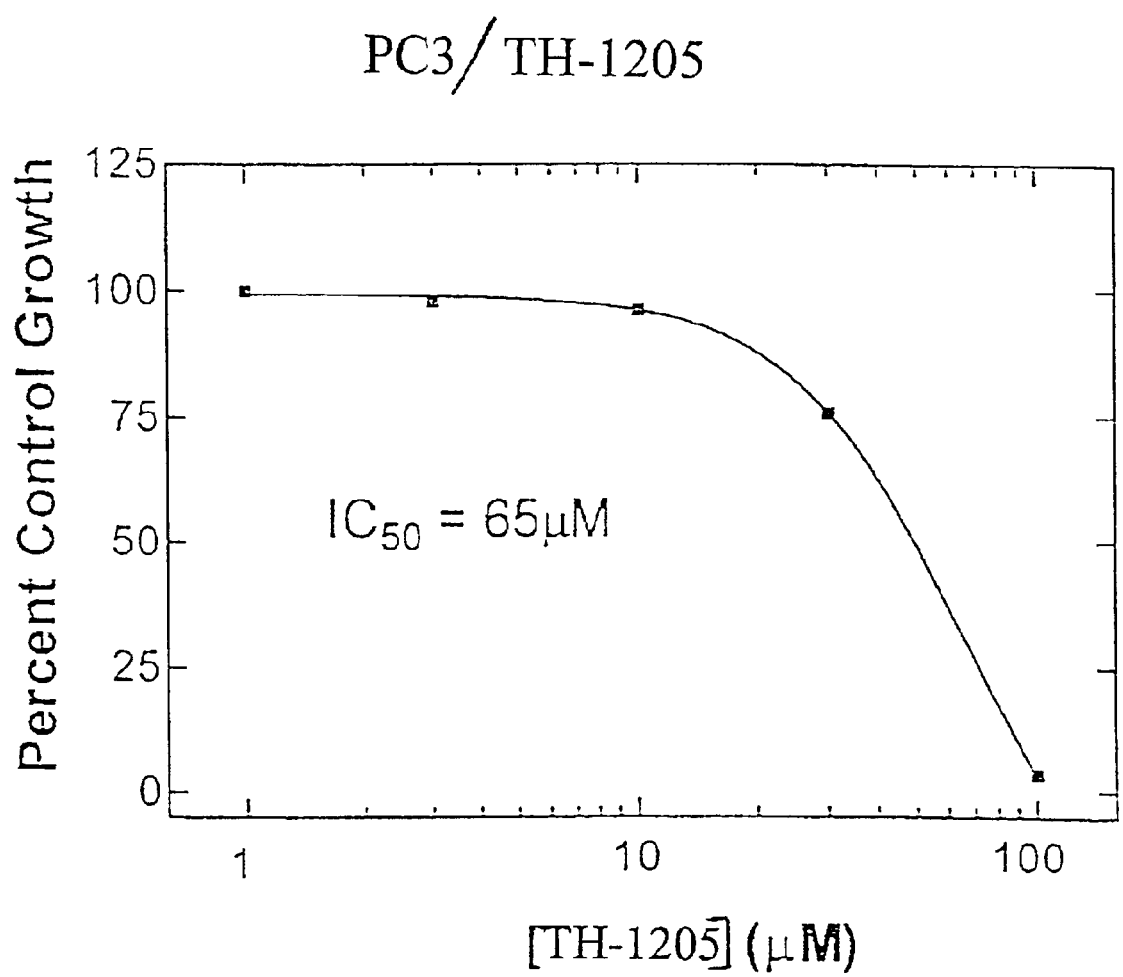
FIG. 26 tabulates and graphically illustrates the effect of TH-1205 on cellular proliferation of PC3 cells. PC3 cells at $5\times10^4$/ml in 100 µl were grown for 48 hours in the absence (100% cell growth) or presence of the indicated concentrations of TH-1205. Results are the mean of 6 determinations.
Figure 27:
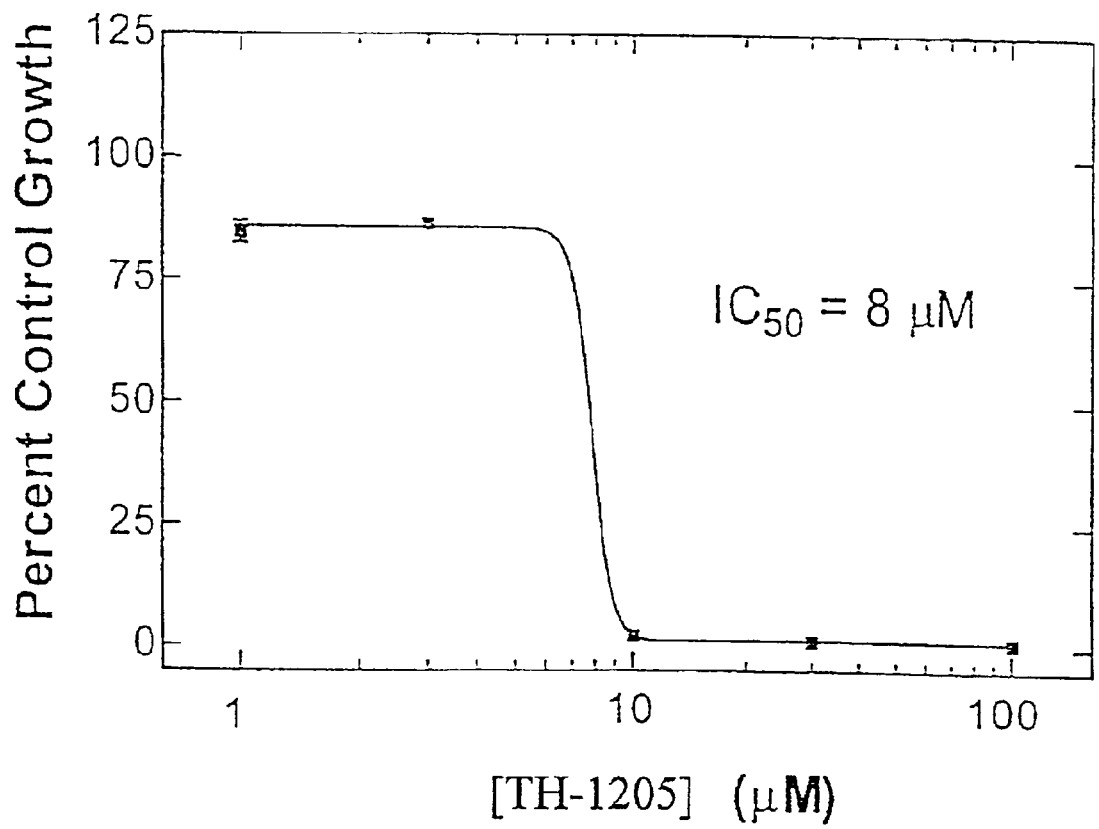
FIG. 27 tabulates and graphically illustrates the effect of TH-1205 on cellular proliferation of LNCaP cells. LNCaP cells at $2.5\times10^4$/ml in 100 µl were grown for 48 hours in the absence (100% cell growth) or presence of the indicated concentrations of TH-1205. Results are the mean of 6 determinations.
Figure 28:
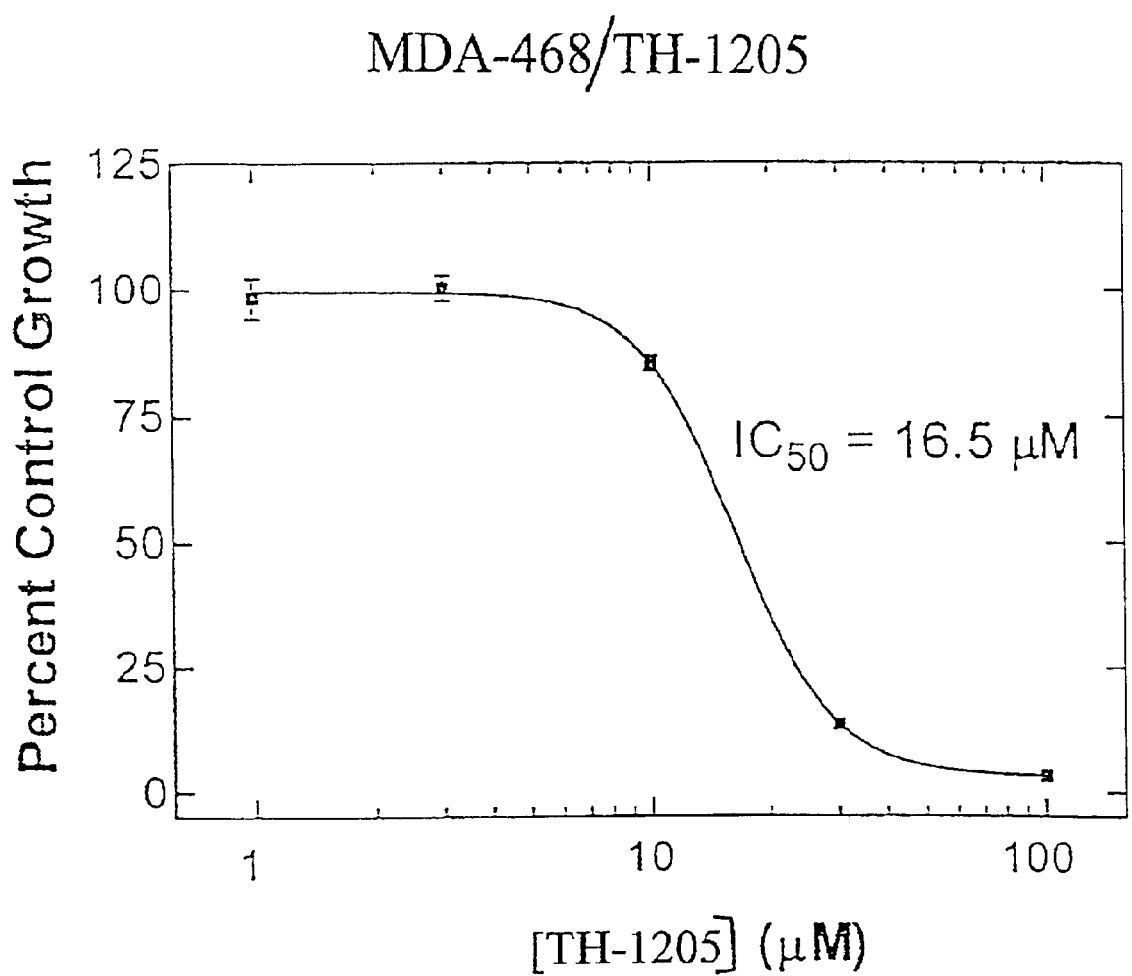
FIG. 28 tabulates and graphically illustrates the effect of TH-1205 on cellular proliferation of MDA-468 cells. MDA-468 cells at $5\times10^4$/ml in 100 µl were grown for 48 hours in the absence (100% cell growth) or presence of the indicated concentrations of TH-1205. Results are the mean of 6 determinations.
Figure 29:
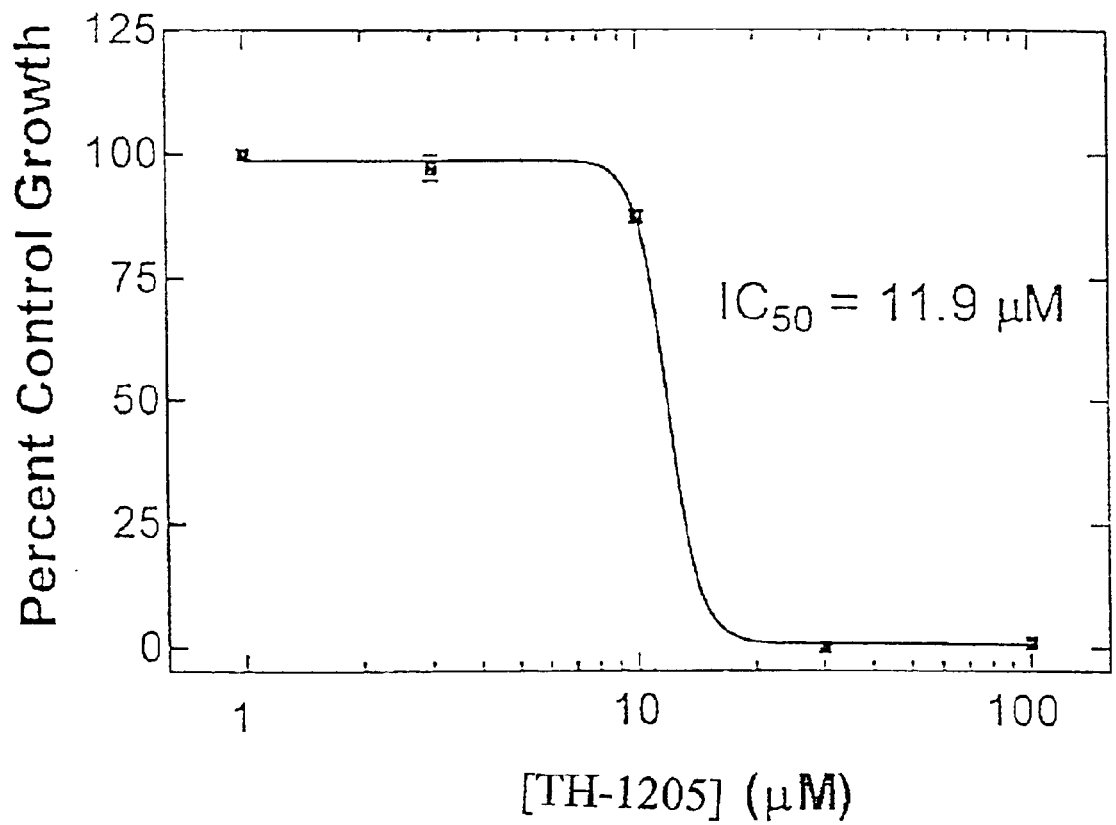
FIG. 29 tabulates and graphically illustrates the effect of TH-1205 on cellular proliferation of MDA-361 cells. MDA-361 cells at $5\times10^4$/ml in 100 µl were grown for 48 hours in the absence (100% cell growth) or presence of the indicated concentrations of TH-1205. Results are the mean of 6 determinations.
Figure 30:
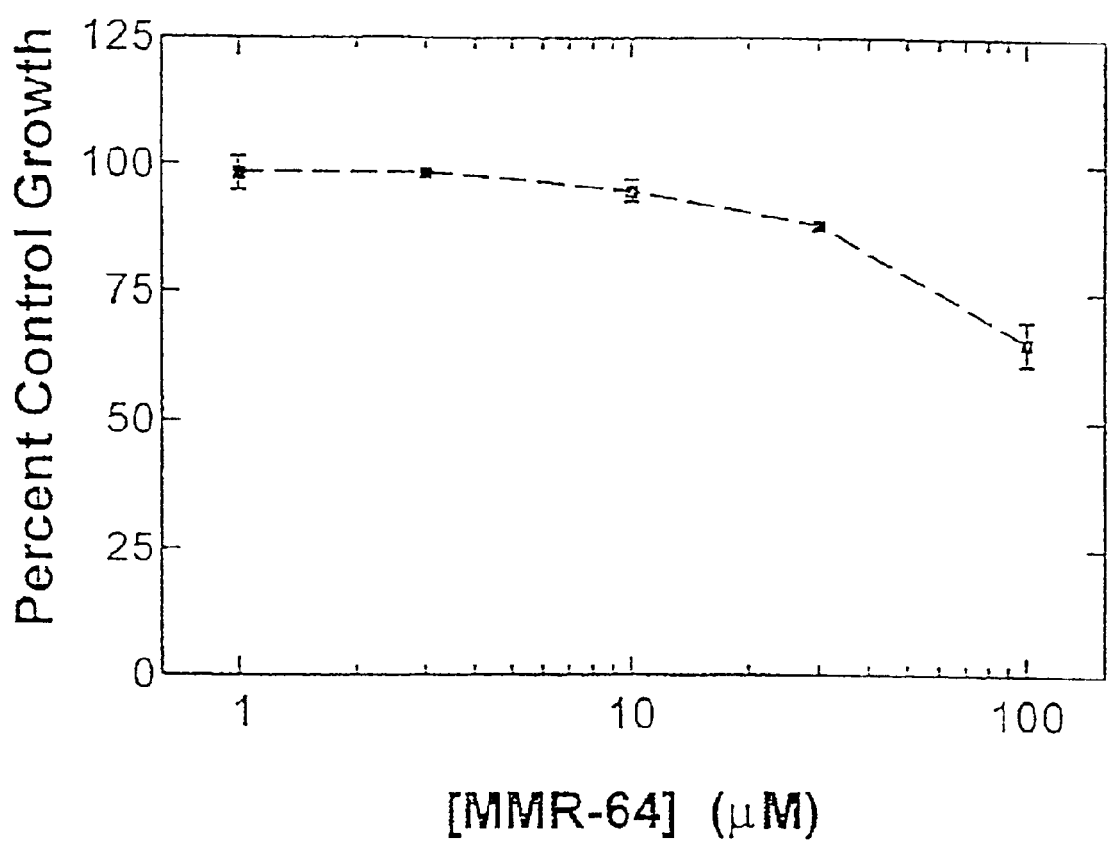
FIG. 30 tabulates and graphically illustrates the effect of MMR-64 on cellular proliferation of Jurkat cells. Jurkat cells at $5\times10^4$/ml in 100 µl were grown for 48 hours in the absence (100% cell growth) or presence of the indicated concentrations of MMR-64. Results are the mean of 6 determinations.
Figure 31:
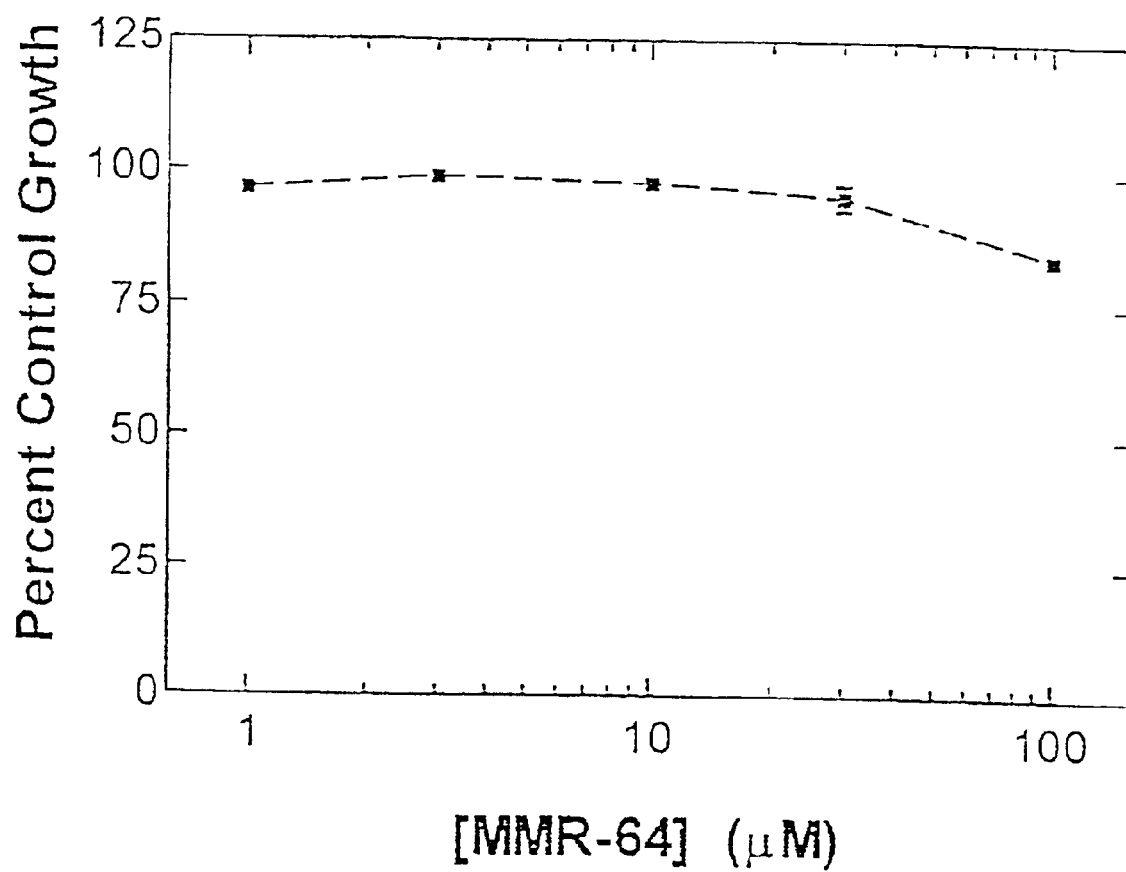
FIG. 31 tabulates and graphically illustrates the effect of MMR-64 on cellular proliferation of PC3 cells. PC3 cells at $5\times10^4$/ml in 100 µl were grown for 48 hours in the absence (100% growth) or presence of the indicated concentrations of MMR-64. Results are the mean of 6 determinations.
Figure 32:
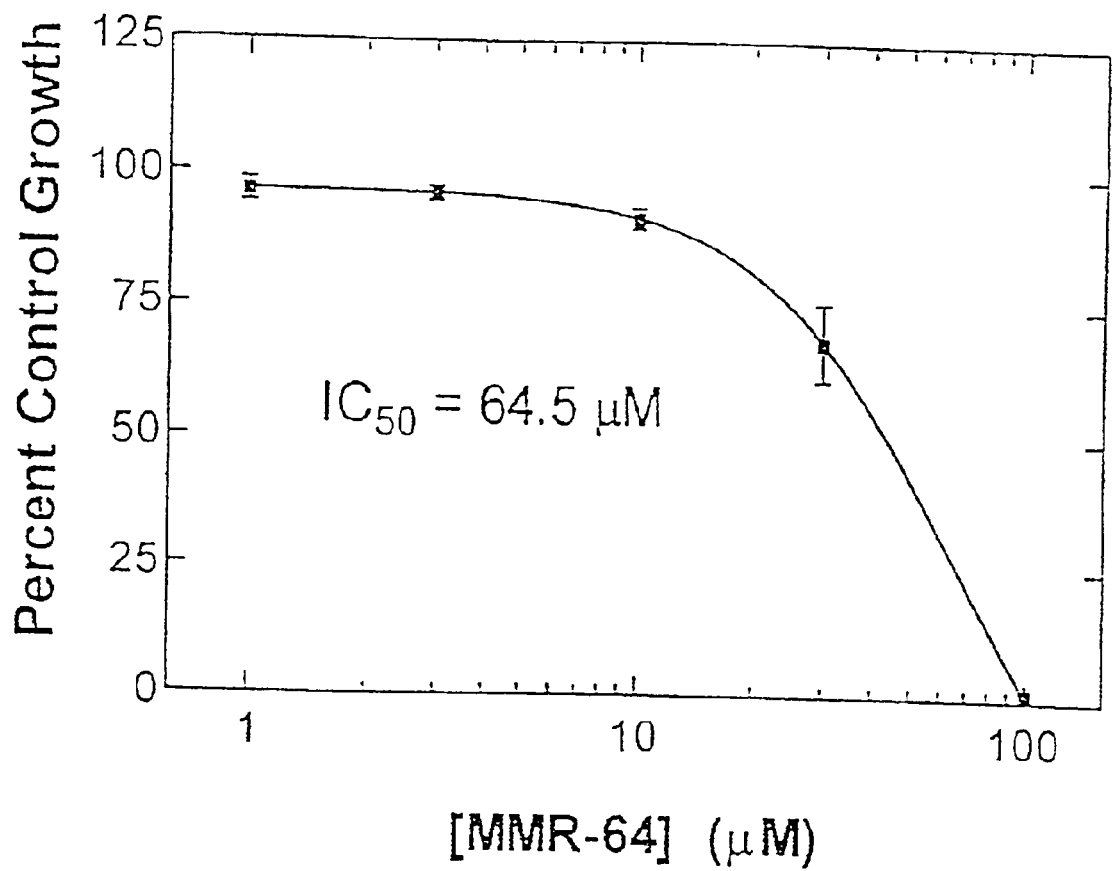
FIG. 32 tabulates and graphically illustrates the effect of MMR-64 on cellular proliferation of LNCaP cells. LNCaP cells at $2.5\times10^4$/ml in 100 µl were grown for 48 hours in the absence (100% cell growth) or presence of the indicated concentrations of MMR-64. Results are the mean of 6 determinations.
Figure 33:
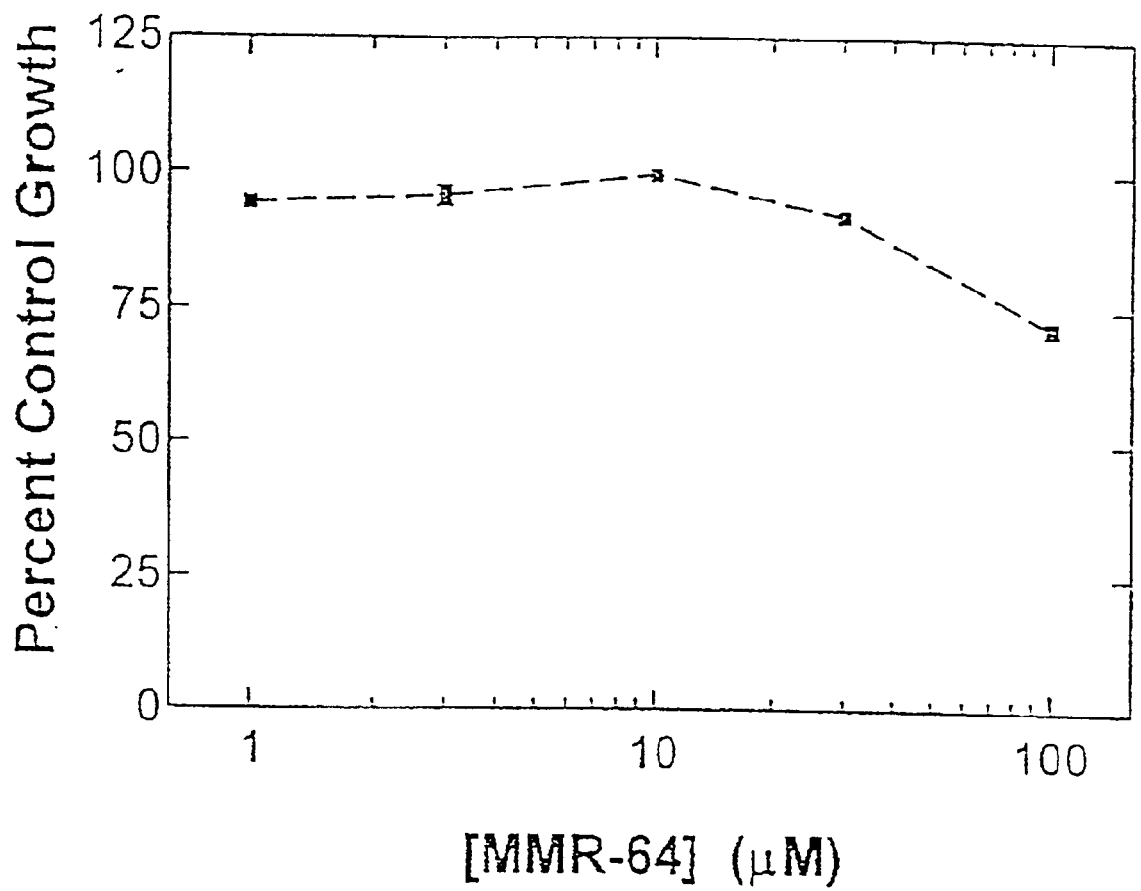
FIG. 33 tabulates and graphically illustrates the effect of MMR-64 on cellular proliferation of MDR-468 cells. MDR-468 cells at $5\times10^4$/ml in 100 µl were grown for 48 hours in the absence (100% cell growth) or presence of the indicated concentrations of MMR-64. Results are the mean of 6 determinations.
Figure 34:
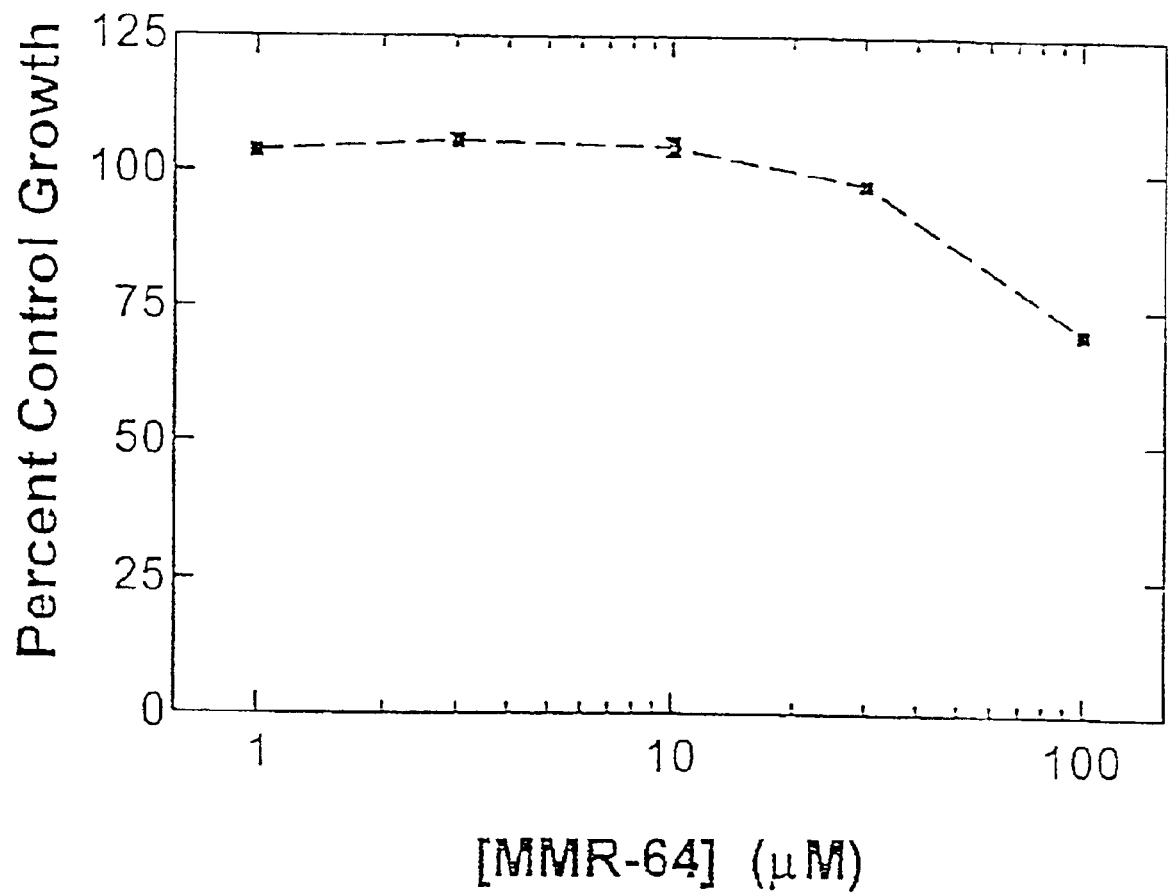
FIG. 34 tabulates and graphically illustrates the effect of MMR-64 on cellular proliferation of MDA-361 cells. MDA-361 cells at $5\times10^4$/ml in 100 µl were grown for 48 hours in the absence (100% cell growth) or presence of the indicated concentrations of MMR-64. Results are the mean of 6 determinations.
Figure 35:
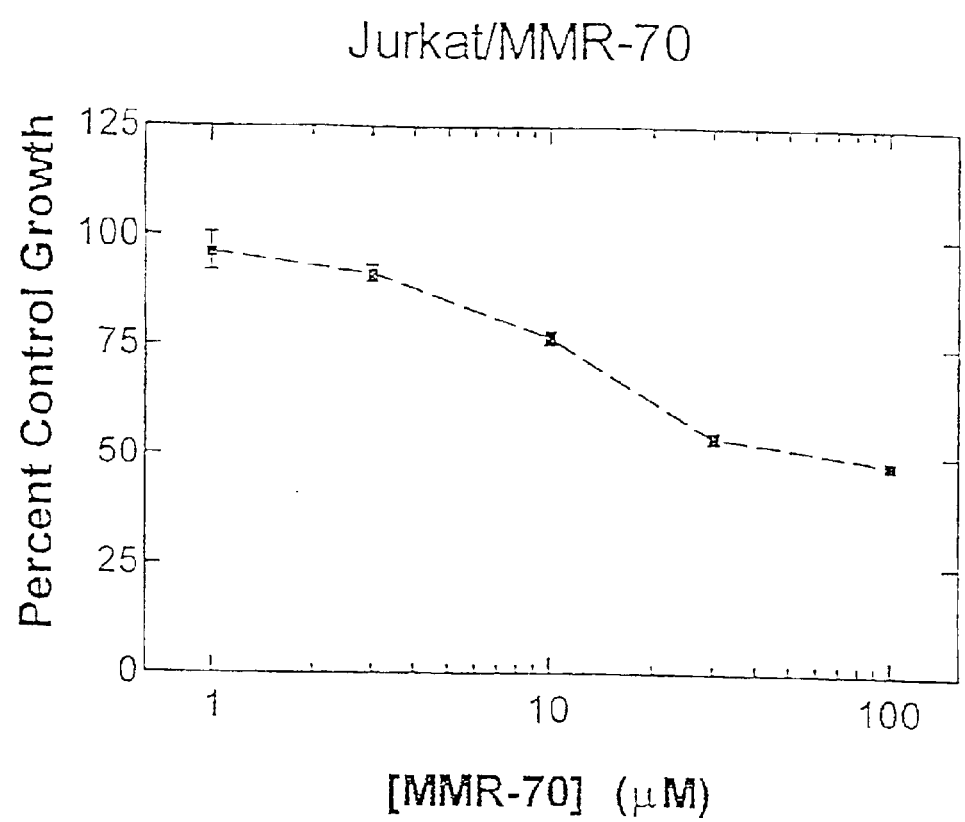
FIG. 35 tabulates and graphically illustrates the effect of MMR-70 on cellular proliferation of Jurkat cells. Jurkat cells at $5\times10^4$/ml in 100 µl were grown for 48 hours in the absence (100% cell growth) or presence of the indicated concentrations of MMR-70. Results are the mean of 6 determinations.
Figure 36:
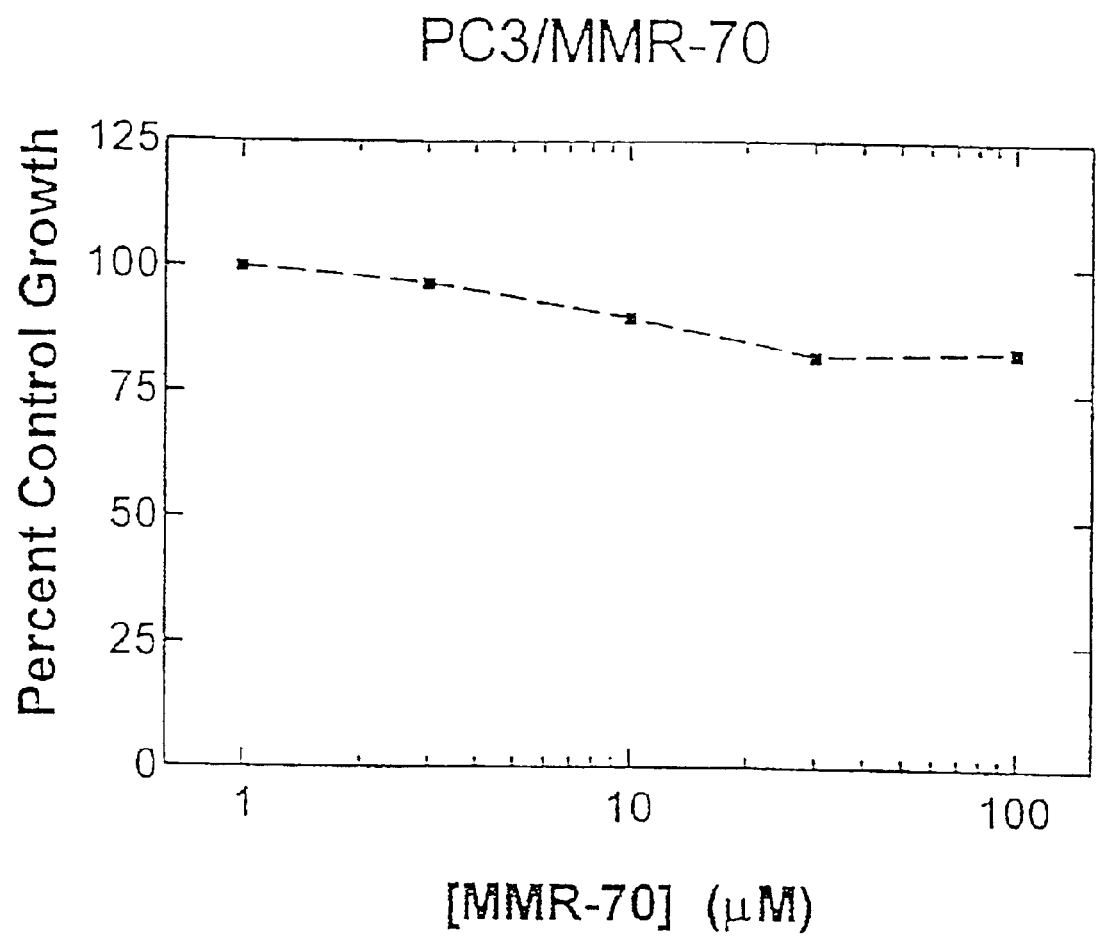
FIG. 36 tabulates and graphically illustrates the effect of MMR-70 on cellular proliferation of PC3 cells. PC3 cells at $5\times10^4$/ml in 100 µl were grown for 48 hours in the absence (100% cell growth) or presence of the indicated concentrations of MMR-70. Results are the mean of 6 determinations.
Figure 37:
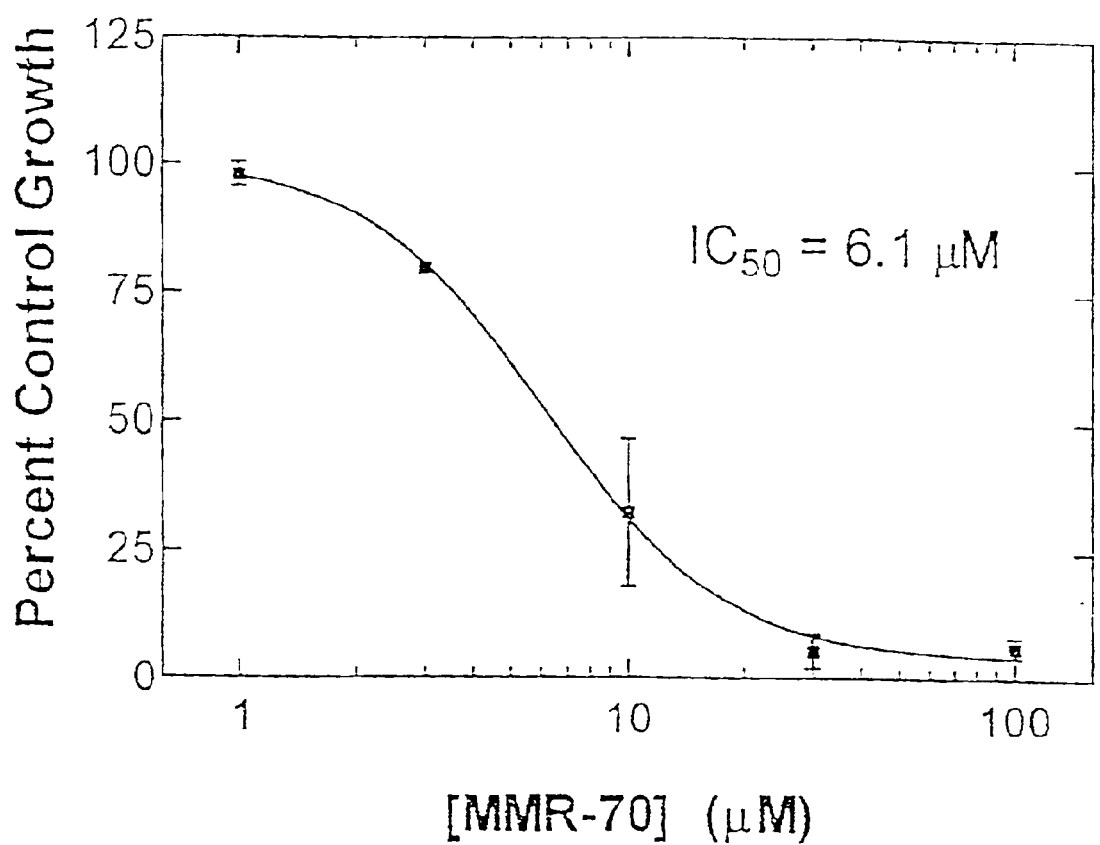
FIG. 37 tabulates and graphically illustrates the effect of MMR-70 on cellular proliferation of LNCaP cells. LNCaP cells at $2.5\times10^4$/ml in 100 µl were grown for 48 hours in the absence (100% cell growth) or presence of the indicated concentrations of MMR-70. Results are the mean of 6 determinations.
Figure 38:
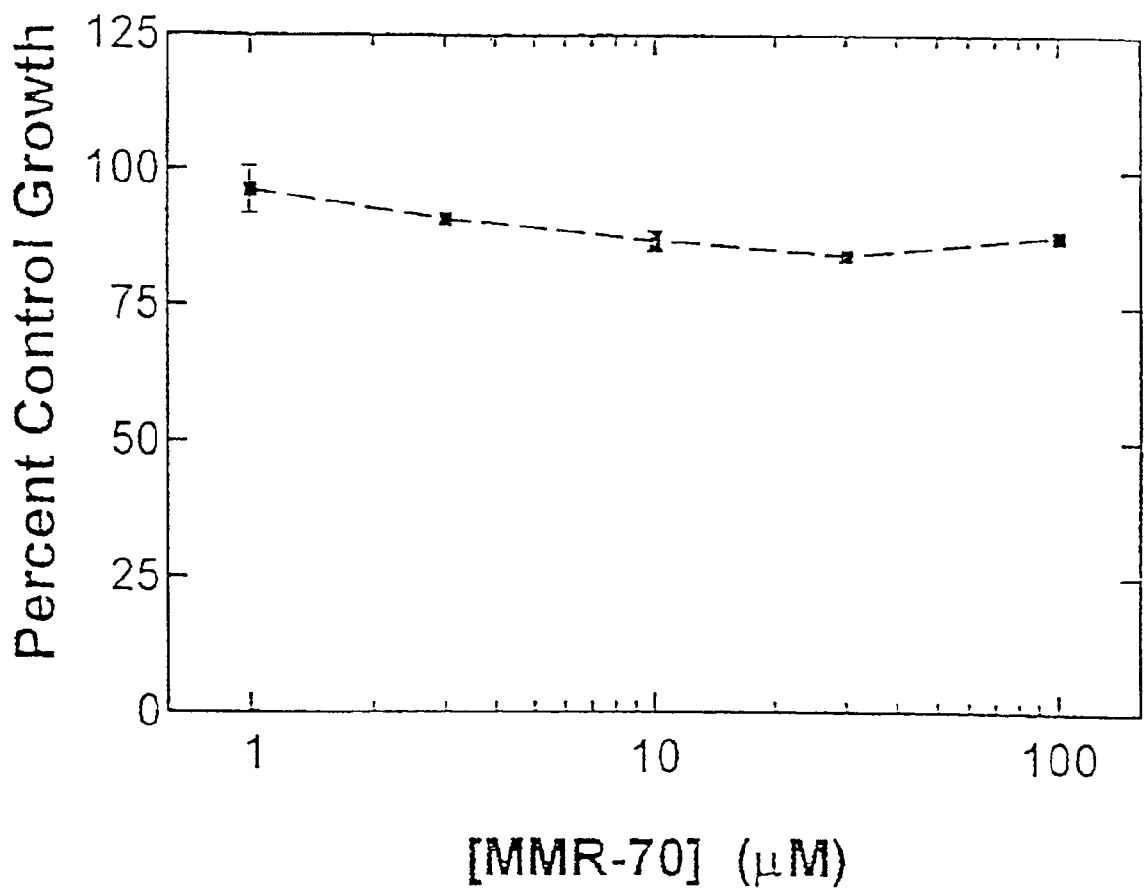
FIG. 38 tabulates and graphically illustrates the effect of MMR-70 on cellular proliferation of MDA-468 cells. MDA-468 cells at $5\times10^4$/ml in 100 µl were grown for 48 hours in the absence (100% cell growth) or presence of the indicated concentrations of MMR-70. Results are the mean of 6 determinations.
Figure 39:
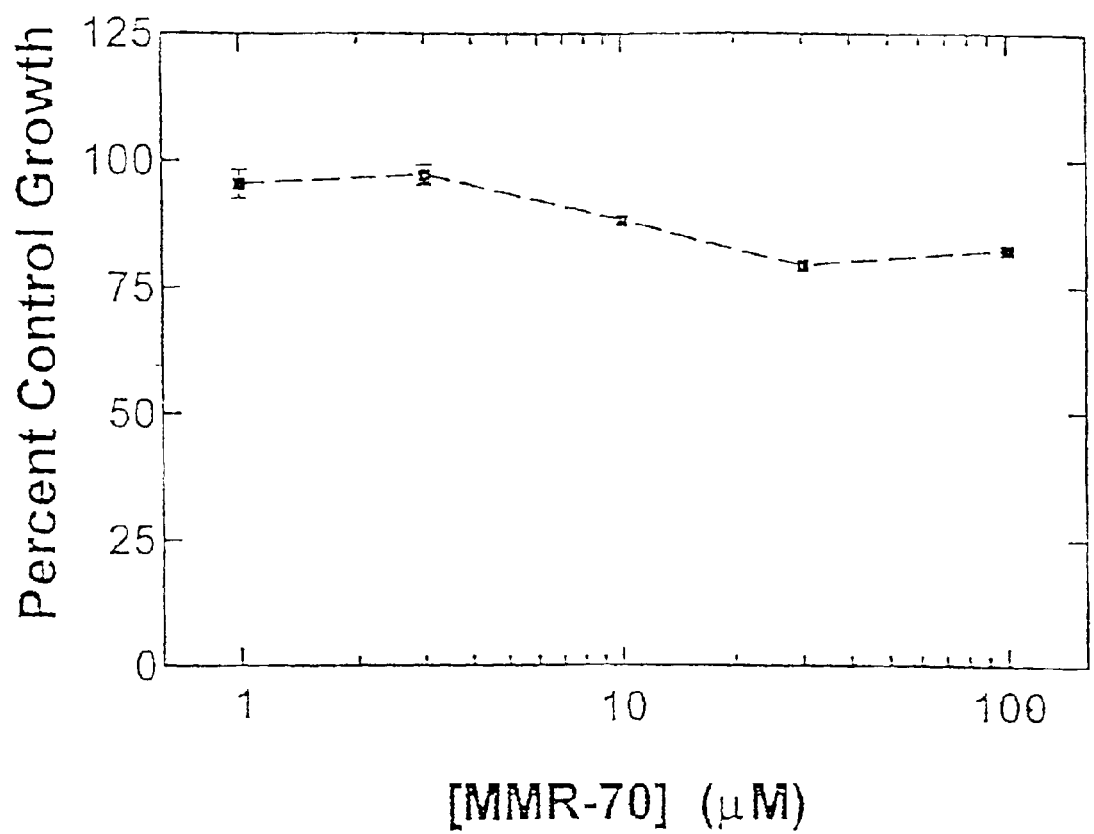
FIG. 39 tabulates and graphically illustrates the effect of MMR-70 on cellular proliferation of MDA-361 cells. MDA-361 cells at $5\times10^4$/ml in 100 µl were grown for 48 hours in the absence (100% cell growth) or presence of the indicated concentrations of MMR-70. Results are the mean of 6 determinations.

TH-1177 slowed prostate cancer progression in vivo. To begin an investigation of the possibility that TH-1177 possesses in vivo activity against prostate cancer, SCID mice were inoculated with PC3 cells by IP injection. One day later, daily IP injections of TH-1177 or vehicle alone were begun. TH1177 was administered at doses or either 3 mg/kg or 10 mg/kg. These doses were selected based upon the general range of doses for $Ca^{2+}$ channel blockers given by mouth to patients for the treatment of hypertension. Daily dosing was also selected based upon the general desirability of a once-a-day treatment regimen. As shown in FIG. 9, there was a dose dependent increase in longevity associated with TH-1177 administration. Life span was increased by 34% (p=0.047) by TH-1177 at a dose of 3 mg/kg/d and by 38% (p=0.0044) at a dose of 10 mg/kg/d.

Although the experiment of FIG. 9 suggested a lack of toxicity associated with TH-1177 administration, the drug was further examined specifically for possible toxicity. Four SCID mice without tumors were given TH-1177 at a dose of 180 mg/kd/d. Treated mice were all well groomed and active during treatment and no gross abnormalities were noted at necropsy. Samples of kidney, adrenal gland, heart and liver were within normal limits on histological examination including active hepatic hematopoiesis.

EXAMPLE 6

Using the measurement cell proliferation assay described hereinabove, the cell lines Jurkat, LNCap (prostate cancer cell), PC-31 (prostate cancer cell), DU145 (prostate cancer cell), MDA-468 (breast cancer cell), MDA-36 (Breast cancer cell), MCF-7 (breast cancer cell), MIA PaCa-2 (pancreatic cancer cell), Hep G2 (liver cancer cell), A549 (non-small cell lung cancer cells), NCI H460 (non-small cell lung cancer cells), HT-29 (colon cancer cell), HCT-116 (colon cancer cell) and SK OV-3 (ovarian cancer cell) were cultured in the presence of TH-1177, TH-1205, TH-1201, TH-2109, TH-2029, TH-2043, TN-2085 and TH-2279. $IC_{50}$ values in $\mu M$ are tabulated hereinbelow:

EXAMPLE 7

Repeating the cell proliferation test of Example 6, TH-3101, TH-3104 and TH-3105 were each tested on various cell lines: Jurkat, LNCap and MDA-361. The results are tabulated hereinbelow:

|  | Jurkat | LNCaP | MDA-361 |
|---|---|---|---|
| TH-3101 | 4.6 $\mu M$ | 4.1 $\mu M$ | 7.3 $\mu M$ |
| TH-3104 | 3.8 $\mu M$ | 2.4 $\mu M$ | 13.0 $\mu M$ |
| TH-3105 | 5.0 $\mu M$ | 3.2 $\mu M$ | 29.0 $\mu M$ |

EXAMPLE 8

The $IC_{50}$ values for TH-1177 and other related drugs in the proliferation test on LNCaP were plotted against $IC_{50}$ values for Inhibition of Calcium Influx (obtained in accordance with the procedure described hereinabove of measurement of intracellular calcium concentration) with respect to LNCaP cells.

Figure 40:
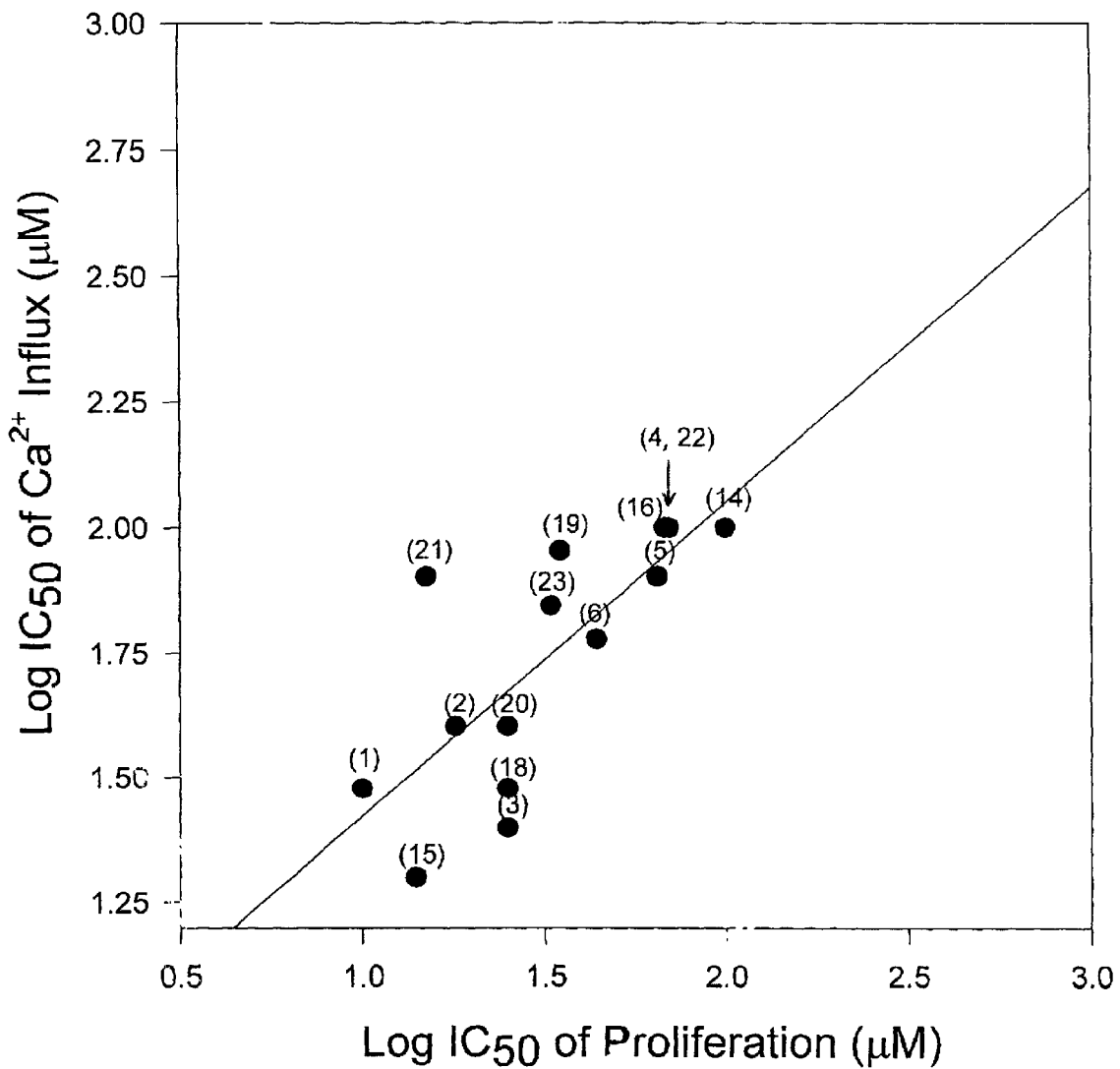
FIG. 40 graphically illustrates the correlation of inhibition of Calcium Influx and Proliferation in LNCaP cells by exemplary compounds of the present invention. The legend respecting the compounds are as indicated hereinbelow.

The results are graphically depicted in FIG. 40. The graph clearly shows that two functions are correlated in a linear fashion.

EXAMPLE 9

Xenopus oocytes were transfected with the α1H subunit of a calcium channel of a human heart prepared in accordance with the procedure described by Cribbs, et al. in *Circulation Research*, 1998, 83, 103–109, the contents of which are incorporated by reference. The α1H plasmid was obtained by cloning the α1H sequence into the EcoRV-X baI site of the transfection vector pcDNA3, in accordance with the procedure described in the Cribbs, et al. article. Xenopus oocyte cells ($1\times10^5$ per 35 mm dish) were transfected with 2 $\mu g$ of alpha 1H-Tx plasmid. The transfected cells were depolarized with standard depolarizing bath solution con-

| | PROLIFERATION $IC_{50}$ | | | | | | | | | | | | | |
|---|---|---|---|---|---|---|---|---|---|---|---|---|---|---|
| DRUG | Jurkat | LNCaP | PC-3 | DU 145 | MDA-468 | MDA-361 | MCF-7 | MIA PaCa-2 | Hep G2 | A549 | NCI H460 | HT-29 | HCT 116 | SK-OV-3 |
| TH-1177 | 8 | 4 | 15 | 19 | 13 | 26 | 21 | 17 | 32 | 71 | 15 | ~100 | 37 | 25 |
| TH-1205 | 11 | 5 | 23 | 21 | 13 | 19 | 70 | 17 | 40 | 93 | 35 | ~100 | 30 | 33 |
| TH-1211 | 4 | 3 | 17 | 13 | 11 | 14 | 24 | 17 | 20 | 41 | 13 | ~90 | 32 | 23 |
| TH-2019 | 7 | 4 | 19 | 28 | 21 | 23 | 30 | 17 | 30 | 72 | 12 | ~100 | 31 | 30 |
| TH-2029 | 11 | 5 | 18 | 17 | 10 | 16 | 37 | 17 | 30 | 26 | 24 | ~60 | 18 | 24 |
| TH-2043 | 8 | 4 | 14 | 9 | 8* | 13 | 29 | 17 | >100 | 20 | 10 | >100 | 10 | 23 |
| TH-2085 | 10 | 4 | 36 | 41 | 14 | 26 | 33 | 17 | 28 | 90 | 31 | ~60 | 50 | 80 |
| TH-2279 | ~50 | ~50 | >100 | >100 | ~100 | >100 | >100 | >100 | >100 | >100 | >100 | >100 | >100 | >100 |

$IC_{50}$ values in $\mu M$.

taining (mmol/L) KCl 140, EGTA 10, $MgCl_2$ 1, $CaCl_2$ 1, dextrose 10, and HEPES 10 (pH 6.4). Whole cell recording was performed, with $Ba^{2+}$ used as the charge carrier, by the ruptured patch method in a solution containing (mmol/L) $BaCl_2$ 10, TEA-Cl 140, CsCl ϵ, and HEPES 10 (pH 7.4 adjusted with TEA-OH). The internal pipette solution contained (mmol/L) CsCl 55, CS $SO_3$ 75, $MgCl_2$ 10, EGTA 0.1, and HEPES 10 (pH adjusted to 7.2 with (CsOH). Currents were recorded using an Axopatch 200A, a Digidata 1200 A/D converter and pCLAMP software (Axon Instruments, Inc.).

The current of the cell in the depolarized cell was recorded over time (control). Within a few minutes after the control plot was recorded, the cells were again depolarized, but this time, the bath contained in addition 10 µM TH-1177. The current was recorded for the same length of time as the control. The current was recorded at about zero pA. Then the cells in the bath containing 10 µM TH-1177 were depolarized again, but this time the bath medium containing TH-1177 was aspirated out and replaced with fresh calcium medium depolarizing medium and the current was measured.

The results are graphically depicted in FIG. 41.

The experiment clearly illustrates that TH-1177 inhibits the ability of calcium to cross the cell membrane in these cells. Allowing TH-1177 to wash out restores the ability of calcium to cross the cell membrane.

EXAMPLE 10

The procedure of Example 9 was repeated except the cells were transfected with 2 µg of α1G subunit prepared in accordance with the procedure described in Cribbs, et al., *FEBS Letters,* 66, 54–58 (2000). Here the cells were depolarized using the depolarizing medium of Example 9. When the current reached the maximum level, then 10 µm pH 1177 was added to the medium and the change in current was observed. The current was measured at about zero pA. When the current remained constant, the TH-1177 was washed out, in accordance with the procedure in Example 9 and the change in the current value was again recorded.

The change in the current was plotted and the plot is depicted in FIG. 42.

This experiment also shows that TH-1177 completely inhibits the ability of calcium to cross the cell membrane in the Xenopus oocyte cell transfected with the α1G subunit. Allowing TH-1177 to wash out restore the ability of calcium to cross the cell membrane.

The data in Examples 9 and 10 clearly demonstrate that compounds of the present invention, e.g., TH-1177 and its cogeners inhibit T-like calcium channels.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims.

What is claimed is:
1. A compound of the formula:

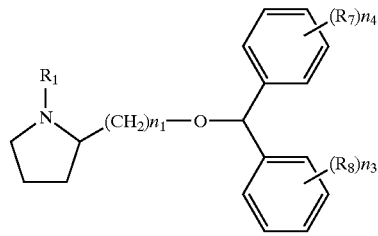

wherein
$n_3$ and $n_4$ are independently 1–5;
$n+n_1$ is 1–8
$R_1$ is $(CH_2)n—Z—R_5$, hydrogen or lower alkyl, $R_7$ and each $R_8$ are independently hydrogen, an electron donating or electron withdrawing group;
Z is $CH_2$, O, S or NH; and
$R_5$ is a cyclic ring containing 6–14 ring carbon atoms and is aromatic and may be unsubstituted or substituted with an electron withdrawing group or electron donating group.

2. The compound according to claim 1 having the formula:

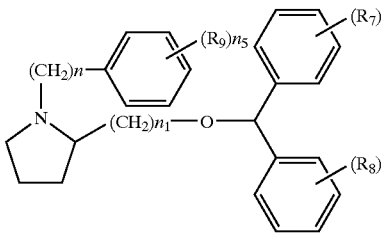

wherein
$R_9$ is hydrogen, an electron donating group or electron withdrawing group and;
$n_5$ is 1–5.

3. The compound according to claim 2, wherein n is 1.

4. The compound according to anyone of claim 1 or 2 wherein, the electron donating group is amino, hydroxy or lower alkyl, and the electron withdrawing group is halo, lower alkyl, nitro or nitrile.

5. The compound according to claim 4 wherein the electron donating group is lower alkoxy and the electron withdrawing group is halo.

6. The compound according to claim 1 or wherein $R_7$ and $R_8$ are halo.

7. A compound according to the formula:

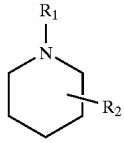

wherein $R_1$ is $(CH_2)n—Z—(R_5)$, Q, hydrogen or lower alkyl;
$R_2$ is hydrogen or Q';
Q and Q' may be the same or different and are independently

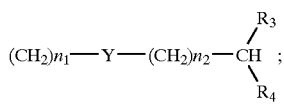

Z is a chemical bond, $CH_2$, O, S or NH;

Y is $CH_2$, O, S or NH;

$R_3$, $R_4$ and $R_5$ are independently cyclic rings containing 6–14 ring carbon atoms, and containing no hetero ring atoms, which cyclic rings may be completely saturated, partially unsaturated or aromatic, and which are unsubstituted or substituted with an electron donating group or electron withdrawing group;

$R_3$ and $R_4$ may be fused to form a cyclic ring structure containing 12–28 carbon atoms;

$n_2$ is 0–8; and n and $n_1$ are independently 1–8, provided that either $R_1$ is O or $R_2$ is Q'.

8. The compound according to claim 7 having the formula:

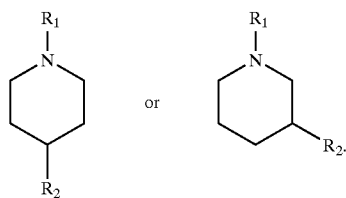

9. The compound according to claim 7 or 8 wherein Y is 0.

10. The compound according to claim 7 wherein $R_3$ and $R_4$ are independently aromatic.

11. The compound according to claim 7 having the formula:

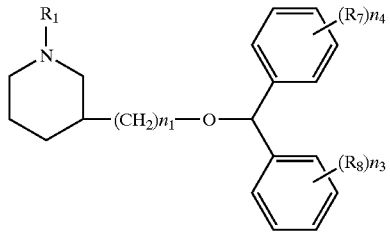

wherein $n_3$ and $n_4$ are independently 1–5;

$n+n_1$ is 1–8

$R_1$ is $(CH_2)n$—Z—$R_5$, hydrogen or lower alkyl;

each $R_7$ and each $R_8$ are the same or different and are independently hydrogen, an electron donating or electron withdrawing group;

Z is $CH_2$, O, S or NH;

$R_5$ is a cyclic ring containing 6–14 ring carbon atoms and is aromatic and may be unsubstituted or substituted with an electron withdrawing group or electron donating group.

12. The compound according to claim 7 having the formula:

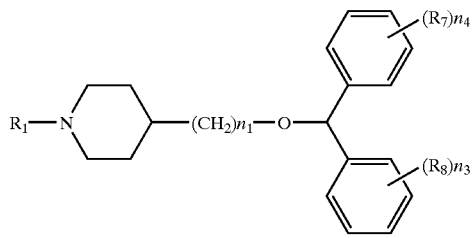

wherein $n_3$ and $n_4$ are independently 1–5;

$n+n_1$ is 1–8

$R_1$ is $(CH_2)n$—Z—$R_5$, hydrogen or lower alkyl;

each $R_7$ and each $R_8$ are the same or different and are independently hydrogen, an electron donating or electron withdrawing group;

Z is $CH_2$, O, S or NH;

$R_5$ is a cyclic ring containing 6–14 ring carbon atoms and is aromatic and may be unsubstituted or substituted with an electron withdrawing group or electron donating group.

13. The compound according to claim 12 having the formula:

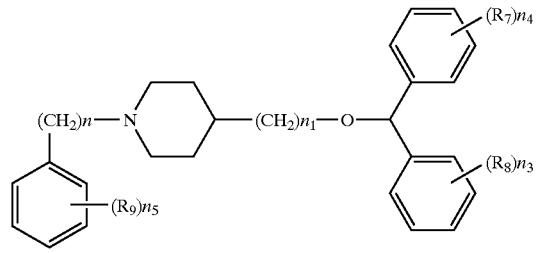

wherein each $R_7$ and each $R_8$ are the same or different and are independently hydrogen, an electron donatating or electron withdrawing group;

$R_9$ is hydrogen, an electron donating group or electron withdrawing group;

$n_3$, $n_4$ and $n_5$ are independently 1–5; and n and $n_1$ are independently 1–8.

14. The compound according to claim 11 having the formula:

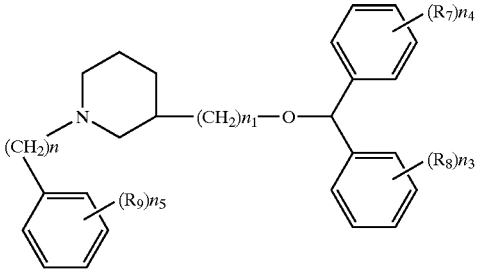

wherein each $R_7$ and each $R_8$ are the same or different and are independently hydrogen, an electron donating or electron withdrawing group;

$R_9$ is hydrogen, an electron donating group or electron withdrawing group;

$n_3$, $n_4$ and $n_5$ are independently 1–5; and n and $n_1$ are independently 1–8.

15. The compound according to anyone of claims 11–14 wherein $n_1$ is 1.

16. The compound according to anyone of claims 11–14 wherein the electron donating group is amino, hydroxy or alkoxy and the electron withdrawing group is halo, lower alkyl, nitro or nitrile.

17. The compound according to claim 8 having the structure

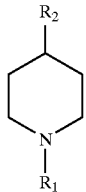

wherein $R_1$ is Q and $R_2$ is hydrogen or Q'.

18. The compound according to claim 17 wherein $R_1$ is

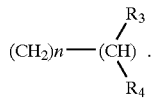

19. The compound according to claim 18 wherein n is 1.

20. The compound according to any one of claims 17–19 wherein $R_3$ and $R_4$ are independently phenyl.

21. The compound according to claim 17 having the structure

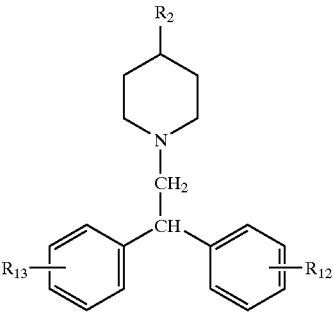

wherein $R_{13}$ and $R_{12}$ are independently hydrogen, an electron donating group or an electron withdrawing group.

22. The compound according to claim 21 wherein $R_2$ is H.

23. The compound according to claim 21 wherein $R_2$ is

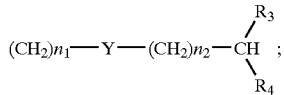

wherein

Y is O, S, NH or $CH_2$;

$R_3$ and $R_4$ are independently the same or different and are cyclic rings containing 6–14 ring carbon atoms, which cyclic rings are aromatic and which are unsubstituted or substituted with an electron donating group or an electron withdrawing group;

$n_1$ is 0–8, and $n_2$ is 0–8.

24. The compound according to claim 23 wherein Y is O.

25. The compound according to claim 23 or 24 wherein $R_3$ and $R_4$ are independently phenyl rings which are unsubstituted or substituted with an electron donating group or electron donating groups.

26. The compound according to claim 23 wherein $n_1$ is 1.

27. The compound according to claim 23 wherein $n_2$ is 0.

28. The compound according to claim 23 wherein $n_1$ is 1 and $n_2$ is 0.

29. The compound according to claim 21 having the formula:

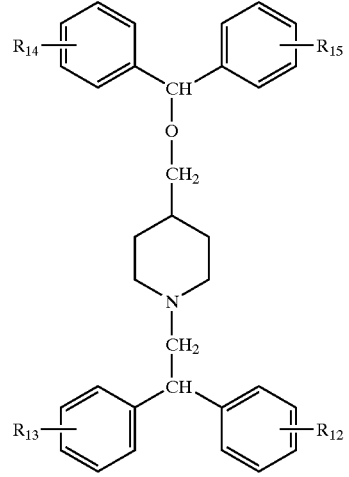

wherein $R_{12}$, $R_{13}$, $R_{14}$ and $R_{15}$ are independently hydrogen, electron withdrawing group or electron donating group.

30. A stereoisomer of the compound of claim 1 or 7.

31. A pharmaceutical composition comprising a cytostatic effective amount of a compound according to claim 1 or 7 and a pharmaceutically acceptable carrier therefor.

32. A method of inhibiting prostrate, breast, pancreatic liver, lung, colon or ovarian cancer cell proliferation in a mammal in need of such treatment, comprising administering to said mammal a cytostatic effective amount of a compound according to any one of claims 1, 2, 7, 8, 11, 12, 13, 14 or 21.

33. The method according to claim 32 wherein said mammal is a human.

34. The method according to claim 33 wherein the compound is administered in amounts ranging from about 0.5 mg to about 100 mg/kg of body weight per day.

35. A method of treating prostrate, breast, pancreatic liver, lung, colon or ovarian cancer in a mammal in need thereof comprising administering to said mammal an effective amount of a compound according to any one of claims 1, 2, 7, 8, 11, 12, 13, 14 or 21.

36. A method of treating prostrate, breasts pancreatic liver, lung, colon or ovarian cancer in an animal afflicted with such disease which comprises administering to an animal in need of such treatment an organic calcium blocker compound according to any one of claims 1, 2, 7, 8, 11, 12, 13, 14 or 21 that inhibits the entry of calcium ions across the cell membrane through a T-like calcium channel in cancer cells in response to a mitogenic stimulus, said calcium blocker being present in an amount effective to inhibit the passage of calcium into the cell.

37. The method according to claim 36 in which the compound blocks calcium entry into the cell by interacting with the α1 subunit of a calcium channel.

38. The method according to claim 37 wherein the α1 subunit is an α1G or α1H.

* * * * *